(12) United States Patent
Dales et al.

(10) Patent No.: US 8,314,138 B2
(45) Date of Patent: Nov. 20, 2012

(54) PYRAZOLE DERIVATIVE AS SCD1 INHIBITORS FOR THE TREATMENT OF DIABETES

(75) Inventors: Natalie Dales, Arlington, MA (US); Zaihui Zhang, Vancouver (CA)

(73) Assignee: Novartis AG, Basel (CH)

( * ) Notice: Subject to any disclaimer, the term of this patent is extended or adjusted under 35 U.S.C. 154(b) by 448 days.

(21) Appl. No.: 12/438,654

(22) PCT Filed: Aug. 22, 2007

(86) PCT No.: PCT/US2007/018554
§ 371 (c)(1),
(2), (4) Date: Feb. 24, 2009

(87) PCT Pub. No.: WO2008/024390
PCT Pub. Date: Feb. 28, 2008

(65) Prior Publication Data
US 2010/0239520 A1    Sep. 23, 2010

Related U.S. Application Data

(60) Provisional application No. 60/823,425, filed on Aug. 24, 2006.

(51) Int. Cl.
*A61K 31/415* (2006.01)
(52) U.S. Cl. ............... 514/406; 546/275.4; 548/202; 548/266.2; 548/373.1; 548/469; 548/560
(58) Field of Classification Search ............ 514/406; 546/275.4; 548/202, 266.2, 373.1, 469, 560
See application file for complete search history.

(56) References Cited

U.S. PATENT DOCUMENTS

| | | | |
|---|---|---|---|
| 5,254,576 A | 10/1993 | Romine et al. | |
| 6,054,435 A | 4/2000 | Or et al. | |
| 6,348,480 B1 * | 2/2002 | Kubota et al. | 514/361 |
| 2005/0054634 A1 | 3/2005 | Busch et al. | |
| 2005/0256118 A1 | 11/2005 | Altenbach et al. | |
| 2005/0256158 A1 | 11/2005 | Ghosh et al. | |
| 2005/0272728 A1 | 12/2005 | Altenbach et al. | |
| 2006/0014700 A1 | 1/2006 | Cohen et al. | |
| 2006/0041006 A1 | 2/2006 | Ibrahim et al. | |
| 2006/0041137 A1 | 2/2006 | Cao et al. | |
| 2007/0004711 A1 | 1/2007 | Zhang | |
| 2008/0233163 A1 | 9/2008 | Assaf | |
| 2008/0306121 A1 | 12/2008 | Nan et al. | |
| 2008/0312435 A1 | 12/2008 | Saito et al. | |

FOREIGN PATENT DOCUMENTS

| | | |
|---|---|---|
| CN | 1618796 A | 5/2005 |
| EP | 0159677 A2 | 10/1985 |
| EP | 0554956 A1 | 11/1993 |
| EP | 1894930 A1 | 3/2008 |
| EP | 1921077 A1 | 5/2008 |
| JP | 04247076 A | 9/1992 |
| JP | 2002114784 A | 4/2002 |
| JP | 2007-126454 A | 5/2007 |
| WO | WO 94/29300 | * 12/1994 |
| WO | 98/54164 A1 | 12/1998 |
| WO | 00/06085 A2 | 2/2000 |
| WO | 00/34255 A1 | 6/2000 |
| WO | 00/55168 A | 9/2000 |
| WO | 00/55168 A1 | 9/2000 |
| WO | 02/26722 A1 | 4/2002 |
| WO | 02/50091 A | 6/2002 |
| WO | 02/50091 A1 | 6/2002 |
| WO | 02/064545 A1 | 8/2002 |
| WO | 03/024962 A1 | 3/2003 |
| WO | 03/029245 A1 | 4/2003 |
| WO | 03/089412 A | 10/2003 |
| WO | 03/089412 A1 | 10/2003 |
| WO | 03/099821 A1 | 12/2003 |
| WO | 2004/032848 A2 | 4/2004 |
| WO | 2004/062665 A | 7/2004 |
| WO | 2004/072025 A | 8/2004 |
| WO | 2004/080972 A1 | 9/2004 |
| WO | 2004/089415 A2 | 10/2004 |
| WO | 2004/089416 A2 | 10/2004 |
| WO | 2004/089470 A2 | 10/2004 |

(Continued)

OTHER PUBLICATIONS

Davies et al., "N-H Insertion reactions of rhodium carbenoids. Part 5: A convenient route to 1,3-azoles," Tetrahedron 60:3967-3977 (2004).
Kerdesky et al., "4-Hyroxythiazole Inhibitors of 5-Lipoxygenase," J. Med. Chem. 34:2158-2165 (1991).
Meanwell et al., "Nonprostanoid Prostacyclin Mimetics, 5. Structure-Activity Relationships Associated with [3-[4(4,5-Diphenyl-2-oxazolyl)-5-oxazolyl] phenoxy]acetic Acid" J. Med. Chem. 36:3884-3903 (1993).
Nussbaumer et al., "21-23-Dithia-3, 13-diazaporphycenes—Novel Aromatic Porphycene Analogues Incorporating Thiazole," Eur. J. Org. Chem 2000:2449-2457 (2000).

(Continued)

*Primary Examiner* — Douglas M Willis
(74) *Attorney, Agent, or Firm* — Joshua Roth

(57) ABSTRACT

The present invention provides heterocyclic derivatives of formula I that modulate the activity of stearoyl-CoA desaturase. Methods of using such derivatives to modulate the activity of stearoyl-CoA desaturase and pharmaceutical compositions comprising such derivatives are also encompassed.

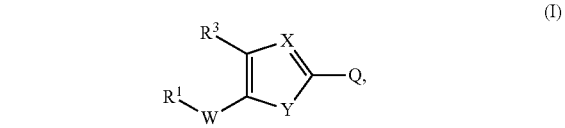

wherein Q is

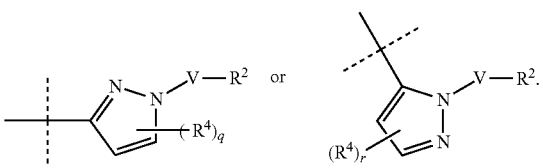

2 Claims, No Drawings

FOREIGN PATENT DOCUMENTS

| | | | |
|---|---|---|---|
| WO | 2004/092177 | A1 | 10/2004 |
| WO | 2004-096220 | A1 | 11/2004 |
| WO | 2004/100946 | A1 | 11/2004 |
| WO | 2005/002552 | A2 | 1/2005 |
| WO | 2005/011655 | A | 2/2005 |
| WO | 2005/044797 | A1 | 5/2005 |
| WO | 2005/061513 | A1 | 7/2005 |
| WO | 2005/075469 | A1 | 8/2005 |
| WO | 2005/085241 | A1 | 9/2005 |
| WO | 2005/089770 | A1 | 9/2005 |
| WO | 2005/089771 | A1 | 9/2005 |
| WO | 2005/090319 | A1 | 9/2005 |
| WO | 2005/100321 | A1 | 10/2005 |
| WO | 2005/105065 | A | 11/2005 |
| WO | 2005/105065 | A2 | 11/2005 |
| WO | 2006/020767 | A2 | 2/2006 |
| WO | 2006/122011 | A2 | 11/2006 |
| WO | 2006/122150 | A1 | 11/2006 |
| WO | 2007/073300 | A | 6/2007 |
| WO | 2007/087429 | A2 | 8/2007 |

OTHER PUBLICATIONS

Oreliana et al., "Reversible Fiber-Optic Fluorosensing of Lower Alcohols," Anal. Chem. 67:2231-2238 (1995).

Seko et al., "Synthesis and Platelet Aggregation Inhibitory Activity of Diphenylazole Derivatives. I. Thiazole and Imidazole Derivatives," Chem. Pharm. Bull 39(3):651-657 (1991).

Rose et al., "Structure-Activity Relationship (SAR): Effort Towards Blocking N-Glucuronidation of Indazoles (PF-03376056) by Human UGT1A Enzymes," Drug Metabolism Letters 3:28-34 (2009).

Weiss et al., "Firefly-Luciferin and its Analogs: A Source of new Luminescence Dyes and Ligands," Bioluminescence and Chemiluminescence: Chemistry, Biology and Applications, Proceedings of the International Symposium, 14th San Diego, CA, United States, Oct. 15-19, 2006 (2007) 247-250.

Caiku et al., "Synthesis of L-Camphorsulphonic Acid Tetrazolium Salts," Huagong Shikan (Chemical Industry Times), vol. 22, No. 3, pp. 7-9 (2008).

* cited by examiner

PYRAZOLE DERIVATIVE AS SCD1 INHIBITORS FOR THE TREATMENT OF DIABETES

This application is the National Stage of Application No. PCT/US2007/018554, filed on Aug. 22, 2007, which claims benefit under 35 U.S.C. §119(e) of U.S. Provisional Application No. 60/823,425, filed Aug. 24, 2006, the contents of which are incorporated herein by reference in their entirety.

The present invention relates generally to, the field of inhibitors of stearoyl-CoA desaturase, such as heterocyclic derivatives, and uses for such compounds in treating and/or preventing various human diseases, including those mediated by stearoyl-CoA desaturase (SCD) enzymes, preferably SCD1, especially diseases related to elevated lipid levels, cardiovascular disease, diabetes, obesity, metabolic syndrome, dermatological disorders and the like.

BACKGROUND OF THE INVENTION

Acyl desaturase enzymes catalyze the formation of a double bond in fatty acids derived from either dietary sources or de novo synthesis in the liver. In mammals, at least three fatty acid desaturases exists, each with differing specificity: delta-9, delta-6, and delta-5, which introduce a double bond at the 9-10, 6-7, and 5-6 positions respectively.

Stearoyl-CoA desaturases (SCDs) act with cofactors (other agents) such as NADPH, cytochrome b5, cytochrome b5 reductase, Fe, and molecular $O_2$ to introduce a double bond into the C9-C10 position (delta 9) of saturated fatty acids, when conjugated to Coenzyme A (CoA). The preferred substrates are palmitoyl-CoA (16:0) and stearoyl-CoA (18:0), which are converted to palmitoleoyl-CoA (16:1) and oleyl-CoA (18:1), respectively. The resulting mono-unsaturated fatty acids are substrates for further metabolism by fatty acid elongases or incorporation into phospholipids, triglycerides, and cholesterol esters. A number of mammalian SCD genes have been cloned. For example, two genes have been identified in humans (hSCD1 and hSCD5) and four SCD genes have been isolated from mouse (SCD1, SCD2, SCD3, and SCD4). While the basic biochemical role of SCD has been known in rats and mice since the 1970s (Jeffcoat, R. et al., *Eur. J. Biochem.* (1979), Vol. 101, No. 2, pp. 439-445; de Antueno, R. et al., *Lipids* (1993), Vol. 28, No. 4, pp. 285-290), it has only recently been directly implicated in human disease processes.

The two human SCD genes have been previously described: hSCD1 by Brownlie et. al., PCT published patent application, WO 01/62954, the disclosure of which is hereby incorporated by reference in its entirety, and hSCD2 by Brownlie, PCT published patent application, WO 02/26944, incorporated herein by reference in its entirety.

To date, the only small-molecule, drug-like compounds known that specifically inhibit or modulate SCD activity are found in the following PCT Published Patent Applications: WO 06/034338, WO 06/034446, WO 06/034441, WO 06/034440, WO 06/034341, WO 06/034315, WO 06/034312, WO 06/034279, WO 06/014168, WO 05/011657, WO 05/011656, WO 05/011655, WO 05/011654, WO 05/011653, WO 06/130986, WO 07/009236, WO 06/086447, WO 06/101521, WO 06/125178, WO 06/125179, WO 06/125180, WO 06/125181, WO 06/12514, WO 07/044085, WO 07/046867, WO 07/046868, WO 07/050124, and WO 07/056846. SCD inhibitors have also been described in the following publications: Zhao et al. "Discovery of 1-(4-phenoxypiperidin-1-yl)-2-arylaminoethanone stearoyl CoA desaturase 1 inhibitors", *Biorg. Med. Chem. Lett.*, (2007), 17(12), 3388-3391 and Liu et al. "Discovery of potent, orally bioavailable stearoyl-CoA desaturase 1 inhibitors", *J. Med. Chem.*, (2007), 50(13), 3086-3100. Before the discovery of the above compounds, only certain long-chain hydrocarbons, analogs of the substrate stearic acid, had been used to study SCD activity. Known examples include thia-fatty acids, cyclopropenoid fatty acids, and certain conjugated linoleic acid isomers. Specifically, cis-12, trans-10 conjugated linoleic acid is believed to inhibit SCD enzyme activity and reduce the abundance of SCD1 mRNA, while cis-9, trans-11 conjugated linoleic acid does not. Cyclopropenoid fatty acids, such as those found in stercula and cotton seeds, are also known to inhibit SCD activity. For example, sterculic acid (8-(2 octylcyclopropenyl)octanoic acid) and malvalic acid (7-(2-oclylcyclopropenyl)heptanoic acid) are C18 and C16 derivatives of sterculoyl and malvaloyl fatty acids, respectively, having cyclopropene rings at their C9-C10 position. These agents must be coupled to CoA to act as inhibitors, and are believed to inhibit SCD enzymatic activity by direct interaction with the enzyme complex, thus inhibiting delta-9 desaturation. Other agents that may inhibit SCD activity include thia-fatty acids, such as 9-thiastearic acid (also called 8-nonylthiooctanoic acid) and other fatty acids.

There is a major unmet need for small molecule inhibitors of SCD enzyme activity because compelling evidence now exists that SCD activity is directly implicated in common human disease processes: See e.g., Attie, A. D. et al., "Relationship between stearoyl-CoA desaturase activity and plasma triglycerides in human and mouse hypertriglyceridemia", *J. Lipid Res.* (2002), Vol. 43, No. 11, pp. 1899-907; Cohen, P. et al., "Role for stearoyl-CoA desaturase-1 in leptin mediated weight loss", *Science* (2002), Vol. 297, No. 5579, pp. 240-3, Ntambi, J. M. et al., "Loss of stearoyl-CoA desaturase-1 function protects mice against adiposity", *Proc. Natl. Acad. Sci. U.S.A.* (2002), Vol. 99, No. 7, pp. 11482-6.

The present invention solves this problem by presenting new drug-like classes of compounds that are useful in modulating SCD activity and regulating lipid levels, especially plasma lipid levels, and which are useful in the treatment of SCD-mediated diseases such as diseases related to dyslipidemia and disorders of lipid metabolism, especially diseases related to elevated lipid levels, cardiovascular disease, diabetes, obesity, metabolic syndrome and the like.

SUMMARY OF THE INVENTION

The present invention provides heterocyclic derivatives that modulate the activity of stearoyl-CoA desaturase. Methods of using such derivatives to modulate the activity of stearoyl-CoA desaturase and pharmaceutical compositions comprising such derivatives are also encompassed.

Accordingly, in one aspect, the invention provides compounds of formula, (I):

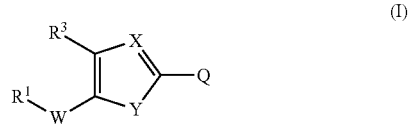

X is N or CH;

Y is NH, O, S or N—CH$_3$;

Q is

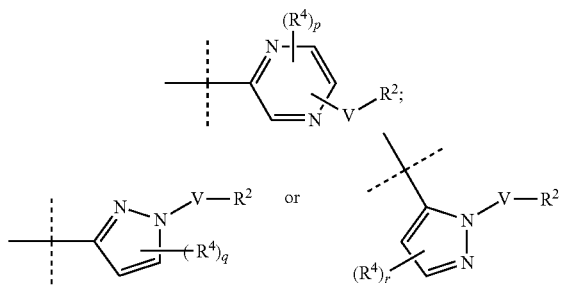

wherein when Q is

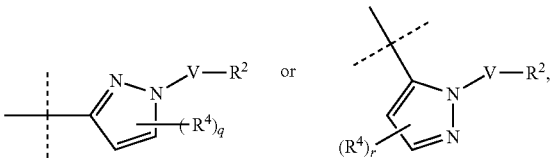

W is selected from —N(R$^6$)C(O)—, —C(O)N(R$^6$)—, —OC(O)N(R$^6$)—, —N(R$^6$)C(O)O—, —N(R$^6$)C(O)N(R$^6$)—, —O—, —N(R$^6$)—, —S—, —S(O)$_t$—, —N(R$^6$)S(O)$_t$—, —S(O)$_t$N(R$^6$)—, —OS(O)$_t$N(R$^6$)—, —C(O)—, —OC(O)—, —C(O)O—, —N(R$^6$)C(=N(R$^{6a}$))N(R$^6$)—, —N(R$^6$)((R$^{6a}$)N=)C—, —C(=N(R$^{6a}$))N(R$^6$)—, an aryl, a heteroaryl, a heterocyclyl, an alkynylene, an alkenylene, an alkylene or a direct bond;

V is selected from —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —N(R$^5$)—, —S—, —S(O)$_t$—, —N(R$^5$)S(O)$_2$—, —S(O)$_2$N(R$^5$)—, —OS(O)$_2$N(R$^5$)—, —C(O)—, —OC(O)—, —C(O)O—, —CR$^5$C(O)N(R$_5$)—, —(CR$^5_2$)$_n$C(O)—, —(CR$^5_2$)$_n$O—, —(CR$^5_2$)$_n$N(R$^6$)—, —(CR$^5_2$)$_n$N(R$^5$)C(O)—, —(CR$^5_2$)$_n$N(R$^5$)C(O)O—, —(CR$^5_2$)$_n$N(R$^5$)S(O)$_t$—, —N(R$^5$)C(=N(R$^{5a}$))NR$^5$—, —N(R$^5$)((R$^{5a}$)N=)C—, —C(=N(R$^{5a}$))N(R$^5$)—, —(CR$^5_2$)$_n$CR$^5$=CR$^5$, an alkynylene, an alkenylene, an alkynyl, an alkylene or a direct bond;

t is 1 or 2;
p is 0, 1 or 2;
n is to 6;
R$^1$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
or R$^1$ is a multi-ring structure having 2 to 4 rings wherein the rings are, independently selected from the group consisting of cycloalkyl, heterocyclyl, aryl and heteroaryl and where some or all of the rings, may be fused to each other;
R$^2$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
or R$^2$ is a multi-ring structure having 2 to 4 rings wherein the rings are independently selected from the group consisting of cycloalkyl, heterocyclyl, aryl and heteroaryl and where some or all of the rings may be fused to each other;
R$^3$ is selected from the group consisting of hydrogen, alkyl, alkenyl, alkynyl, hydroxyalkyl, alkoxyalkyl, cycloalkyl, cycloalkylalkyl, heterocyclyl, aryl, aralkyl, heteroaryl, halo, trifluoromethyl, trifluoromethoxy, cyano and —N(R$^6$)$_2$;
R$^4$ is selected from the group consisting of alkyl, halo, —N(R$^6$)$_2$, haloalkyl, hydroxyl, alkoxy, —N(R$^2$)$_2$, cycloalkylalkyl and aralkyl;
R$^5$ and R$^6$ are independently selected from the group consisting of hydrogen, alkyl, halo, aryl, heteroaryl, cycloalkyl, hydroxyalkyl, cycloalkylalkyl and aralkyl;
R$^{5a}$ and R$^{6a}$ are independently selected from the group consisting of hydrogen, alkyl, cycloalkylalkyl and cyano;
and
wherein when Q is W is selected from —N(R$^6$)C(O)—, —C(O)N(R$^6$)—, —OC(O)N(R$^6$)—, —N(R$^6$)C(O)O—, —N(R$^6$)C(O)N(R$^6$)—, —O—, —N(R$^6$)—, —S(O)$_t$—, —N(R$^6$)S(O)$_t$—, —S(O)$_t$N(R$^6$)—, —OS(O)$_t$N(R$^6$)—, —C(O)—, —OC(O)—, —C(O)O—, —N(R$^6$)C(=N(R$^{6a}$))N(R$^6$)—, —N(R$^6$)((R$^{6a}$)N=)C—, —C(=N(R$^{6a}$))N(R$^6$)—, an aryl, a heteroaryl, a heterocyclyl, an alkynylene, an alkenylene, an alkylene or a direct bond;

V is selected from —C(O)N(R$^5$)—, —S(O)$_t$—, —S(O)$_2$N(R$^5$)—, —C(O)—, —C(O)O—, —C(O)N(R$^5$)—, —CR$^5_2$C(O)N(R$^5$)—, —(CR$^5_2$)$_n$C(O)—, —(CR$^5_2$)$_n$O—, —(CR$^5_2$)$_n$N(R$^6$)—, —(CR$^5_2$)$_n$N(R$^5$)C(O)—, —(CR$^5_2$)$_n$N(R$^5$)C(O)O—, —(CR$^5_2$)$_n$N(R$^5$)S(O)$_t$—, an aryl, a heteroaryl, a heterocyclyl, an alkynylene, an alkenylene, an alkylene or a direct bond;
t is 1 or 2;
q is 0, 1, or 2;
r is 0, 1 or 2;
n is 1 to 6;
R$^1$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
or R$^1$ is a multi-ring structure having 2 to 4 rings wherein the rings are independently selected from the group consisting of cycloalkyl, heterocyclyl, aryl and heteroaryl and where some or all of the rings may be fused to each other;
R$^2$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
or R$^2$ is a multi-ring structure having 2 to 4 rings wherein the rings are independently selected from the group consisting of cycloalkyl, heterocyclyl, aryl and heteroaryl and where some or all of the rings may be fused to each other;
R$^3$ is selected from the group consisting of hydrogen, alkyl, alkenyl, alkynyl, hydroxyalkyl, alkoxyalkyl, cycloalkyl, cycloalkylalkyl, heterocyclyl, aryl, aralkyl, heteroaryl, halo, trifluoromethyl, trifluoromethoxyl, cyano and —N(R$^6$)$_2$;

R$^4$ is selected from the group consisting of alkyl, haloalkyl, hydroxyl, alkoxy, —N(R$^2$)$_2$, cycloalkylalkyl and aralkyl;

R$^5$ and R$^6$ are independently selected from the group consisting of hydrogen, alkyl, halo, aryl, heteroaryl, cycloalkyl, hydroxyalkyl, cycloalkylalkyl and aralkyl;

R$^{5a}$ and R$^{6a}$ are independently selected from the group consisting of hydrogen, alkyl, cycloalkylalkyl and cyano; or as a stereoisomer, enantiomer or tautomer thereof, a pharmaceutically acceptable salt thereof, a pharmaceutical composition thereof or a prodrug thereof.

In another aspect, the invention provides methods of treating an SCD-mediated disease or condition in a mammal, preferably a human, wherein the methods comprise administering to the mammal in need thereof a therapeutically effective amount of a compound of the invention as set forth above.

In another aspect, the invention provides compounds or pharmaceutical compositions useful in treating, preventing and/or diagnosing a disease or condition relating to SCD biological activity such as the diseases encompassed by cardiovascular disorders and/or metabolic syndrome (including dyslipidemia, insulin resistance and obesity).

In another aspect, the invention provides methods of preventing or treating a disease or condition related to elevated lipid levels, such as plasma lipid levels, especially elevated triglyceride and/or cholesterol levels, in a patient afflicted with such elevated levels, comprising administering to said patient a therapeutically or prophylactically effective amount of a composition as disclosed herein. The present invention also relates to novel compounds having therapeutic ability to reduce lipid levels in an animal, especially triglyceride and cholesterol levels.

In another aspect, the invention provides pharmaceutical compositions comprising the compounds of the invention as set forth above, and pharmaceutically acceptable excipients. In one embodiment, the present invention relates to a pharmaceutical composition comprising a compound of the invention in a pharmaceutically acceptable carrier and in an amount effective to modulate triglyceride level, or to treat diseases related to dyslipidemia and disorders of lipid metabolism, when administered to an animal, preferably a mammal, most preferably a human patient. In an embodiment of such composition, the patient has an elevated lipid level, such as elevated plasma triglycerides or cholesterol, before administration of said compound and said compound is present in an amount effective to reduce said lipid level.

In another aspect, the invention provides methods for treating a patient for, or protecting a patient from developing, a disease or condition mediated by stearoyl-CoA desaturase (SCD), which methods comprise administering to a patient afflicted with such disease or condition, or at risk of developing such disease or condition, a therapeutically effective amount of a compound that inhibits activity of SCD in a patient when administered thereto.

In another aspect, the invention provides methods for treating a range of diseases involving lipid metabolism and/or lipid homeostasis utilizing compounds identified by the methods disclosed herein. In accordance therewith, there is disclosed herein a range of compounds having said activity, based on a screening assay for identifying, from a library of test compounds, a therapeutic agent which modulates the biological activity of said SCD and is useful in treating a human disorder or condition relating to serum levels of lipids, such as triglycerides, VLDL, HDL, LDL, and/or total cholesterol.

It is understood that the scope of the invention as it relates to compounds of formula (I) is not intended to encompass compounds which are known, including, but not limited to, any specific compounds which are disclosed and/or claimed in the following publications:
PCT Published Patent Application, WO 00/25768;
PCT Published Patent Application, WO 99/47507;
PCT Published Patent Application, WO 01/60458;
PCT Published Patent Application, WO 01/60369;
PCT Published Patent Application, WO 94/26720;
European Published Patent Application, 0 438 230;
European Published Patent Application, 1 184 442;
CA 2,114,178; and U.S. Pat. No. 5,334,328;
U.S. Pat. No. 5,310,499; and
US Published Patent Application, 2003/0127627.

DETAILED DESCRIPTION OF THE INVENTION

Definitions

Certain chemical groups named herein are preceded by a shorthand notation indicating the total number of carbon atoms that are to be found in the indicated chemical group. For example, C$_7$-C$_{12}$alkyl describes an alkyl group, as defined below, having a total of 7 to 12 carbon atoms, and C$_4$-C$_{12}$cycloalkylalkyl describes a cycloalkylalkyl group, as defined below, having a total of 4 to 12 carbon atoms. The total number of carbons in the shorthand notation does not include carbons that may exist in substituents of the group described.

Accordingly, as used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl(iso-propyl), n-butyl, n-pentyl, 1,1-dimethylethyl(t-butyl), and the like. Unless stated otherwise specifically in the specification, an alkyl group may be optionally substituted by one or more of the following groups: alkyl, alkenyl, halo, haloalkyl, cyano, aryl, cycloalkyl, heterocyclyl, heteroaryl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$), —S(O)$_t$OR$^{16}$, —SR$^{16}$, —S(O)$_t$R$^{16}$, and —S(O)$_t$N(R$^{14}$)$_2$, where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably two to eight carbon atoms or two to six carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one or more of the following groups: alkyl, alkenyl, halo, haloalkylaryl, aralkyl, cycloalkyl, cycloalkylalkyl, heterocyclyl, heterocyclylalkyl, heteroaryl, heteroarylalkyl, —OR$^{14}$, —OC(O)—R$^{14}$, —N(R$^{14}$)$_2$, —C(O)R$^{14}$, C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$), —S(O)(OR$^{16}$, —SR$^{16}$, —S(O)$_t$R$^{16}$, and —S(O)$_t$N(R$^{14}$), where each R$^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; and each R$^{16}$ is alkyl, cycloalkyl, cycloalkylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms, preferably two to eight carbon atoms or two to six carbon atoms and which is attached to the rest of the molecule by a single bond, e.g., ethynyl, propynyl, butynyl, pentynyl, hexynyl, and the like. Unless stated otherwise specifically in the specification, an alkynyl group may be optionally substituted by one or more of the following groups: alkyl, alkenyl, halo, haloalkyl, aryl, aralkyl, cycloalkyl, cycloalkylalkyl, heterocyclyl, heterocyclylalkyl, heteroaryl, heteroarylalkyl, —OR$^{14}$, —OC(O)—R$^{14}$—N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$), —S(O)$_t$OR$^{16}$, —SR$^{16}$, —S(O)$_t$R$^{16}$, and —S(O)$_t$N(R$^{14}$)$_2$, where each R$^{14}$ is independently hydrogen, alkyl, haloalkyl, cycloalkyl, cycloalkylalkyl, aryl, aralkyl, heterocyclyl, heterocyclylalkyl, heteroaryl, or heteroarylalky; and each R$^{16}$ is alkyl, cycloalkyl, cycloalkylalkyl, aryl, aralkyl, heterocyclyl, heterocyclylalkyl, heteroaryl or heteroarylalkyl.

"Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons or one to six carbon atoms, e.g., methylene, ethylene, propylene, n-butylene, and the like. The alkylene chain may be attached to the rest of the molecule and to the radical group through one carbon within the chain or through any two carbons within the chain. The alkylene chain may be optionally substituted by one or more of the following groups: alkyl, alkenyl, halo, haloalkyl, cyano, aryl, cycloalkyl, heterocyclyl, heteroaryl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$), —S(O)$_t$OR$^{16}$, —SR$^{16}$, —S(O)$_t$R$^{16}$, and —S(O)$_t$N(R$^{14}$)$_2$, where each R$^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; and each R$^{16}$ is alkyl, cycloalkyl, cycloalkylalkyl, aryl, aralkyl, heterocyclyl, heterocyclylalkyl, heteroaryl or heteroarylalkyl.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms or two to six carbon atoms, e.g., ethenylene, propenylene, n-butenylene, and the like. Unless stated otherwise specifically in the specification, an alkenylene chain may be optionally substituted by one or more of the following groups: alkyl, alkenyl, halo, cyano, aryl, cycloalkyl, heterocyclyl, heteroaryl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$), —S—, —S(O)$_t$OR$^{16}$, —S(O)$_t$R$^{16}$, and —S(O)$_t$N(R$^{14}$)$_2$, where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, cycloalkyl, cycloalkylalkyl, aryl, aralkyl, heterocyclyl, heterocyclylalkyl, heteroaryl or heteroarylalkyl.

"Alkynylene" and "Alkynylene chain" refer to a straight or branched divalent hydrocarbon chain linking the rest of the molecule to a radical group, consisting solely of carbon and hydrogen, containing at least one triple bond and having from two to twelve carbon atoms or two to six carbon atoms, e.g. propynylene, n butynylene, and the like. Unless stated otherwise specifically in the specification, an alkynylene chain may be optionally substituted by one or more of the following groups: alkyl, alkenyl, halo, cyano, aryl, cycloalkyl, heterocyclyl, heteroaryl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$), —S—, —S(O)$_t$OR$^{16}$, —S(O)$_t$R$^{16}$, and —S(O)$_t$N(R$^{14}$)$_2$, where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, cycloalkyl, cycloalkylalkyl, aryl, aralkyl, heterocyclyl, heterocyclylalkyl, heteroaryl or heteroarylalkyl.

"Alkoxy" refers to a radical of the formula —OR$_a$ where R$_a$ is an alkyl radical as generally defined above. The alkyl part of the alkoxy radical may be optionally substituted as defined above for an alkyl radical.

"Alkoxyalkyl" refers to a radical of the formula —R$_a$—O—R$_a$ where each R$_a$ is independently an alkyl radical as defined above. The oxygen atom may be bonded to any carbon in either alkyl radical. Each alkyl part of the alkoxyalkyl radical may be optionally substituted as defined above for an alkyl group.

"Aryl" refers to aromatic monocyclic or multicyclic hydrocarbon ring system consisting only of hydrogen and carbon and containing from 6 to 19 carbon atoms, preferably 6 to 10 carbon atoms, where the ring system may be partially saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, alkynyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—N(R$^{14}$)C(O)OR$^{16}$, —R$^{15}$—N(R$^{14}$)C(O)R$^{16}$, —$^{15}$—N(R$^{14}$)(S(O)$_t$R$^{16}$), —R$^{15}$—S(O)$_t$OR$^{16}$, —R$^{15}$—SR$^{16}$, —R$^{15}$—S(O)$_t$R$^{16}$, and —R$^{15}$—S(O)$_t$N(R$^{14}$)$_2$, where each R$^{14}$ is independently hydrogen, alkyl, haloalkyl, trifluoromethyl, cycloalkyl, cycloalkylalkyl, aryl, aralkyl, heterocyclyl, heterocyclylalkyl, heteroaryl, or heteroarylalkyl; each R$^{15}$ is independently a direct bond or a straight or branched alkylene or alkenylene chain; and each R$^{16}$ is alkyl, trifluoromethyl, cycloalkyl, cycloalkylalkyl, aryl, aralkyl, heterocyclyl, heterocyclylalkyl, heteroaryl, or heteroarylalkyl.

"Aralkyl" refers to a radical of the formula —R$_a$R$_b$ where R$_a$ is an alkyl radical as defined above and R$_b$ is one or more aryl radicals as defined above, e.g., benzyl, diphenylmethyl and the like. The aryl part of the aralkyl radical may be optionally substituted as described above for an aryl group. The alkyl part of the aralkyl radical may be optionally substituted as defined above for an alkyl group.

"Aryloxy" refers to a radical of the formula —OR$_b$ where R$_b$ is an aryl group as defined above. The aryl part of the aryloxy radical may be optionally substituted as defined above.

"Cycloalkyl" refers to a stable non-aromatic monocyclic or bicyclic hydrocarbon radical consisting solely of carbon and hydrogen atoms, having from three to fifteen carbon atoms, preferably having from three to twelve carbon atoms or from three to seven atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from the group consisting of alkyl, alkenyl, alkynyl, halo, haloalkyl, cyano, nitro, oxo, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$, —$R^{15}$—$N(R^{14})_2$, —$R^{15}$—$C(O)R^{14}$, —$R^{15}$—C(O)$OR^{14}$, —$R^{15}$—C(O)$N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$, —$R^{15}$—$S(O)_tOR^{16}$, —$R^{15}$—$SR^{16}$, —$R^{15}$—$S(O)_tR^{16}$, and —$R^{15}$—$S(O)_tN(R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl, or heteroarylalkyl.

"Cycloalkylalkyl" refers to a radical of the formula —$R_aR_d$ where $R_a$ is an alkyl radical as defined above and $R_d$ is a cycloalkyl radical as defined above. The cycloalkyl part of the cycloalkyl radical may be optionally substituted as defined above for a cycloalkyl radical. The alkyl part of the cycloalkyl radical may be optionally substituted as defined above for an alkyl radical.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, and the like. The alkyl part of the haloalkyl radical may be optionally substituted as defined above for an alkyl group.

"Heterocyclyl" refers to a stable 3- to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic or tricyclic ring system, which may include fused or bridged ring systems, which may be partially unsaturated; and the nitrogen, carbon or sulfur atoms in the heterocyclyl radical may be optionally oxidized; the nitrogen atom may be optionally alkylated/substituted; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl, homopiperidinyl, homopiperazinyl, and quinuclidinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$, —$R^{15}$—$N(R^{14})_2$, —$R^{15}$—$C(O)R^{14}$, —$R^{15}$—C(O)$OR^{14}$, —$R^{15}$—C(O)$N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$, —$R^{15}$—$S(O)_tOR^{16}$, —$R^{15}$—$SR^{16}$, —$R^{15}$—$S(O)_tR^{16}$, and —$R^{15}$—$S(O)_tN(R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl, or heteroarylalkyl, and where each of the above substituents is unsubstituted.

"Heterocyclylalkyl" refers to a radical of the formula —$R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at either a nitrogen or carbon atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Heteroaryl" refers to a 5- to 18-membered aromatic ring radical which consists of carbon atoms and from one to five heteroatoms selected from the group consisting of nitrogen, oxygen and sulfur. For purposes of this invention, the heteroaryl radical may be a monocyclic, bicyclic or tricyclic ring system, which may include fused or bridged ring systems, which may be partially saturated; and the nitrogen, carbon or sulfur atoms in the heteroaryl radical may be optionally oxidized; the nitrogen atom may be optionally alkylated/substituted. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl, benzothiophenyl, benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, alkynyl, alkoxy, halo, haloalkyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$, —$R^{15}$—$N(R^{14})_2$, —$R^{15}$—$C(O)R^{14}$, —$R^{15}$—C(O)$OR^{14}$, —$R^{15}$—C(O)$N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$, —$R^{15}$—$S(O)_tOR^{16}$, —$R^{15}$—$SR^{16}$, —$R^{15}$—$S(O)_tR^{16}$, and —$R^{15}$—$S(O)_tN(R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl, or heteroarylalkyl.

"Heteroarylalkyl" refers to a radical of the formula —$R_aR_f$ where $R_a$ is an alkyl radical as defined above and $R_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Hydroxyalkyl" refers to a radical of the formula —$R_a$—OH where $R_a$ is an alkyl radical as defined above. The hydroxy group may be attached to the alkyl radical on any carbon within the alkyl radical. The alkyl part of the hydroxyalkyl group may be optionally substituted as defined above for an alkyl group.

"A multiring structure" refers to a multicyclic ring system comprised of two to four rings wherein the rings are independently selected from cycloalkyl, aryl, heterocyclyl or heteroaryl as defined above. Each cycloalkyl may be optionally substituted as defined above for a cycloalkyl group. Each aryl may be optionally substituted as defined above for an aryl group. Each heterocyclyl may be optionally substituted as defined above for a heterocyclyl group. Each heteroaryl may be optionally substituted as defined above for a heteroaryl group. The rings may be attached to each other through direct bonds or some or all of the rings may be fused to each other.

"Prodrugs" is meant to indicate a compound that may be converted under physiological conditions or by solvolysis to a biologically active compound of the invention. Thus, the term "prodrug", refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood or conversion in the gut or liver. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, Anglican Pharmaceutical Association arid Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto or acid group is bonded to any group that, when the prodrug of the compound of the invention is administered to a mammalian subject, cleaves to form a free hydroxy, free amino or free mercapto or acid group, respectively. Examples of prodrugs include, but are not limited to, acetate, formate and benzoate derivatives of alcohol or amides of amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent. A skilled artisan will recognize unstable combinations of substituents.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphorirc acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients thereof.

"Therapeutically effective amount" refers to that amount of a compound of the invention which, when administered to a mammal, preferably a human, is sufficient to effect treatment, as defined below, of an SCD-mediated disease or condition in the mammal, preferably a human. The amount of a compound of the invention which constitutes a "therapeutically effective amount" will vary depending on the compound, the condition and its severity, and the age and body weight of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes: (i) preventing the disease or condition from occurring in a mammal, in particular, when such mammal is predisposed to the condition but has not yet been diagnosed as having it; (ii) inhibiting the disease or condition, i.e., arresting its development; or (iii) relieving the disease or condition, i.e., causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

Also within the scope of the invention are intermediate compounds of formula (I) and all polymorphs of the aforementioned species and crystal habits thereof.

The chemical naming protocol and structure diagrams used herein employ and rely on the chemical naming features as utilized by ISIS Draw version 2.5 (available from MDL Information Systems, Inc.).

EMBODIMENTS OF THE INVENTION

One embodiment of the invention is the compounds of formula (I):

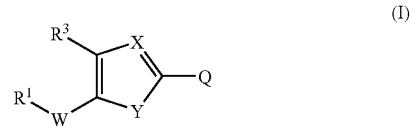

wherein,
X is N or CH;
Y is NH, O, S or N—CH$_3$;
Q is

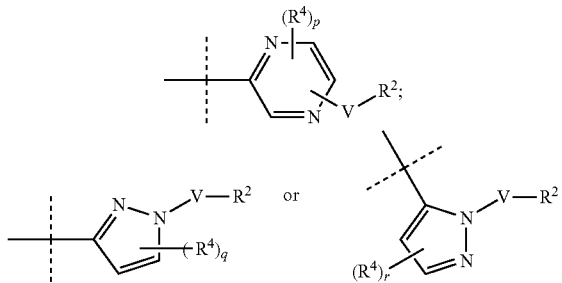

wherein when Q is

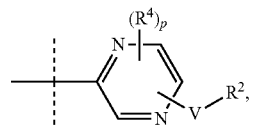

W is selected from —N(R$^6$)C(O)—, —C(O)N(R$^6$)—, —OC(O)N(R$^6$)—, —N(R$^6$)C(O)O—, —N(R$^6$)C(O)N(R$^6$)—, —O—, —N(R$^6$)—, —S—, —S(O)$_t$—, —N(R$^6$)S(O)$_t$—, —S(O)$_t$N(R$^6$)—, —OS(O)$_t$N(R$^6$)—, —C(O)—, —OC(O)—, —C(O)O—, —N(R$^6$)C(=N(R$^{6a}$))N(R$^6$)—, —N(R$^6$)((R$^{6a}$)N=)C—, —C(=N(R$^{6a}$))N(R$^6$)—, an aryl, a heteroaryl, a heterocyclyl, an alkynylene, an alkenylene, an alkylene or a direct bond;
V is selected from —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —N(R$^5$)—, —S—, —S(O)$_t$—, —N(R$^5$)S(O)$_2$—, —S(O)$_2$N(R$^5$)—, —OS(O)$_2$N(R$^5$)—, —C(O)—, —OC(O)—, —C(O)O—, —CR$^5$C(O)N(R$_5$)—, —(CR$^5{}_2$)$_n$C(O)—, —(CR$^5{}_2$)$_n$O—, —(CR$^5{}_2$)$_n$N(R$^6$)—, —(CR$^5{}_2$)$_n$N(R$^5$)C(O)—, —(CR$^5{}_2$)$_n$N(R$^5$)C(O)O—, —(CR$^5{}_2$)$_n$N(R$^5$)S(O)$_t$—, —N(R$^5$)C(=N(R$^{5a}$))NR$^5$—, —N(R$^5$)((R$^{5a}$)N=)C—, —C(=N(R$^{5a}$))N(R$^5$)—, —(CR$^5$)$_n$CR$^5$=CR$^5$—, an alkynylene, an alkenylene, an alkynyl, an alkylene or a direct bond;
t is 1 or 2;
p is 0, 1, or 2;
n is 1 to 6;
R$^1$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
or R$^1$ is a multi-ring structure having 2 to 4 rings wherein the rings are independently selected from the group consisting of cycloalkyl, heterocyclyl, aryl and heteroaryl and where some or all of the rings may be fused to each other;
R$^2$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
or R$^2$ is a multi-ring structure having 2 to 4 rings wherein the rings are independently selected from the group consisting of cycloalkyl, heterocyclyl, aryl and heteroaryl and where some or all of the rings may be fused to each other;
R$^3$ is selected from the group consisting of hydrogen, alkyl, alkenyl, alkynyl, hydroxyalkyl, alkoxyalkyl, cycloalkyl, cycloalkylalkyl, heterocyclyl, aryl, aralkyl, heteroaryl, halo, trifluoromethyl, trifluoromethoxyl, cyano and —N(R$^6$)$_2$;
R$^4$ is selected from the group consisting of alkyl, halo, —N(R$^6$)$_2$, haloalkyl, hydroxyl, alkoxy, —N(R$^2$)$_2$, cycloalkylalkyl and aralkyl;
R$^5$ and R$^6$ are independently selected from the group consisting of hydrogen, alkyl, halo, aryl, heteroaryl, cycloalkyl, hydroxyalkyl, cycloalkylalkyl and aralkyl;
R$^{5a}$ and R$^{6a}$ are independently selected from the group consisting of hydrogen, alkyl, cycloalkylalkyl and cyano;
and
wherein when Q is

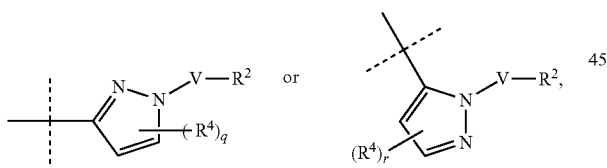

W is selected from —N(R$^6$)C(O)—, —C(O)N(R$^6$)—, —OC(O)N(R$^6$)—, —N(R$^6$)C(O)O—, —N(R$^6$)C(O)N(R$^6$)—, —O—, —N(R$^6$)—, —S—, —S(O)$_t$—, —N(R$^6$)S(O)$_t$—, —S(O)$_t$N(R$^6$)—, —OS(O)$_t$N(R$^6$)—, —C(O)—, —OC(O)—, —C(O)O—, —N(R$^6$)C(=N(R$^{6a}$))N(R$^6$)—, —N(R$^6$)((R$^{6a}$)N=)C—, —C(=N(R$^{6a}$))N(R$^6$)—, an aryl, a heteroaryl, a heterocyclyl, an alkynylene, an alkenylene, an alkylene or a direct bond;
V is selected from —C(O)N(R$^5$)—, —S(O)$_t$—, —S(O)$_2$N(R$^5$)—, —C(O)—, —C(O)O—, —C(O)N(R$^5$)—, —CR$^5{}_2$C(O)N(R$^5$)—, —(CR$^5{}_2$)$_n$C(O)—, —(CR$^5{}_2$)$_n$O—, —(CR$^5{}_2$)$_n$N(R$^6$)—, —(CR$^5{}_2$)$_n$N(R$^5$)C(O)—, —(CR$^5{}_2$)$_n$N(R)C(O)O—, —(CR$^5{}_2$)$_n$N(R$^5$)S(O)$_t$—, an aryl, a heteroaryl, a heterocyclyl, an alkynylene, an alkenylene, an alkylene or a direct bond;
t is 1 or 2;
q is 0, 1, or 2;
r is 0, 1 or 2;
n is 1 to 6;
R$^1$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
or R$^1$ is a multiring structure having 2 to 4 rings wherein the rings are independently selected from the group consisting of cycloalkyl, heterocyclyl, aryl and heteroaryl and where some or all of the rings may be fused to each other;
R$^2$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
or R$^2$ is a multiring structure having 2 to 4 rings wherein the rings are independently selected from the group consisting of cycloalkyl, heterocyclyl, aryl and heteroaryl and where some or all of the rings may be fused to each other;
R$^3$ is selected from the group consisting of hydrogen, alkyl, alkenyl, alkynyl, hydroxyalkyl, alkoxyalkyl, cycloalkyl, cycloalkylalkyl, heterocyclyl, aryl, aralkyl, heteroaryl, halo, trifluoromethyl, trifluoromethoxyl, cyano and —N(R$^6$)$_2$;
R$^4$ is selected from the group consisting of alkyl, haloalkyl, hydroxyl, alkoxy, —N(R$^2$)$_2$, cycloalkylalkyl and aralkyl;
R$^5$ and R$^6$ are independently selected from the group consisting of hydrogen, alkyl, halo, aryl, heteroaryl, cycloalkyl, hydroxyalkyl, cycloalkylalkyl and aralkyl;
R$^{5a}$ and R$^{6a}$ are independently selected from the group consisting of hydrogen, alkyl, cycloalkylalkyl and cyano; or
as a stereoisomer, enantiomer or tautomer thereof, a pharmaceutically acceptable salt thereof, a pharmaceutical composition thereof or a prodrug thereof.

A more preferred embodiment is a compound of formula (I), wherein:
Q is

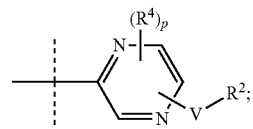

V is selected from aryl, —N(R$^5$)—, —O—, an alkylene or a direct bond;
W is selected from —N(R$^6$)C(O)—, —C(O)N(R$^6$)—, —C(O)O— or a direct bond;
X is N or CH;
Y is S;
p is 0, 1 or 2;
R$^1$ is selected from the group consisting of hydrogen, alkyl, aryl, aralkyl, cycloalkyl, cycloalkylalkyl, heterocyclyl, heterocyclylalkyl, heteroaryl and heteroarylalkyl;
R$^2$ is selected from the group consisting of hydrogen, alkyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
R$^3$ is hydrogen or alkyl; and
R$^6$ is hydrogen or alkyl.

A more preferred embodiment is a compound of formula (I), wherein:

Q is

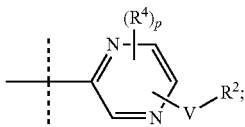

V is selected from aryl, —N(R$^5$)—, an alkylene or a direct bond;
W is selected from —N(R$^6$)C(O)— or —C(O)O—;
X is N or CH;
Y is S;
p is 0, 1 or 2;
R$^1$ is selected from the group consisting of alkyl, aryl, aralkyl, cycloalkylalkyl, heterocyclyl, heterocyclylalkyl and heteroarylalkyl;
R$^2$ is selected from the group consisting of hydrogen, alkyl, hydroxyalkyl, alkoxyalkyl, cycloalkyl, cycloalkylalkyl, aryl and aralkyl;
R$^3$ is hydrogen or alkyl; and
R$^6$ is hydrogen or alkyl.

A more preferred embodiment is a compound of formula (I), wherein:

Q is

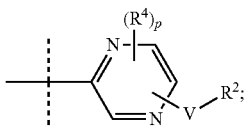

V is a an alkylene or a direct bond;
W is —N(R$^6$)C(O)—;
X is N or CH;
Y is S;
p is 0, 1 or 2;
R$^1$ is selected from the group consisting of alkyl, aryl, aralkyl, and heteroaryl;
R$^2$ is selected from the group consisting of alkyl, hydroxyalkyl, alkoxyalkyl, cycloalkyl, cycloalkylalkyl, aryl and aralkyl;
R$^3$ is alkyl; and
R$^6$ is hydrogen.

A more preferred embodiment is a compound of formula (I), wherein:

Q is

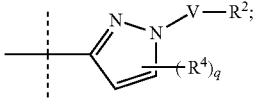

V is selected from —(CR$^5_2$)$_n$O—, aryl, alkylene or a direct bond;
W is selected from —N(R$^6$)C(O)—, —C(O)N(R$^6$)—, —C(O)O— or a direct bond;
X is N or CH;
Y is S;
q is 0, 1, or 2;
R$^1$ is selected from the group consisting of hydrogen, alkyl, aryl, aralkyl, cycloalkyl, cycloalkylalkyl, heterocyclyl, heterocyclylalkyl, heteroaryl and heteroarylalkyl;
R$^2$ is selected from the group consisting of hydrogen, alkyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
R$^3$ is hydrogen or alkyl;
R$^5$ is hydrogen or alkyl; and
R$^6$ is hydrogen or alkyl.

A more preferred embodiment is a compound of formula (I), wherein:

Q is

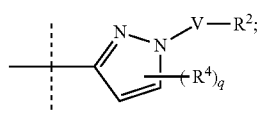

V is selected from —(CR$^5_2$)$_n$O—, aryl, alkylene or a direct bond;
W is selected from —N(R$^6$)C(O)— or —C(O)O—;
X is N or CH;
Y is S;
q is 0, 1, or 2;
R$^1$ is selected from the group consisting of alkyl, aryl, aralkyl, cycloalkylalkyl, heterocyclyl, heterocyclylalkyl and heteroarylalkyl;
R$^2$ is selected from the group consisting of hydrogen, alkyl, hydroxyalkyl, alkoxyalkyl, cycloalkyl, cycloalkylalkyl, aryl and aralkyl;
R$^3$ is hydrogen or alkyl;
R$^5$ is hydrogen or alkyl; and
R$^6$ is hydrogen or alkyl.

A more preferred embodiment is a compound of formula (I), wherein:

Q is

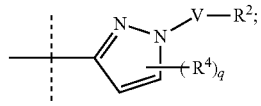

V is —(CR$^5_2$)$_n$O— or a direct bond;
W is —N(R$^6$)C(O)—;
X is N or CH:
Y is S;
q is 0, 1, or 2;
R$^1$ is selected from, the group consisting of alkyl, aryl, aralkyl and heteroaryl
R$^2$ is selected from the group consisting of alkyl, hydroxyalkyl, alkoxyalkyl, cycloalkyl, cycloalkylalkyl, aryl and aralkyl;
R$^3$ is alkyl; and
R$^6$ is hydrogen.

A more preferred embodiment is a compound of formula (I), wherein:
Q is

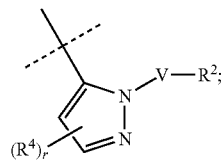

V is selected from —(CR$^5_2$)$_n$O—, aryl, alkylene or a direct bond;
W is selected from —N(R$^6$)C(O)—, —C(O)N(R$^6$)—, —C(O)O— or a direct bond;
X is N or CH;
Y is S;
r is 0, 1 or 2;
R$^1$ is selected from the group consisting of hydrogen, alkyl, aryl, aralkyl, cycloalkyl, cycloalkylalkyl, heterocyclyl, heterocyclylalkyl, heteroaryl and heteroarylalkyl;
R$^2$ is selected from the group consisting of hydrogen, alkyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
R$^3$ is hydrogen or alkyl;
R$^5$ is hydrogen or alkyl; and
R$^6$ is hydrogen or alkyl.

In one embodiment, the methods of the invention are directed towards the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, cardiovascular disease, diabetes, obesity, metabolic syndrome, dermatological disorders and the like by administering an effective amount of a compound of the invention.

The present invention also relates to pharmaceutical composition containing the compounds of the invention. In one embodiment, the invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

Utility and Testing of the Compounds of the Invention

The present invention relates to compounds, pharmaceutical compositions and methods of using the compounds and pharmaceutical compositions for the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, especially cardiovascular disease, diabetes, obesity, metabolic syndrome, dermatological disorders and the like, by administering to a patient in need of such treatment an effective amount of an SCD modulating, especially inhibiting, agent.

In general, the present invention provides a method for treating a patient for, or protecting a patient from developing, a disease related to dyslipidemia and/or a disorder of lipid metabolism, wherein lipid levels in an animal, especially a human being, are outside the normal range (i.e., abnormal lipid level, such as elevated plasma lipid levels), especially levels higher than normal, preferably where said lipid is a fatty acid, such as a free or complexed fatty acid, triglycerides, phospholipids, or cholesterol, such as where LDL-cholesterol levels are elevated or HDL-cholesterol levels are reduced, or any combination of these, where said lipid-related condition or disease is an SCD-mediated disease or condition, comprising administering to an animal, such as a mammal, especially a human patient, a therapeutically effective amount of a compound of the invention or a pharmaceutical composition comprising a compound of the invention wherein the compound modulates the activity of SCD, preferably human SCD1.

The compounds of the invention modulate, preferably inhibit, the activity of human SCD enzymes, especially human SCD1.

The general value of the compounds of the invention in modulating, especially inhibiting, the activity of SCD can be determined using the assay described below in Example 97.

Alternatively, the general value of the compounds in treating disorders and diseases may be established in industry standard animal models for demonstrating the efficacy of compounds in treating obesity, diabetes or elevated triglyceride or cholesterol levels or for improving glucose tolerance. Such models include Zucker obese fa/fa rats (available from Harlan Sprague Dawley, Inc. (Indianapolis, Ind.)), or the Zucker diabetic fatty rat (ZDF/GmiCrl-fa/fa) (available from Charles River Laboratories (Montreal, Quebec)), and Sprague Dawley rats (Charles Rivers), as used in models for diet-induced obesity (Ghibaudi, L. et al., (2002), *Obes. Res.* Vol. 10, pp. 956-963). Similar models have also been developed for mice and Lewis rats.

The compounds of the instant invention are inhibitors of delta-9 desaturases and are useful for treating diseases and disorders in humans and other organisms, including all those human diseases and disorders which are the result of aberrant delta-9 desaturase biological activity or which may be ameliorated by modulation of delta-9 desaturase biological activity.

As defined herein, an SCD-mediated disease or condition is defined as any disease or condition in which the activity of SCD is elevated and/or where inhibition of SCD activity can be demonstrated to bring about symptomatic improvements for the individual so treated. As defined herein, an SCD-mediated disease or condition includes, but is not limited to, a disease or condition which is, or is related to, cardiovascular disease, dyslipidemias (including but not limited to disorders of serum levels of triglycerides, hypertriglyceridemia, VLDL, HDL, LDL, fatty acid Desaturation Index (e.g. the ratio of 18:1/18:0 fatty acids, or other fatty acids, as defined elsewhere herein), cholesterol, and total cholesterol, hypercholesterolemia, as well as cholesterol disorders (including disorders characterized by defective reverse cholesterol transport)), familial combined hyperlipidemia, coronary artery disease, atherosclerosis, heart disease, cerebrovascular disease (including but not limited to stroke, ischemic stroke and transient ischemic attack (TIA)), peripheral vascular disease, and ischemic retinopathy.

An SCD-mediated disease or condition also includes metabolic syndrome (including but not limited to dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia and anorexia), weight loss, body mass index and leptin-related diseases. In a preferred embodiment, compounds of the invention will be used to treat diabetes mellitus and/or obesity.

As used herein, the term "metabolic syndrome" is a recognized clinical term used to describe a condition comprising Combinations of Type II diabetes, impaired glucose tolerance, insulin resistance, hypertension, obesity, increased abdominal girth, hypertriglyceridemia, low HDL, hyperuricaemia, hypercoagulability and/or microalbuminemia. The American Heart Association has published guidelines for the diagnosis of metabolic syndrome, Grundy, S., et al., (2006) *Cardiol. Rev.* Vol. 13, No. 6, pp. 322-327.

An SCD-mediated disease or condition also includes fatty liver, hepatic steatosis, hepatitis, non-alcoholic hepatitis, non-alcoholic steatohepatitis (NASH), alcoholic hepatitis, acute fatty liver, fatty liver of pregnancy, drug-induced hepatitis, erythrohepatic protoporphyria, iron overload disorders, hereditary hemochromatosis, hepatic fibrosis, hepatic cirrhosis, hepatoma and conditions related thereto.

An SCD-mediated disease or condition also includes but is not limited to a disease or condition which is, or is related to primary hypertriglyceridemia, or hypertriglyceridemia secondary to another disorder or disease, such as hyperlipoproteinemias, familial histiocytic reticulosis, lipoprotein lipase deficiency, apolipoprotein deficiency (such as ApoCII deficiency or ApoE deficiency), and the like, or hypertriglyceridemia of unknown or unspecified etiology.

An SCD-mediated disease or condition also includes a disorder of polyunsaturated fatty acid (PUPA) disorder, or a skin disorder, including but not limited to eczema, acne, psoriasis, keloid scar formation or prevention, diseases related to production or secretions from mucous membranes, such as monounsaturated fatty acids, wax esters, and the like. Preferably, the compounds of the invention will prevent or attenuate keloid scar formation by reduction of excessive sebum production that typically results in their formation.

An SCD-mediated disease or condition also includes inflammation, sinusitis, asthma, pancreatitis, osteoarthritis, rheumatoid arthritis, cystic fibrosis, and premenstrual syndrome.

An SCD-mediated disease or condition also includes but is not limited to a disease or condition which is, or is related to cancer, neoplasia, malignancy, metastases, tumors (benign or malignant), carcinogenesis, hepatomas and the like.

An SCD-mediated disease or condition also includes a condition where increasing lean body mass or lean muscle mass is desired, such as is desirable in enhancing performance through muscle building. Myopathies and lipid myopathies such as carnitine palmitoyltransferase deficiency (CPT I or CPT II) are also included herein. Such treatments are useful, in humans and in animal husbandry, including for administration to bovine, porcine or avian domestic animals or any other animal to reduce triglyceride production and/or provide leaner meat products and/or healthier animals.

An SCD-mediated disease or condition also includes a disease or condition that is, or is related to, psychiatric disorders, multiple sclerosis, eye diseases, and immune disorders.

An SCD-mediated disease or condition also includes neurological diseases, including mild cognitive impairment, depression, schizophrenia, obsessive-compulsive disorder, and biopolar disorder.

An SCD-mediated disease or condition also includes neurodegenerative diseases, including Alzheimer's disease, Parkinson's disease, dementia with Lewy bodies, amyotrophic lateral sclerosis or Lou Gehrig's disease, Alpers' disease, Leigh's disease, Pelizaeus-Merzbacher disease, Olivopontocerebellar atrophy, Friedreich's ataxia, leukodystrophies, Rett syndrome, Ramsay Hunt syndrome type II, and Down's syndrome.

An SCD-mediated disease or condition also includes a disease or condition which or is related to, viral diseases or infections including but not limited to all positive strand RNA viruses, coronaviruses, SARS virus, SARS-associated coronavirus, Togaviruses, Picornaviruses, Coxsackievirus, Yellow Fever virus, Flaviviridae, ALPHAVIRUS (TOGAVIRIDAE) including Rubella virus, Eastern equine encephalitis virus, Western equine encephalitis virus, Venezuelan equine encephalitis virus, Sindbis virus, Semliki forest virus, Chikungunya virus, O'nyong'nyong virus, Ross river virus, Mayaro virus, Alphaviruses; ASTROVIRIDAE including Astrovirus, Human Astroviruses; CALICIVIRIDAE including Vesicular exanthema of swine virus, Norwalk virus, Calicivirus, Bovine calicivirus, Pig calcivirus, Hepatitis E; CORONAVIRIDAE including Coronavirus, SARS virus, Avian infectious bronchitis virus, Bovine coronavirus, Canine coronavirus, Feline infectious peritonitis virus, Human coronavirus 299E, Human coronavirus OC43, Murine hepatitis virus, Porcine epidemic diarrhea virus, Porcine hemagglutinating encephalomyelitis virus, Porcine transmissible gastroenteritis virus, Rat coronavirus, Turkey coronavirus, Rabbit coronavirus, Berne virus, Breda virus; FLAVIVIRIDAE including Hepatitis C virus, West Nile virus, Yellow Fever virus, St. Louis encephalitis virus, Dengue Group, Hepatitis G virus, Japanese B encephalitis virus, Murray Valley encephalitis virus, Central European tick-borne encephalitis virus, Far Eastern tick-borne encephalitis virus, Kyasanur forest virus, Louping ill virus, Powassan virus, Omsk hemorrhagic fever virus, Kumilinge virus, Absetarov anzalova hypr virus, Theus virus, Rocio encephalitis virus, Langat virus, Pestivirus, Bovine viral diarrhea, Hog cholera virus, Rio Bravo Group, Tyuleniy Group, Ntaya Group, Uganda S Group, Modoc Group; PICORNAVIRIDAE including Coxsackie A virus, Rhinovirus, Hepatitis A virus, Encephalomyocarditis virus, Mengovirus, ME virus, Human poliovirus 1, Coxsackie B; POCYVIRIDAE including Potyvirus, Rymovirus, Bymovirus. Additionally it can be a disease or infection caused by or linked to Hepatitis viruses, Hepatitis B virus, Hepatitis C virus, human immunodeficiency virus (HIV) and the like. Treatable viral infections include those where the virus employs an RNA intermediate as part of the replicative cycle (hepatitis or HIV); additionally it can be a disease or infection caused by or linked to RNA negative strand viruses such as influenza and parainfluenza viruses.

The compounds identified in the instant specification inhibit the desaturation of various fatty acids (such as the $C_9$-$C_{10}$ desaturation of stearoyl-CoA), which is accomplished by delta-9 desaturases, such as stearoyl-CoA desaturase 1 (SCD1). As such, these compounds inhibit the formation of various fatty acids and downstream metabolites thereof. This may lead to an accumulation of stearoyl-CoA or palmitoyl-CoA and other upstream precursors of various fatty acids; which may possibly result in a negative feedback loop causing an overall change in fatty acid metabolism. Any of these consequences may ultimately be responsible for the overall therapeutic benefit provided by these compounds.

Typically, a successful SCD inhibitory therapeutic agent will meet some or all of the following criteria. Oral availability should be at or above 20%. Animal model efficacy is less than about 10 mg/Kg, 2 mg/Kg, 1 mg/Kg, or 0.5 mg/Kg and the target human dose is between 10 and 250 mg/70 Kg, although doses outside of this range may be acceptable ("mg/ Kg" means milligrams of compound per kilogram of body mass of the subject to whom it is being administered). The required dosage should preferably be no more than about once or twice a day or at meal times. The therapeutic index (or ratio of toxic dose to therapeutic dose) should be greater than 10. The $IC_{50}$ ("Inhibitory Concentration –50%") is a measure of the amount of compound required to achieve 50% inhibition of SCD activity, over a specific time period, in an SCD biological activity assay. Any process for measuring the activity of SCD enzymes, preferably mouse or human SCD enzymes, may be utilized to assay the activity of the compounds useful in the methods of the invention in inhibiting said SCD activity. Compounds of the invention demonstrate an $IC_{50}$ ("Inhibitory Concentration of 50%") in a 15 minute microsomal assay of preferably less than 10 μM, less than 5 μM, less than 2.5 μM, less than 1 μM, less than 750 nM, less than 500 nM, less than 250 nM, less than 100 nM, less than, 50 nM, and most preferably less than 20 nM. Compounds of the invention may show reversible inhibition (i.e., competitive inhibition) and preferably do not inhibit other iron binding proteins.

The identification of compounds of the invention as SCD inhibitors was readily accomplished using the SCD enzyme and microsomal assay procedure described in Shanklin J. and Summerville C., *Proc. Natl. Acad. Sci. USA* (1991), Vol. 88, pp. 2510-2514. When tested in this assay, compounds of the invention had less than 50% remaining SCD activity at 10 μM concentration of the test compound, preferably less than 40% remaining SCD activity at 10 μM concentration of the test compound, more preferably less than 30% remaining SCD activity at 10 μM concentration of the test compound, and even more preferably less than 20% remaining SCD activity at 10 μM concentration of the test compound, thereby demonstrating that the compounds of the invention are potent inhibitors of SCD activity.

These results provide the basis for analysis of the structure-activity relationship (SAR) between test compounds and SCD. Certain-groups tend to provide more potent inhibitory compounds. SAR analysis is one of the tools those skilled in the art may employ to identify preferred embodiments of the compounds of the invention for use as therapeutic agents. Other methods of testing the compounds disclosed herein are also readily available to those skilled in the art. Thus, in addition, the determination of the ability of a compound to inhibit SCD may be accomplished in vivo. In one such embodiment this is accomplished by administering said chemical agent to an animal afflicted with a triglyceride (TG)- or very low density lipoprotein (VLDL)-related disorder and subsequently detecting a change in plasma triglyceride level in said animal thereby identifying a therapeutic agent useful in treating a triglyceride (-TG)- or very low density lipoprotein (VLDL)-related disorder. In such embodiment, the animal may be a human, such as a human patient afflicted with such a disorder and in need of treatment of said disorder.

In specific embodiments of such in vivo processes, said change in SCD1 activity in said animal is a decrease in activity, preferably wherein said SCD1 modulating agent does not substantially inhibit the biological activity of a delta-5 desaturase, delta-6 desaturase or fatty acid synthetase or other enzymes containing iron at the active site.

The model systems useful for compound evaluation may include, but are not limited to, the use of liver microsomes, such as from mice that have been maintained on a high carbohydrate diet, or from human donors, including persons suffering from obesity. Immortalized cell lines, such as HepG2 (from human liver), MCF-7 (from human breast cancer) and 3T3-L1 (from mouse adipocytes) may also be used. Primary cell lines, such as mouse primary hepatocytes, are also useful in testing the compounds of the invention. Where whole animals are used, mice used as a source of primary hepatocyte cells may also be used wherein the mice have been maintained on a high carbohydrate diet to increase SCD activity in mirocrosomes and/or to elevate plasma triglyceride levels (i.e., the 18:1/18:0 ratio); alternatively mice on a normal diet or mice with normal triglyceride levels may be used. Mouse models employing transgenic mice designed for hypertriglyceridemia are also available. Rabbits and hamsters are also useful as animal models, especially those expressing CETP (cholesterol ester transfer protein).

Another suitable method for determining the in vivo efficacy of the compounds of the invention is to indirectly measure their impact on inhibition of SCD enzyme by measuring a subject's Desaturation Index after administration of the compound.

"Desaturation Index" as employed in this specification means the ratio of the product over the substrate for the SCD enzyme as measured from a given tissue sample. This value may be calculated using three different equations 18:1n-9/ 18:0 (oleic acid over stearic acid); 16:1n-7/16:0 (palmitoleic acid over palmitic acid); and/or 16:1n-7+18:1n-7/16:0 (measuring all reaction products of 16:0 desaturation over 16:0 substrate).

Desaturation Index is primarily measured in liver or plasma triglycerides, but may also be measured in other selected lipid fractions from a variety of tissues. Desaturation Index, generally speaking, is a tool for plasma lipid profiling.

A number of human diseases and disorders are the result of aberrant SCD1 biological activity and may be ameliorated by modulation of SCD1 biological activity using the therapeutic agents of the invention.

Inhibition of SCD expression may also affect the fatty acid composition of membrane phospholipids, as well as production or levels of triglycerides and cholesterol esters. The fatty acid composition of phospholipids ultimately determines membrane fluidity, with a subsequent modulation of the activity of multiple enzymes present within the membrane, while the effects on the composition of triglycerides and cholesterol esters can affect lipoprotein metabolism and adiposity.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented.

For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as, elevated triglycerides or cholesterol, before administration of said compound of the invention and the compound of the invention is present in an amount effective to reduce said lipid level.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

Those skilled in the art are familiar with how to determine suitable doses of the compounds for use in treating the diseases and disorders contemplated herein.

Therapeutic doses are generally identified through a dose ranging study in humans based on preliminary evidence derived from animal studies. Doses must be sufficient to result in a desired therapeutic benefit without causing unwanted side effects for the patient. The preferred dosage range for an animal is 0.001 mg/Kg to 10,000 mg/Kg, including 0.5 mg/Kg, 1.0 mg/Kg, 2.0 mg/Kg, 5.0 mg/Kg and 10 mg/Kg, though doses outside this range may be acceptable. The dosing schedule may be once or twice per day, although more often or less often may be satisfactory.

Those skilled in the art are also familiar with determining administration methods (oral, intravenous, inhalation, subcutaneous, transdermal (topical), etc.), dosage forms, suitable pharmaceutical excipients and other matters relevant to the delivery of the compounds to a subject in need thereof.

In an alternative use of the invention, the compounds of the invention can be used in vitro or in vivo studies as exemplary agents for comparative purposes to find other compounds also useful in treatment of, or protection from, the various diseases disclosed herein.

The pharmaceutical compositions according to the invention are those suitable for enteral, such as oral or rectal, transdermal and parenteral administration to mammals, including man, to inhibit stearoyl-CoA desaturase, and for the treatment of conditions associated with stearoyl desaturase activity. In general, the pharmaceutical compositions comprise a therapeutically effective amount of a pharmacologically active compound of the instant invention, alone or in combination with one or more pharmaceutically acceptable carriers.

The pharmacologically active compounds of the invention are useful in the manufacture of pharmaceutical compositions comprising a therapeutically effective amount thereof in conjunction or admixture with excipients or carriers suitable for either enteral or parenteral application. For enteral or parenteral application, it is preferred to administer an effective amount of a pharmaceutical composition according to the invention as tablets or gelatin capsules. Such pharmaceutical compositions may comprise, for example, the active ingredient together with diluents (e.g., lactose, dextrose, sucrose, mannitol, sorbitol, cellulose and/or glycine), lubricants (e.g., silica, talcum, stearic acid, its magnesium or calcium salt and/or polyethyleneglycol), and for tablets also comprises binders (e.g., magnesium aluminum silicate, starch paste, gelatin, tragacanth, methylcellulose, sodium carboxymethylcellulose and/or polyvinylpyrrolidone) and disintegrants (e.g., starches, agar, alginic acid or its sodium salt) or effervescent mixtures and absorbants, colorants, flavors and sweeteners.

In another aspect of the present invention the compounds may be in the form of injectable compositions, e.g. preferably aqueous isotonic solutions or suspensions, and suppositories, which can be advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions may be prepared according to conventional mixing, granulating or coating methods, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate-controlling barrier to deliver the compound of the skin of the host at a controlled and pre-determined rate over a prolonged period of time, and means to secure the device to the skin.

The most suitable route will depend on the nature and severity of the condition being treated. Those skilled in the art are also familiar with determining administration methods, dosage forms, suitable pharmaceutical excipients and other matters relevant to the delivery of the compounds to a subject in need thereof.

The compounds of the invention may be usefully combined with one or more other therapeutic agents for the treatment of SCD-mediated diseases and conditions. Preferably, the other therapeutic agent is selected from antidiabetics, hypolipidemic agents, anti-obesity agents, anti-hypertensive agents or inotropic agents.

Thus, an additional aspect of the present invention concerns a pharmaceutical composition comprising a therapeutically effective amount of a compound of the invention in combination with one or more other therapeutic agents. For example, the composition can be formulated to comprise a therapeutically effective amount of a compound of the invention as defined above, in combination with another therapeutic agent, each at an effective therapeutic dose as reported in the art. Such therapeutic agents may, for example, include insulin, insulin derivatives and mimetics; insulin secretagogues, such as the sulfonylureas, e.g., Glipizide, glyburide and Amaryl; insulinotropic sulfonylurea receptor ligands, such as meglitinides, e.g., nateglinide and repaglinide; PPARγ and/or PPARα (peroxisome proliferator-activated receptor) ligands such as MCC-555, MK767, L-165041, GW7282 or thiazolidinediones such as rosiglitazone, pioglitazone, troglitazone; insulin sensitizers, such as protein tyrosine phosphatase-1B (PTP-1B) inhibitors such as PTP-112; GSK3 (glycogen synthase kinase-3) inhibitors such as SB-517955, SB-4195052, SB-216763, NN-57-05441, NN-57-05445 or RXR ligands such as GW-0791, AGN-194204; sodium-dependent glucose cotransporter inhibitors, such as T-1095, glycogen phosphorylase A inhibitors, such as BAY R3401; biguanides, such as metformin; alpha-glucosidase inhibitors, such as acarbose; GLP-1 (glucagon like peptide-1), GLP-1 analogs, such as Exendin-4, and GLP-1 mimetics; DPPIV (dipeptidyl peptidase IV) inhibitors such as LAF237 (Vildagliptin); hypolipidemic agents, such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin, fluindostatin and rivastatin, squalene synthase inhibitors or FXR (farnesoid X receptor) and LXR (liver X receptor) ligands, cholestyramine, fibrates, nicotinic acid and aspirin; anti-obesity agents, such as orlistat, anti-hypertensive agents, inotropic agents and hypolipidemic agents, e.g., loop diuretics, such as ethacrynic acid, furosemide and torsemide; angiotensin converting enzyme (ACE) inhibitors, such as benazepril, captopril, enalapril, fosinopril, lisinopril, moexipril, perinodopril, quinapril, ramipril and trandolapril; inhibitors of the Na—K-ATPase membrane pump, such as digoxin; neutralendopeptidase (NEP) inhibitors; ACE/NEP inhibitors, such as omapatrilat, sampatrilat and fasidotril; angiotensin II antagonists, such as candesartan, eprosartan, irbesartan, losartan, telmisartan and valsartan, in particular valsartan; β-adrenergic receptor blockers, such as acebutolol, atenolol, betaxolol, bisoprolol, metoprolol, nadolol, propranolol, sotalol and timolol; inotropic agents, such as digoxin, dobutamine and milrinone; calcium channel blockers, such as amlodipine, bepridil, diltiazem, felodipine, nicardipine, nimodipine, nifedipine, nisoldipine and verapamil. Other specific antidiabetic compounds are described by Patel Mona (*Expert Opin Investig Drugs*. (2003) April; 12(4):623-33, in FIGS. 1 to 7), which are herein incorporated by reference. A compound of the present invention may be administered either simultaneously, before, or after the other active ingredient, either separately, by the same, or different route of administration, or together in the same pharmaceutical formulation.

The structure of the active agents identified by code numbers (nos.), generic or trade names may be taken from the actual edition of the standard compendium "The Merck Index" or from databases, e.g. Patents International (e.g. IMS World Publications). The corresponding content thereof is hereby incorporated by reference.

In another aspect is the use of the pharmaceutical composition as described above for production of a medicament for the treatment of SCD-mediated disease or conditions.

In another aspect is the use of a pharmaceutical composition or combination as described above for the preparation of a medicament for the treatment of conditions associated with stearoyl-CoA desaturase activity.

A pharmaceutical composition as described above for the treatment of conditions associated with the inhibition of stearoyl-CoA desaturase.

Preparations of Compounds

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic add. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein.

The use of protecting groups is described in detail in Greene, T. W. and P. G. M. Wutz, *Greene's Protective Groups in Organic Synthesis* (2006), 4th Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following reaction schemes illustrate methods to make compounds of this invention. It is understood that one skilled in the art would be able to make these compounds by similar methods or by methods known to one skilled in the art. In general, starting components and reagents may be obtained from sources such as Sigma Aldrich, Lancaster Synthesis, Inc., Maybridge, Matrix Scientific, TCI, and Fluorochem USA, Strem, etc. or synthesized according to sources known to those skilled in the art (see, e.g., Advanced Organic Chemistry: Reactions, Mechanisms, and Structure, 5th edition (Wiley, December 2000)), or prepared as described in this invention. $R^1$, $R^2$, $R^3$, $R^4$, $R^5$, Q, W and V are defined as in the Specification unless specifically defined.

In general, the pyrazine compounds of Formula (I) of this invention can be synthesized following the general procedure as described in Scheme 1, where Q is

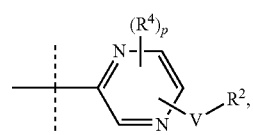

p is 0, X is N, Y is S, W is —N(H)C(O)— and $R^3$ is methyl.

Scheme 1

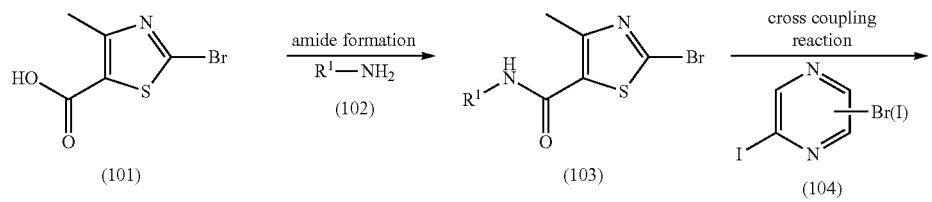

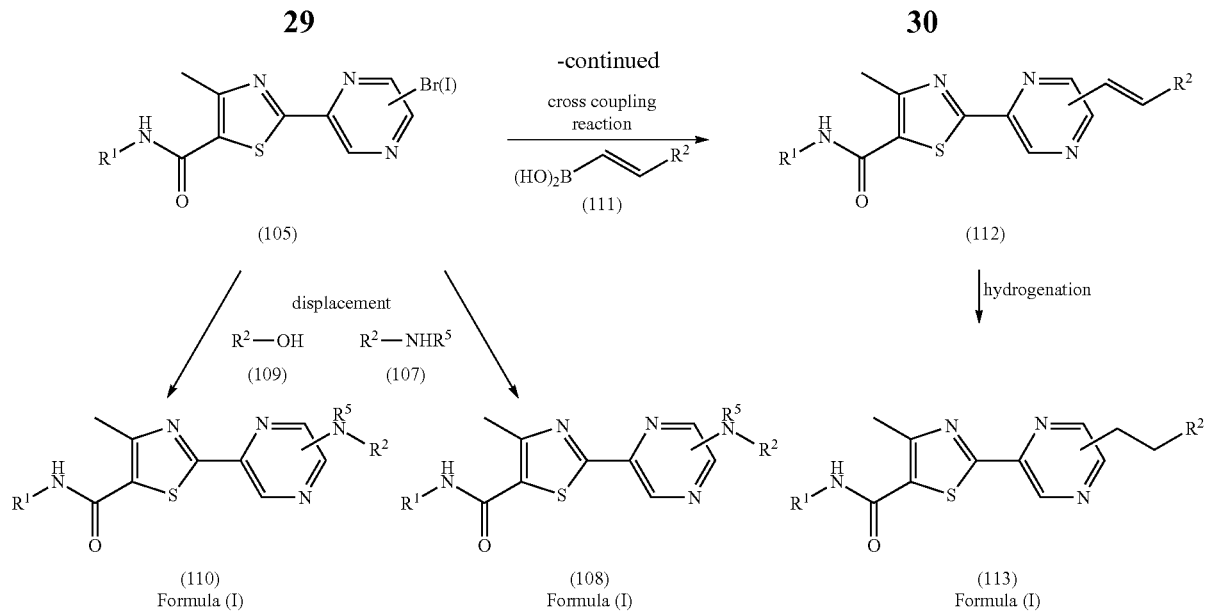

The starting materials for the above reaction scheme are commercially available or can be prepared according to methods known to one skilled in the art or by methods disclosed herein. In general, the compounds of the invention are prepared in the above reaction scheme as follows:

The 2-bromothiazole compound (101) reacts with an amine (102) under standard amide formation conditions to generate compound (103). Compound (103) reacts via a metal-mediated cross coupling reaction with the pyrazine compound (104) to form the compound (105). Compound (105) can then react with an amine nucleophile (107) to form compound (108) of Formula (I), where V is N, $R^5$ is hydrogen or alkyl, and $R^2$ is alkyl. Alternatively, compound (105) can react with an alcohol nucleophile (109) to form compound (110) of Formula (I) where V is O, $R^5$ is hydrogen or alkyl, and $R^2$ is alkyl. Compound (105) can also react via a metal-mediated cross coupling reaction with a compound such as (111) to form compound (112). Compound (110) can be subjected to standard hydrogenation conditions to provide compound (113) of Formula (I) of the invention, where V is a direct bond or an alkylene and $R^2$ is alkyl or aryl.

Alternatively, the pyrazine compounds of Formula (I) of this invention can be synthesized following the general procedure as described in Scheme 2, where Q is

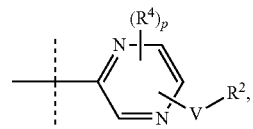

p is 0, X is N, Y is S, W is —N(H)C(O)— and $R^3$ is methyl.

Scheme 2

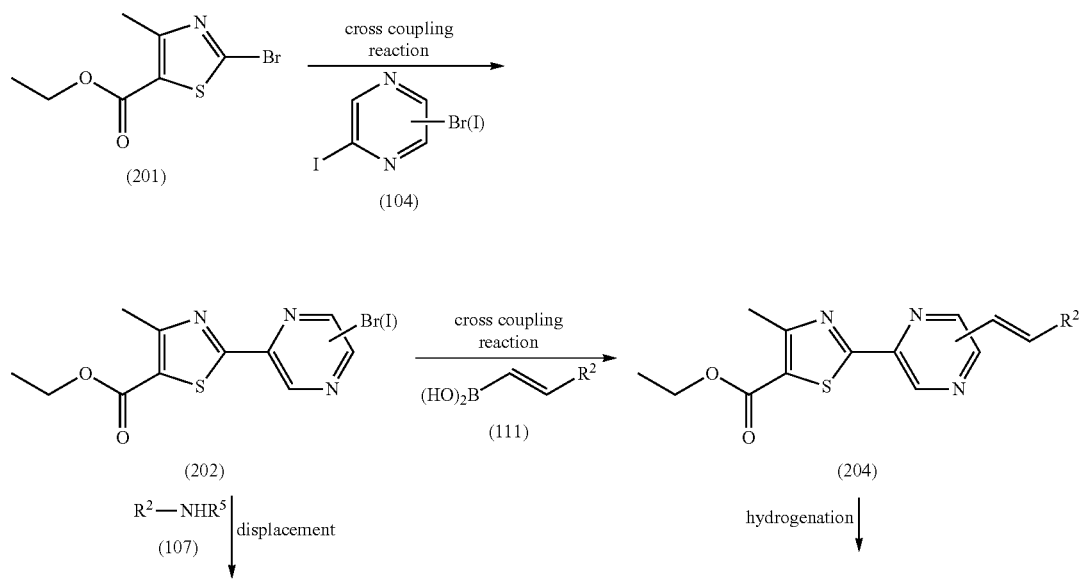

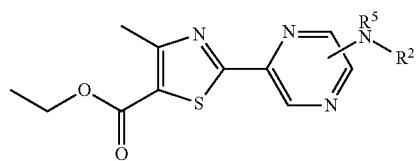

(203)

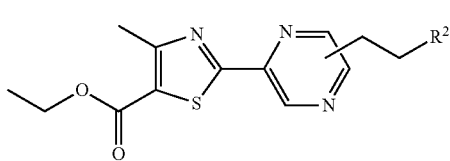

(205)

hydrolysis and amide formation
R¹—NH₂
(102)

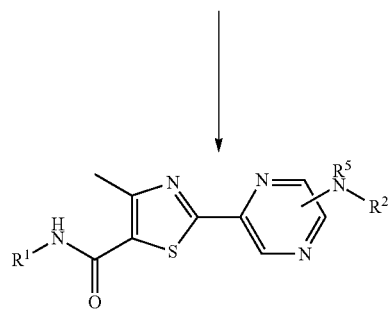

(108)
Formula (I)

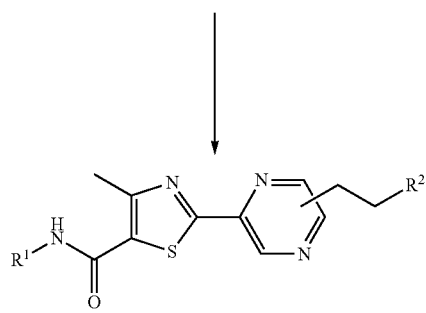

(113)
Formula (I)

The starting materials for the above reaction scheme are commercially available or can be prepared according to methods known to one skilled in the art or by methods disclosed herein. In general, the compounds of the invention are prepared in the above reaction scheme as follows:

The 2-bromothiazole compound (201) reacts via a metal-mediated cross coupling reaction with the pyrazine compound (104) to form the compound (202). Compound (202) can then react with a nucleophile, such as an amine (107) to form compound (203), which under standard amine bond formation conditions provides compound (108) of Formula (I), where V is —N(R⁵)—, R⁵ is hydrogen or alkyl and R² is alkyl. Alternatively, compound (202) can react via a second metal-mediated cross coupling reaction with a compound such as (109) to form compound (204). Compound (204) can be subjected to standard hydrogenation conditions to provide compound (205) which under standard amide bond formation conditions provides compound (111) of Formula (I) of the invention, where V is a direct bond or an alkylene and R² is alkyl or aryl.

In general, the pyrazole compounds of Formula (I) of this invention can be synthesized following the general procedure as described in Scheme 2, where Q is

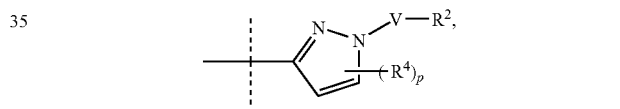

X is N, Y is S, and R³ is methyl.

Scheme 3

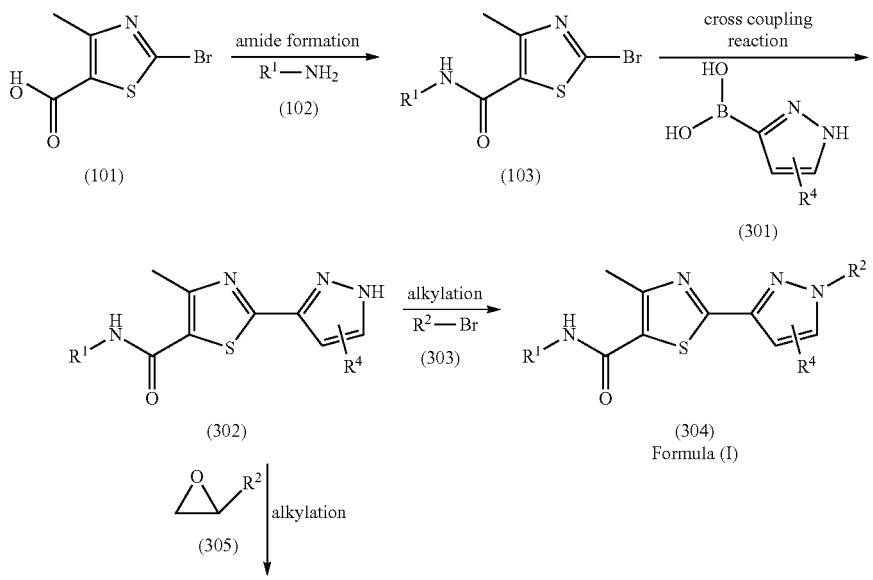

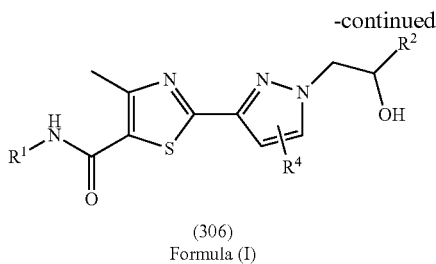

(306)
Formula (I)

The starting materials for the above reaction scheme are commercially available or can be prepared according to methods known to one skilled in the art or by methods disclosed herein. In general, the compounds of the invention are prepared in the above reaction scheme as follows:

The 2-bromothiazole compound (101) reacts with an amine (102) under standard amide formation conditions to generate compound (103). Compound (103) reacts via a metal-mediated cross coupling reaction with the pyrazole compound (301) to form compound (302). Compound (302) reacts with an alkylating reagent, such as bromide (303), to form compound (304) a compound of Formula (I) of the invention, where V is a direct bond or an alkylene and $R^2$ is alkyl or aryl. Alternatively, compound (302) can react with an alkylating agent, such as epoxide (305), to generate compound (306) of Formula (I) of the invention, where V is an alkylene, $R^2$ is alkyl or aryl and $R^4$ is hydrogen, alkyl or haloalkyl.

Alternatively, the pyrazole compounds of Formula (I) of this invention can be synthesized following the general procedure as described in Scheme 5, where Q is

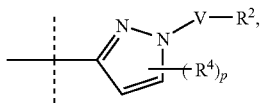

X is N, Y is S, W is —N(H)C(O)—, and $R^3$ is methyl.

Scheme 4

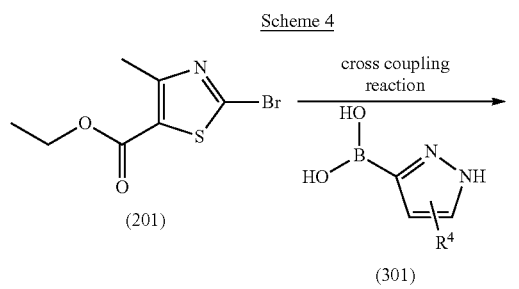

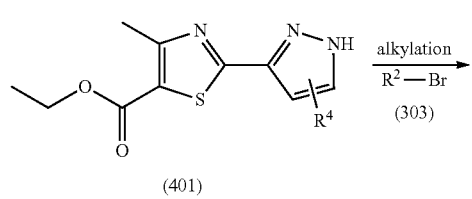

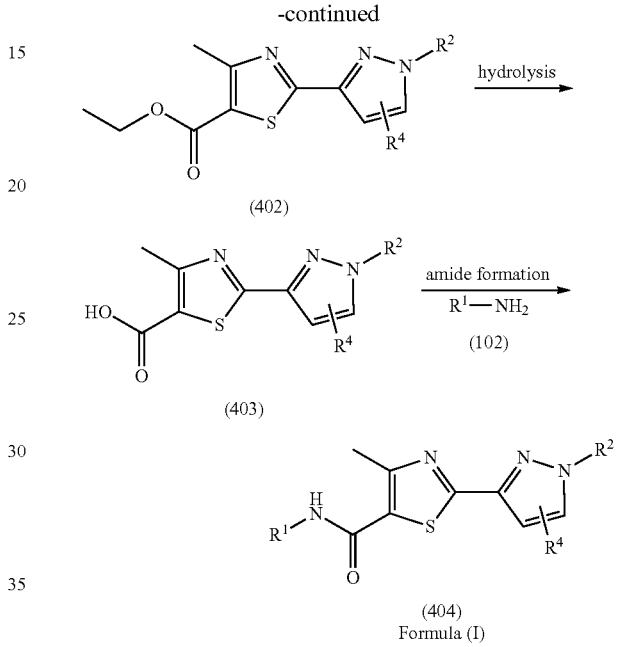

(402)

(403)

(404)
Formula (I)

The starting materials for the above reaction scheme are commercially available or can be prepared according to methods known to one skilled in the art or by methods disclosed herein. In general, the compounds of the invention are prepared in the above reaction scheme as follows:

The 2-bromothiazole compound (201) reacts via a metal-mediated cross coupling reaction with the pyrazole compound (301) to form compound (401). Compound (401) reacts with an alkylating reagent, such as bromide (303), to form compound (402), which undergoes standard hydrolysis to generate compound (403). Compound (403) reacts with an amine (102) under standard amide formation conditions to afford compound (404), a compound of Formula (I), where V is a direct bond or an alkylene, $R^2$ is alkyl or aryl and $R^4$ is hydrogen, alkyl or haloalkyl.

Scheme 5

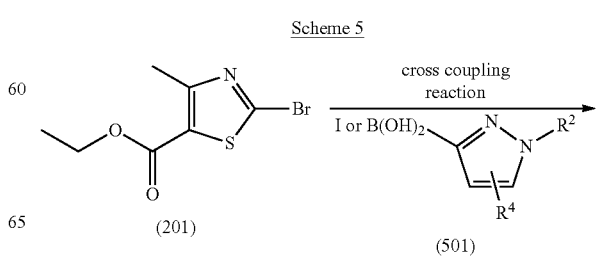

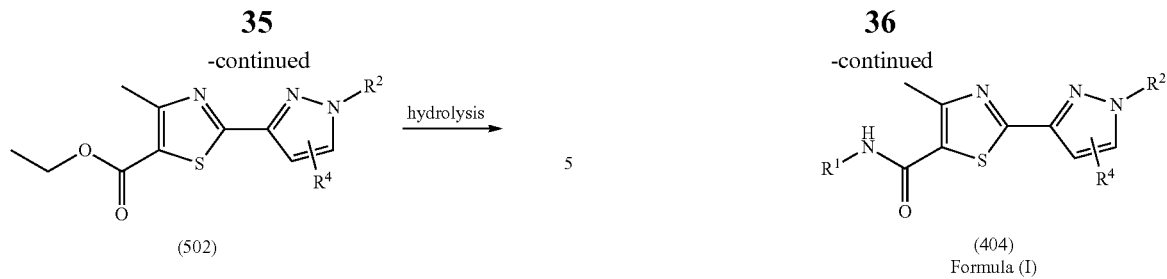

(502)

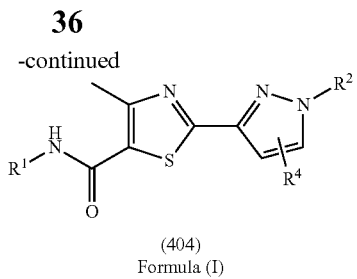

(404)
Formula (I)

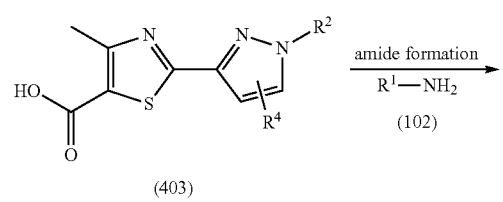

(403)

The starting materials for the above reaction scheme are commercially available or can be prepared according to methods known to one skilled in the art or by methods disclosed herein. In general, the compounds of the invention are prepared in the above reaction scheme as follows:

The 2-bromothiazole compound (201) reacts via a metal-mediated cross coupling reaction with the pyrazole compound (501) to form compound (502). Hydrolysis of compound (502) provides a compound such as (403), which undergoes standard amide bond formation to generate compound (404) a compound of Formula (I), where V is a direct bond or an alkylene, $R^2$ is alkyl or aryl, and $R^4$ is hydrogen, alkyl or haloalkyl.

Scheme 6

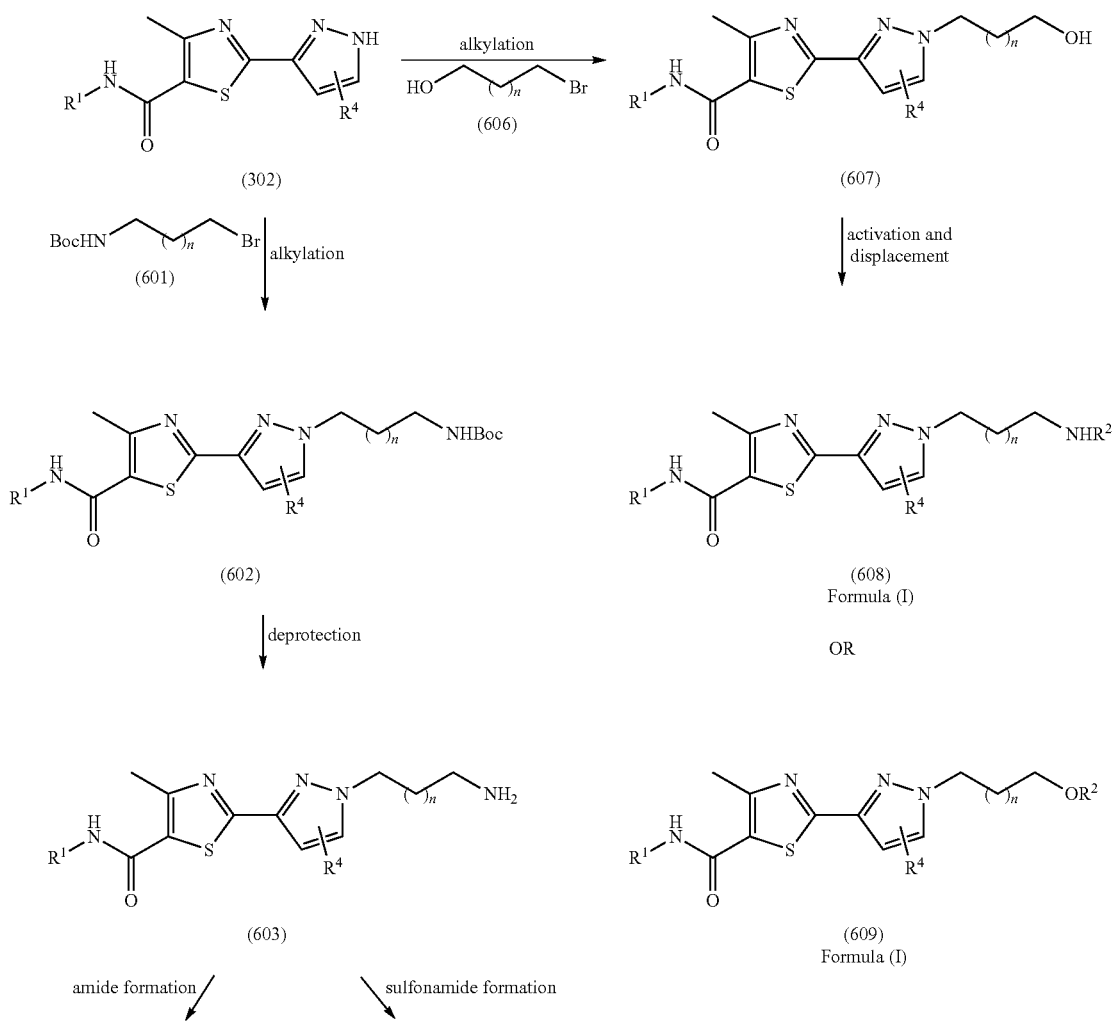

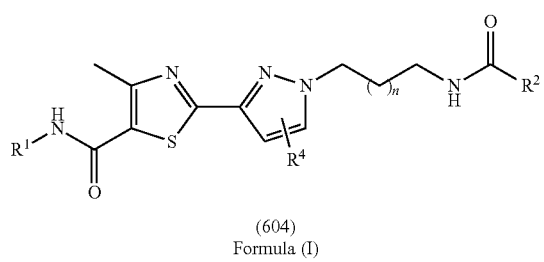

(604)
Formula (I)

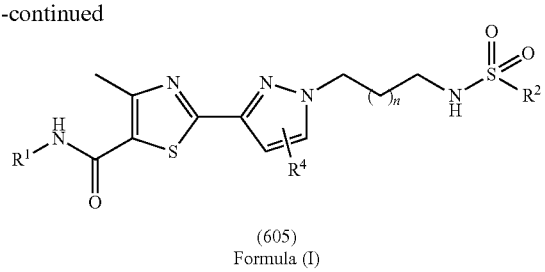

(605)
Formula (I)

The starting materials for the above reaction scheme are commercially available or can be prepared according to methods known to one skilled in the art or by methods disclosed herein. In general, the compounds of the invention are prepared in the above reaction scheme as follows:

The thiazole-pyrrazole compound (302) can be alkylated by a bromide (601) to provide compound (602). Compound (602) can be deprotected under standard conditions to give amine compound (603). Compound (603) can be subjected to standard amide bond formation conditions to give compound (604), a compound of Formula (I) where V is an alkylene, $R^2$ is alkyl or aryl and $R^4$ is hydrogen, alkyl or haloalkyl. Alternatively, compound (603) can be converted via standard methods to the sulfonamide compound (605) which is a compound of Formula (I) where V is a direct bond or an alkylene, $R^2$ is alkyl or aryl and $R^4$ is hydrogen, alkyl or haloalkyl. In a similar manner, compound (302) can also be alkylated by a bromide such as (606) to provide compound (607). Compound (607) can be activated via a mesylate, or similar chemistry, to give an electrophile which can react with an amine nucleophile or an alcohol nucleophile to produce compounds (608) or (609) which are compounds of Formula (I), where V is an alkylene, $R^2$ is alkyl or aryl and $R^4$ is hydrogen, alkyl or haloalkyl.

EXAMPLES

Example 1

Synthesis of 2-(6-chloro-pyrazin-2-yl)-4-methyl-thiazole-5-carboxylic acid benzylamide

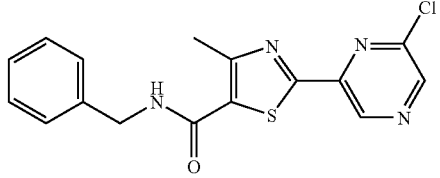

Part A. To a solution of 2-bromo-4-methyl-thiazole-5-carboxylic acid (10.0 g, 45.0 mmol, 1.0 equiv) and diisopropylethylamine (15.6 mL, 90.0 mmol, 2.0 equiv) in anhydrous dichloromethane (400 mL) was added benzotriazol-1-yloxy-tris-(dimethylamino)phosphonium hexafluorophosphate (BOP reagent, 22.0 g, 49.5 mmol, 1.1 equiv) and benzylamine (5.4 mL, 49.5 mmol, 1.1 equiv). The resulting mixture was stirred at ambient temperature for 12 hr. The reaction was diluted with dichloromethane, washed with water, brine, dried ($Na_2SO_4$), filtered and concentrated in vacuo. The crude product was purified by column chromatography [$SiO_2$, ethyl acetate/hexanes, 10:90 to 35:65, v/v]. Further purification by stirring in pentane then filtration afforded 2-bromo-4-methyl-thiazole-5-carboxylic acid benzylamide (9.0 g, 64% yield). $^1$H NMR (400 MHz, DMSO-$d_6$) δ 8.84 (bs, 1H), 7.23-7.36 (m, 5H), 4.42 (d, J=8.0 Hz, 2H), 2.55 (s, 3H); MS (M+H)$^+$ =312.1, $R_t$=1.32 min.

Part B. To a solution of 2-bromo-4-methyl-thiazole-5-carboxylic acid benzylamide (350 mg, 1.13 mmol, 1.0 equiv) in dimethyl ether (4 mL) was added $Na_2CO_3$ (240 mg, 2.26 mmol, 2.0 equiv), 6-chloropyrazine-2-boronic acid pinacol ester (680 mg, 2.82 mmol, 2.5 equiv), $PdCl_2$(dppf) (83 mg, 0.11 mmol, 0.1 equiv) and water (1 mL) in a sealed tube. The reaction was immersed in an oil bath preheated to 50° C. After 3 days, the reaction was cooled and the solvent was removed in vacuo. The crude product was purified by preparative HPLC (acetonitrile/water, 0.1% trifluoroacetic acid) to give 2-(6-chloropyrazin-2-yl)-4-methyl-thiazole-5-carboxylic acid benzylamide (90 mg, 23% yield). $^1$H NMR (400 MHz, DMSO-$d_6$) δ 9.27 (s, 1H), 8.93 (s, 1H), 7.31-7.39 (m, 4H), 7.23-7.30 (m, 1H), 4.46 (d, J=8.0 Hz, 2H), 2.67 (s, 3H); MS (M+H)$^+$=345.1, $R_t$=1.46 min.

Example 2

Synthesis of 2-(6-benzyl-pyrazin-2-yl)-4-methyl-thiazole-5-carboxylic acid benzylamide

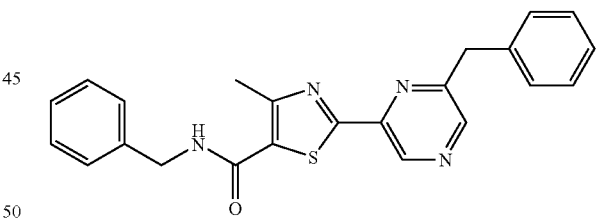

Part A. A mixture of 2,6-dichloropyrazine (2.5 g, 16.8 mmol, 1.0 equiv), p-toluenesulfonic acid (6.4 g, 33.6 mmol, 2.0 equiv), sodium iodide (20.0 g, 133.3 mmol, 8.0 equiv), 15-crown-5 (2.0 mL) and sulfolane (40 mL) was heated at 150° C. and stirred in a sealed tube for 2 hr. After cooling, water (100 mL) was added to the reaction mixture. The mixture was then neutralized with a saturated solution of sodium hydrogencarbonate, and washed with a saturated solution of sodium thiosulfate. The mixture was extracted with diethyl ether (5×100 mL). The ether extracts were dried ($Na_2SO_4$) and concentrated in vacuo. 2,6-Diiodopyrazine was precipitated with 10 mL of water, filtered, washed with water and pentane to provide a pale yellow powder after lyophilization (2.1 g, 38%). $^1$H NMR (400 MHz, $CDCl_3$) δ 8.74 (s, 2H); MS (M+H)$^+$=332, $R_t$=1.29 min.

Part B. An oven-dried sealed tube was charged with 2-bromo-4-methyl-thiazole-5-carboxylic acid benzylamide (800 mg, 2.57 mmol, 1.0 equiv). The sealed tube was purged with nitrogen and Rieke zinc (10 mL, 10 g of zinc in 100 mL of tetrahydrofuran) was added. The reaction was heated in the microwave oven for 15 min. at 100° C. Stirring was stopped and the remaining zinc was allowed to settle. The supernatant containing the zinc reagent was transferred via syringe to a solution of 2,6-diiodopyrazine (680 mg, 2.1 mmol, 0.8 equiv), Pd(PPh$_3$)$_4$ (236 mg, 0.2 mmol, 7 mol %) in tetrahydrofuran (5 mL) and dimethyl formamide (0.2 mL). The reaction mixture was purged with nitrogen for 10 min, then stirred at 160° C. for 16 hr. After cooling, the solvent was removed in vacuo and the crude product was purified by column chromatography [SiO$_2$, ethyl acetate/heptane, 10:90 to 40:60, v/v] to afford 2-(6-iodo-pyrazin-2-yl)-4-methyl-thiazole-5-carboxylic acid benzylamide (140 mg, 13%). MS (M+H)$^+$=436, R$_f$=1.51 min.

Part C. To a solution of 2-(6-iodo-pyrazin-2-yl)-4-methyl-thiazole-5-carboxylic acid benzylamide (70 mg, 0.16 mmol, 1.0 equiv) in dimethyl ether (1 mL) was added Na$_2$CO$_3$ (34 mg, 0.32 mmol, 2.0 equiv), benzyl boronic acid pinacol ester (87 µL, 0.40 mmol, 2.5 equiv), PdCl$_2$(dppf) (11 mg, 0.02 mmol, 0.1 equiv) and water (0.1 mL) in a sealed tube. The reaction was immersed in an oil bath preheated to 100° C. After stirring for 4 hr, the reaction was cooled and the solvent was removed in vacuo. The crude product was purified by column chromatography [SiO$_2$, methanol/dichloromethane, 0:100 to 10:90, v/v] and recrystallization (methanol/pentane) to give 2-(6-benzyl-pyrazin-2-yl)-4-methyl-thiazole-5-carboxylic acid benzylamide (41 mg, 65%). $^1$H NMR (400 MHz, CD$_2$Cl$_2$) δ 9.17 (s, 1H), 8.47 (s, 1H), 7.22-7.37 (m, 10H), 6.23 (bs, 1H), 4.59 (d, J=8.0 Hz, 2H), 4.19 (s, 2H), 2.72 (s, 3H); HRMS (M+H)$^+$=401.14.

Example 3

Synthesis of 4-methyl-2-[6-((E)-styryl)-pyrazin-2-yl] thiazole-5-carboxylic acid benzylamide

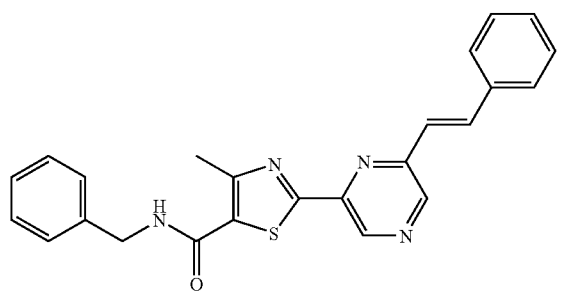

To a solution of 2-(6-chloro-pyrazin-2-yl)-4-methyl-thiazole-5-carboxylic acid benzylamide (40 mg, 0.12 mmol, 1.0 equiv) in dimethyl ether (0.6 mL) was added Na$_2$CO$_3$ (25 mg, 0.23 mmol, 2.0 equiv), trans-2-phenylvinyl boronic acid (43 mg, 0.29 mmol, 2.5 equiv), CombiPhos Pd-6 (6.0 mg, 0.01 mmol, 0.1 equiv) and water (0.2 mL) in a sealed tube. The reaction was heated in the microwave oven at 100° C. for 25 min. After cooling, the solvent was removed in vacuo. The crude product was purified by column chromatography [SiO$_2$, methanol/dichloromethane, 0:100 to 5:95, v/v] to give 4-methyl-2-[6-((E)-styryl)-pyrazin-2-yl]-thiazole-5-carboxylic acid benzylamide (32 mg, 67%). $^1$H NMR (400 MHz, CD$_2$Cl$_2$) δ 9.17 (s, 1H), 8.64 (s, 1H), 7.83 (d, J=16.0 Hz, 1H), 7.62-7.64 (m, 2H), 7.28-7.43 (m, 8H), 7.19 (d, J=16.0 Hz, 1H), 6.25 (bs, 1H), 4.61 (d, J=1.0 Hz, 2H), 2.74 (s, 3H); HRMS (M+H)$^+$=413.14.

Example 4

Synthesis of 4-methyl-2-(6-phenethyl-pyrazin-2-yl)-thiazole-5-carboxylic acid benzylamide

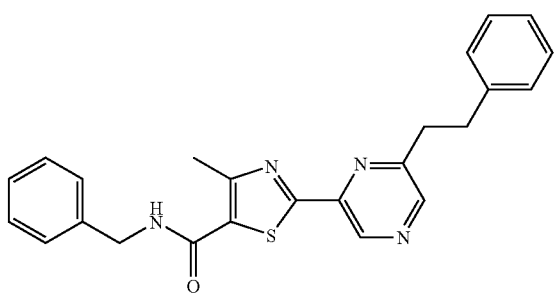

To a solution of 4-methyl-2-[6-((E)-styryl)-pyrazin-2-yl]-thiazole-5-carboxylic acid benzylamide (32 mg, 0.08 mmol, 1.0 equiv.) in ethyl acetate was added Pd/C (15 mg, 10%). The flask was first purged with nitrogen, then with hydrogen. The reaction mixture was stirred at ambient temperature for 18 hr and monitored by LCMS. Upon completion, the reaction mixture was diluted with ethyl acetate, filtered through Celite and concentrated in vacuo. The crude product was purified by column chromatography [SiO$_2$, methanol/dichloromethane, 0:100 to 5:95, v/v] and recrystallization (methanol) to afford 4-methyl-2-(6-phenethyl-pyrazin-2-yl)-thiazole-5-carboxylic acid benzylamide (18 mg, 56%). $^1$H NMR (400 MHz, CD$_2$Cl$_2$) δ 9.15 (s, 1H), 8.36 (s, 1H), 7.14-7.37 (m, 10H), 6.21 (bs, 1H), 4.60 (d, J=8.0 Hz, 2H), 3.09-3.16 (m, 4H), 2.73 (s, 3H); HRMS (M+H)$^+$=415.16.

Example 5

Synthesis of 4-methyl-2-[6-(3-phenyl-propyl)-pyrazin-2-yl]-thiazole-5-carboxylic acid benzylamide

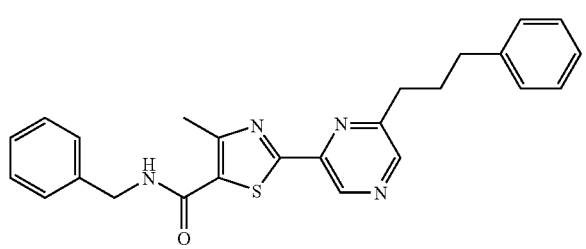

Part A. To a solution of 2-(6-iodo-pyrazin-2-yl)-4-methyl-thiazole-5-carboxylic acid benzylamide (80 mg, 0.18 mmol, 1.0 equiv) in dimethyl ether (1 mL) was added Na$_2$CO$_3$ (38 mg, 0.36 mmol, 2.0 equiv), trans-3-phenylpropen-1-yl boronic acid (73 mg, 0.45 mmol, 2.5 equiv), PdCl$_2$(dppf) (1.3 mg, 0.02 mmol, 0.1 equiv) and water (0.1 mL) in a sealed tube. The reaction vessel was immersed in an oil bath preheated to 60° C. After stirring for 3 hr, the reaction mixture was cooled and the solvent was removed in vacuo. The crude product was purified by column chromatography [SiO$_2$, methanol/dichloromethane, 0:100 to 10:90, v/v] to give 4-methyl-2-[6-((E)-3-phenyl-propenyl)-pyrazin-2-yl]-thiazole-5-carboxylic acid benzylamide (39 mg, 50%); MS (M+H)$^+$=427.1, R$_t$=1.70 min.

Part B. To a solution of 4-methyl-2-[6-((E)-3-phenyl-propenyl)-pyrazin-2-yl]-thiazole-5-carboxylic acid benzylamide (39 mg, 0.09 mmol, 1.0 equiv) in ethyl acetate was added Pd/C (15 mg, 10%). The flask was first purged with nitrogen, then with hydrogen. The reaction mixture was stirred at ambient temperature for 60 hr and monitored by LCMS. Upon completion, the reaction mixture was diluted with ethyl acetate, filtered through Celite and concentrated in vacuo. The crude product was purified by prep HPLC (acetonitrile/water, 0.1% trifluoroacetic acid) to afford 4-methyl-2-[6-(3-phenyl-propyl)-pyrazin-2-yl]-thiazole-5-carboxylic acid benzylamide (19 mg, 60%). $^1$H NMR (400 MHz, CD$_2$Cl$_2$) δ 9.14 (s, 1H), 9.12 (s, 1H), 7.14-7.36 (m, 10H), 6.23 (bs, 1H), 4.59 (d, J=8.0 Hz, 2H), 2.86 (t, J=8.0 Hz, 2H), 2.72 (s, 3H), 2.69-2.72 (m, 2H), 2.07-2.15 (m, 21-1); HRMS (M+H)$^+$=429.17.

Example 6

Synthesis of 2-{6-[(E)-2-(4-fluoro-phenyl)-vinyl]-pyrazin-2-yl}-4-methyl-thiazole-5-carboxylic acid benzylamide

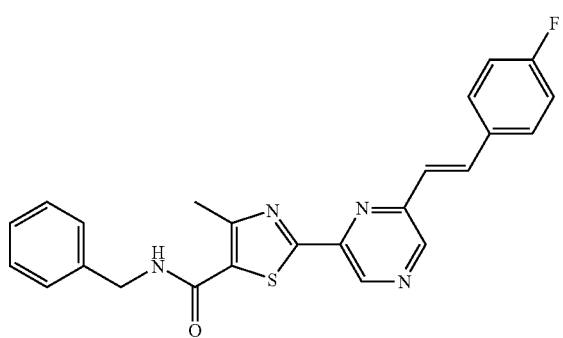

To a solution of 2-(6-iodo-pyrazin-2-yl)-4-methyl-thiazole-5-carboxylic acid benzylamide (100 mg, 0.23 mmol, 1.0 equiv) in dimethyl ether (1 mL) was added Na$_2$CO$_3$ (49 mg, 0.46 mmol, 2.0 equiv), trans-2-(4-fluorophenyl)vinyl boronic acid (95 mg, 0.57 mmol, 2.5 equiv), PdCl$_2$(dppf) (17 mg, 0.02 mmol, 0.1 equiv) and water (0.1 mL) in a sealed tube. The reaction vessel was immersed in an oil bath preheated to 100° C. After stirring for 1 hr, the reaction mixture was cooled and the solvent was removed in vacuo. The crude product was purified by column chromatography [SiO$_2$, methanol/dichloromethane, 0:100 to 5:95, v/v] and recrystallization (methanol/pentane) to give 2-{6-[(E)-2-(4-fluoro-phenyl)-vinyl]-pyrazin-2-yl}-4-methyl-thiazole-5-carboxylic acid benzylamide (59 mg, 60%). $^1$H NMR (400 MHz, CD$_2$Cl$_2$) δ 9.17 (s, 1H), 8.63 (s, 1H), 7.81 (d, J=16.0 Hz, 1H), 7.61-7.64 (m, 2H), 7.27-7.37 (m, 5H), 7.09-7.13 (m, 3H), 6.23 (bs, 1H), 4.61 (d, J=8.0 Hz, 2H), 2.74 (s, 3H); HRMS (M+H)$^+$=431.13.

Example 7

Synthesis of 2-{6-[2-(4-fluoro-phenyl)-ethyl]-pyrazin-2-yl}-4-methyl-thiazole-5-carboxylic acid benzylamide

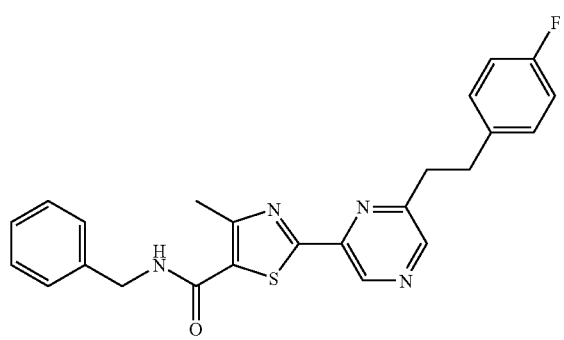

To a solution of 2-{6-[(E)-2-(4-fluoro-phenyl)-vinyl]-pyrazin-2-yl}-4-methyl-thiazole-5-carboxylic acid benzylamide (40 mg, 0.09 mmol, 1.0 equiv) in ethyl acetate/ethanol (1:1) was added Pd(OH)$_2$ (10 mg, 20%). The flask was first purged with nitrogen, then with hydrogen. The reaction mixture was stirred at ambient temperature for 3 hr and monitored by LCMS. Upon completion, the reaction mixture was diluted with ethyl acetate, filtered through Celite and concentrated in vacuo. The crude product was purified by preparative HPLC (acetonitrile/water, 0.1% trifluoroacetic acid) to afford {6-[2-(4-fluoro-phenyl)-ethyl]-pyrazin-2-yl}-4-methyl-thiazole-5-carboxylic acid benzylamide (24 mg, 60%). $^1$H NMR (400 MHz, CD$_2$Cl$_2$) δ 9.15 (s, 1H), 8.36 (s, 1H), 7.28-7.37 (m, 5H), 7.13-7.17 (m, 2H), 6.92-6.96 (m, 2H), 6.25 (bs, 1H), 4.60 (d, J=4.0 Hz, 2H), 3.07-3.16 (m, 4H), 2.73 (s, 3H); HRMS (M+H)$^+$=433.15.

Example 8

Synthesis of 4-methyl-2-{6-[(E)-2-(4-trifluoromethyl-phenyl)-vinyl]-pyrazin-2-yl}-thiazole-5-carboxylic acid benzylamide

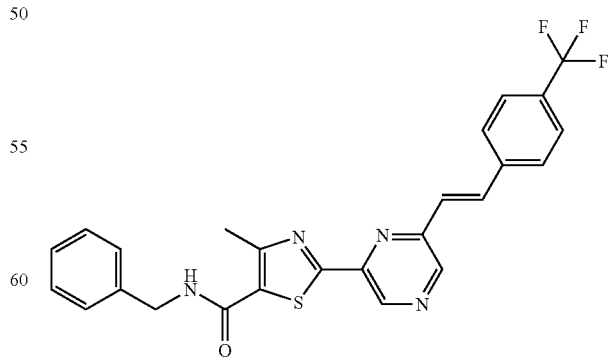

To a solution of 2-(6-iodo-pyrazin-2-yl)-4-methyl-thiazole-5-carboxylic acid benzylamide (100 mg, 0.23 mmol, 1.0 equiv) in dimethyl ether (1 mL) was added Na$_2$CO$_3$ (49 mg, 0.46 mmol, 2.0 equiv), trans-2-(4-trifluoromethylphenyl)vinyl boronic acid (123 mg, 0.57 mmol, 2.5 equiv.), PdCl₂ (dppf) (17 mg, 0.02 mmol, 0.1 equiv) and water (0.1 mL) in a sealed tube. The reaction vessel was immersed in an oil bath preheated to 100° C. After stirring for 2 hr, the reaction mixture was cooled and the solvent was removed in vacuo. The crude product was purified by column chromatography [SiO₂, methanol/dichloromethane, 0:100 to 10:90, v/v] and recrystallization (methanol/pentane) to afford 4-methyl-2-{6-[(E)-2-(4-trifluoromethyl-phenyl)-vinyl]-pyrazin-2-yl}-thiazole-5-carboxylic acid benzylamide (77 mg, 70%). ¹H NMR (400 MHz, CD₂Cl₂) δ 9.23 (s, 1H), 8.68 (s, 1H), 7.87 (d, J=16.0 Hz, 1H), 7.75 (d, J=8.0 Hz, 2H), 7.66 (d, J=12.0 Hz, 2H), 7.37 (d, J=4.0 Hz, 4H), 7.28-7.36 (m, 1H), 7.28 (d, J=16.0 Hz, 1H), 6.25 (bs, 1H), 4.62 (d, J=4.0 Hz, 2H), 2.74 (s, 3H); HRMS (M+H)⁺=481.13.

Example 9

Synthesis of 4-methyl-2-{6-[2-(4-trifluoromethyl-phenyl)-ethyl]-pyrazin-2-yl}-thiazole-5-carboxylic acid benzylamide

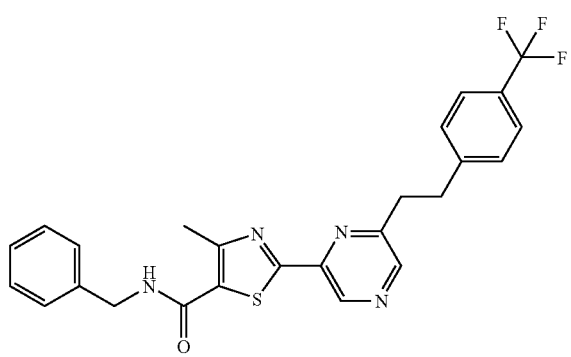

To a solution of 4-methyl-2-{6-[(E)-2-(4-trifluoromethyl-phenyl)-vinyl]-pyrazin-2-yl}-thiazole-5-carboxylic acid benzylamide (40 mg, 0.08 mmol, 1.0 equiv) in ethyl acetate/ethanol (1:1) was added Pd(OH)₂ (10 mg, 20%). The flask was first purged with nitrogen, then with hydrogen. The reaction mixture was stirred at ambient temperature for 3 hr and monitored by LCMS. Upon completion, the reaction mixture was diluted with ethyl acetate, filtered through Celite and concentrated in vacuo. The crude product was purified by preparative HPLC (acetonitrile/water, 0.1% trifluoroacetic acid) to afford 4-methyl-2-{6-[2-(4-trifluoromethyl-phenyl)-ethyl]-pyrazin-2-yl}-thiazole-5-carboxylic acid benzylamide (20 mg, 50%). ¹H NMR (400 MHz, CD₂Cl₂) δ 9.16 (s, 1H), 8.39 (s, 1H), 7.52 (d, J=8.0 Hz, 2H), 7.28-7.37 (m, 7H), 6.25 (bs, 1H), 4.60 (d, J=8.0 Hz, 2H), 3.19 (apparent s, 4H), 2.72 (s, 3H); HRMS (M+H)⁺=483.14.

Example 10

Synthesis of 2-(5-bromo-pyrazin-2-yl)-4-methyl-thiazole-5-carboxylic acid benzylamide

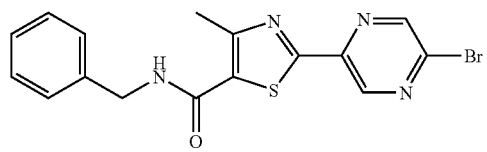

Part A. To a solution of 5-bromopyrazinamine (3.0 g, 17.2 mmol, 1.0 equiv) in HI (11.1 mL, 57% in water) at 0° C. was slowly added I₂ (3.0 g, 24.1 mmol, 0.7 equiv) over 1 hr, followed by addition of NaNO₂ (5.0 g, 145 mmol, 4.2 equiv) over a period of 3 hr at 0° C. The reaction mixture was made alkaline by first adding 10% Na₂S₂O₅ solution (150 mL), then saturated Na₂CO₃ solution (90 mL). The mixture was extracted with diethyl ether (3×250 mL). The organic layer was washed with 10% Na₂S₂O₅ solution, dried (Na₂SO₄), filtered and concentrated in vacuo. The crude product was purified by column chromatography [SiO₂, ethyl acetate/hexanes, 0:100 to 10:90, v/v] to give 2-bromo-5-iodo-pyrazine (1.6 g, 32%). ¹H NMR (400 MHz, CD₂Cl₂) δ 8.62 (s, 1H), 8.51 (s, 1H).

Part B. An oven-dried sealed tube was charged with 2-bromo-4-methyl-thiazole-5-carboxylic acid benzylamide (400 mg, 1.28 mmol, 1.0 equiv). The sealed tube was purged with nitrogen and Rieke zinc (4 mL, 10 g of zinc in 100 mL of tetrahydrofuran) was added. The reaction was heated in the microwave oven for 15 min at 100° C. Stirring was stopped and the remaining zinc was allowed to settle. The supernatant containing the zinc reagent was transferred via syringe to a solution of 2-bromo-5-iodo-pyrazine (292 mg, 1.0 mmol, 0.8 equiv), Pd(PPh₃)₄ (59 mg, 0.05 mmol, 4 mol %) in tetrahydrofuran (3 mL). The reaction mixture was purged with nitrogen for 10 min, then stirred at 160° C. for 20 hr. After cooling, the solvent was removed in vacuo and the crude product was purified by preparative HPLC (acetonitrile/water, 0.1% trifluoroacetic acid) to afford 2-(5-bromo-pyrazin-2-yl)-4-methyl-thiazole-5-carboxylic acid benzylamide (35 mg, 7%). ¹H NMR (400 MHz, CD₂Cl₂) δ 9.12 (s, 1H), 8.63 (s, 1H), 7.28-7.36 (m, 5H), 6.22 (bs, 1H), 4.59 (d, J=8.0 Hz, 2H), 2.72 (s, 3H); HRMS (M+H)⁺=389.01.

Example 11

Synthesis of 2-{5-[2-(4-fluoro-phenyl)-ethyl]-pyrazin-2-yl}-4-methyl-thiazole-5-carboxylic acid benzylamide

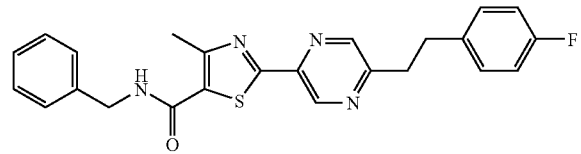

Part A. To a solution of 2-(5-bromo-pyrazin-2-yl)-4-methyl-thiazole-5-carboxylic acid benzylamide (35 mg, 0.09 mmol, 1.0 equiv) in dimethyl ether (1 mL) was added, Na$_2$CO$_3$ (19 mg, 0.18 mmol, 2.0 equiv), trans-2-(4-fluorophenyl)vinyl boronic acid (37 mg, 0.22 mmol, 2.5 equiv), PdCl$_2$(dppf) (3.0 mg, 5 mol %) and water (0.1 mL) in a sealed tube. The reaction was heated in microwave oven at 100° C. for 1 hr. The reaction mixture was cooled and the solvent was removed in vacuo. The crude product was purified by column chromatography [SiO$_2$, methanol/dichloromethane, 0:100 to 15:85, v/v] to afford 2-{5-[(E)-2-(4-fluoro-phenyl)-vinyl]-pyrazin-2-yl}-4-methyl-thiazole-5-carboxylic acid benzylamide (25 mg, 64%). MS (M+H)$^+$=431.1, R$_t$=1.66 min.

Part B. To a solution of 2-{5-[(E)-2-(4-fluoro-phenyl)-vinyl]-pyrazin-2-yl}-4-methyl-thiazole-5-carboxylic acid benzylamide (20 mg, 0.05 mmol, 1.0 equiv) in ethyl acetate/ethanol (1:1) was added Pd(OH)$_2$ (10 mg, 20%). The flask was first purged with nitrogen, then with hydrogen. The reaction mixture was stirred at ambient temperature for 3 hr and monitored by LCMS. Upon completion, the reaction mixture was diluted with ethyl acetate, filtered through Celite and concentrated in vacuo. The crude product was purified by preparative HPLC (acetonitrile/water, 0.1% trifluoroacetic acid) to afford 2-{5-[2-(4-fluoro-phenyl)-ethyl]-pyrazin-2-yl}-4-methyl-thiazole-5-carboxylic acid benzylamide (13 mg, 65%). $^1$H NMR (400 MHz, CD$_2$Cl$_2$) δ 9.27 (s, 1H), 8.27 (s, 1H), 7.27-7.35 (m, 5H), 7.12-7.15 (m, 2H), 6.92-6.96 (m, 2H), 6.19 (bs, 1H), 4.58 (d, J=4.0 Hz, 2H), 3.05-3.16 (m, 4H), 2.72 (s, 3H); HRMS (M+H)$^+$=433.15.

Example 12

Synthesis of 4-methyl-2-[5-(3-phenyl-propyl)-pyrazin-2-yl]-thiazole-5-carboxylic acid benzylamide

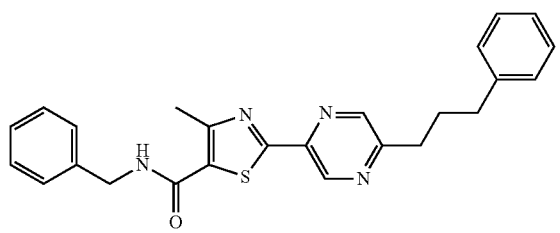

Part A. To a solution of 2-(5-bromo-pyrazin-2-yl)-4-methyl-thiazole-5-carboxylic acid benzylamide (40 mg, 0.10 mmol, 1.0 equiv) in dimethyl ether (1 mL) was added Na$_2$CO$_3$ (21 mg, 0.20 mmol, 2.0 equiv), trans-3-phenylpropen-1-yl boronic acid (41 mg, 0.25 mmol, 2.5 equiv), PdCl$_2$(dppf) (3.6 mg, 5 mol %) and water (0.1 mL) in a sealed tube. The reaction was immersed in an oil bath preheated to 100° C. After stirring for 3 hr, the reaction was cooled and the solvent was removed in vacuo. The crude product was purified by column chromatography [SiO$_2$, methanol/dichloromethane, 0:100 to 10:90, v/v] to give 4-methyl-2-[5-((E)-3-phenyl-propenyl)-pyrazin-2-yl]-thiazole-5-carboxylic acid benzylamide (20 mg, 46%)

Part B. To a solution of 4-methyl-2-[5-((E)-3-phenyl-propenyl)-pyrazin-2-yl]-thiazole-5-carboxylic acid benzylamide (20 mg, 0.05 mmol, 1.0 equiv) in ethyl acetate was added Pd/C (15 mg, 10%). The flask was first purged with nitrogen, then with hydrogen. The reaction mixture was stirred at ambient temperature for 60 hr and monitored by LCMS. Upon completion, the reaction mixture was diluted with ethyl acetate, filtered through Celite and concentrated in vacuo. The crude product was purified by preparative HPLC (acetonitrile/water, 0.1% trifluoroacetic acid) to afford 4-methyl-2-[5-(3-phenyl-propyl)-pyrazin-2-yl]-thiazole-5-carboxylic acid benzylamide (12 mg, 60%). $^1$H NMR (400 MHz, CD$_2$Cl$_2$) δ 9.25 (s, 1H), 8.38 (s, 1H), 7.14-7.35 (m, 10H), 6.20 (bs, 1H), 4.58 (d, J=4.0 Hz, 2H), 2.87 (t, J=8.0 Hz, 2H), 2.72 (s, 3H), 2.69 (t, J=8.0 Hz, 2H), 2.07-2.13 (m, 2H); HRMS (M+H)$^+$=429.17.

Example 13

Synthesis of 2-(6-dimethylamino-pyrazin-2-yl)-4-methyl-thiazole-5-carboxylic acid benzylamide

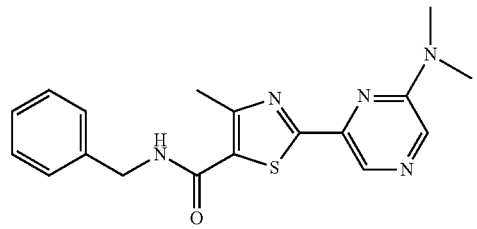

To a sealed tube was added 2-(6-iodo-pyrazin-2-yl)-4-methyl-thiazole-5-carboxylic acid benzylamide (See Example 2, 50 mg, 0.11 mmol, 1.0 equiv) and dimethyl formamide (1 mL). The reaction mixture was stirred at 100° C. After 18 hr, the reaction mixture was cooled to room temperature and diluted with dichloromethane washed with saturated NaHCO$_3$, brine, dried (Na$_2$SO$_4$), filtered, and concentrated in vacuo. The crude product was purified by preparative HPLC (acetonitrile/water, 0.1% trifluoroacetic acid) to afford 2-(6-dimethylamino-pyrazin-2-yl)-4-methyl-thiazole-5-carboxylic acid benzylamide (32 mg, 80%). $^1$H NMR (400 MHz, CD$_2$Cl$_2$) δ 8.51 (s, 1H), 8.06 (s, 1H), 7.29-7.36 (m, 5H), 6.21 (bs, 1H), 4.59 (d, J=8.0 Hz, 2H), 3.17 (s, 6H), 2.71 (s, 3H); HRMS (M+H)$^+$=354.13.

Example 14

Synthesis of 2-{6-[(4-fluoro-benzyl)-methyl-amino]-pyrazin-2-yl}-4-methyl-thiazole-5-carboxylic acid 4-fluoro-benzylamide

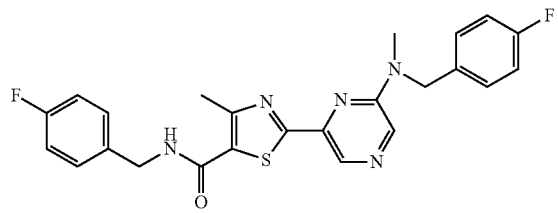

Part A. To a solution of 2-bromo-4-methyl-thiazole-5-carboxylic acid (10 g, 45.0 mmol, 1.0 equiv) and diisopropylethylamine (15.6 mL, 90.0 mmol, 2.0 equiv) in anhydrous dichloromethane (400 mL) was added benzotriazol-1-yloxy-tris-(dimethylamino)phosphonium hexafluorophosphate (BOP reagent, 22 g, 49.5 mmol, 1.1 equiv) and 4-fluorobenzylamine (5.7 mL, 49.5 mmol, 1.1 equiv). The resulting mixture was stirred at ambient temperature for 12 hr. The reaction mixture was diluted with dichloromethane, washed with water then brine, dried ($Na_2SO_4$), filtered and concentrated in vacuo. The crude product was purified by column chromatography [$SiO_2$, ethyl acetate/hexanes, 10:90 to 40:60, v/v], followed by stirring in pentane and filtering the solid to afford 2-bromo-4-methyl-thiazole-5-carboxylic acid 4-fluoro-benzylamide (8.5 g, 57% yield). MS $(M+H)^+$=330.1, $R_t$=1.36 min.

Part B. An oven-dried sealed tube was charged with 2-bromo-4-methyl-thiazole-5-carboxylic acid 4-fluoro-benzylamide (1.0 g, 3.03 mmol, 1.0 equiv). The sealed tube was purged with nitrogen and Rieke zinc (10 mL, 10 g of zinc in 100 mL of tetrahydrofuran) was added. The reaction was heated in the microwave oven for 15 min at 100° C. Stirring was stopped and the remaining zinc was allowed to settle. The supernatant containing the zinc reagent was transferred via syringe to a solution of 2,6-diiodopyrazine (704 mg, 2.1 mmol, 0.7 equiv), $Pd(PPh_3)_4$ (175 mg, 0.2 mmol, 5 mol %) in tetrahydrofuran (2 mL) and dimethyl formamide (0.1 mL). The reaction mixture was purged with nitrogen for 10 min, then stirred at 140° C. for 20 hr. After cooling, the solvent was removed in vacuo and the crude product was purified by column chromatography [$SiO_2$, ethyl acetate/heptane, 10:90 to 40:60, v/v] to afford 2-(6-iodo-pyrazin-2-yl)-4-methyl-thiazole-5-carboxylic acid 4-fluoro-benzylamide (100 mg, 7%). MS $(M+H)^+$=455.1, $R_t$=1.53 min.

Part C. To a sealed tube was added 2-(6-iodo-pyrazin-2-yl)-4-methyl-thiazole-5-carboxylic acid 4-fluoro-benzylamide (100 mg, 0.22 mmol, 1.0 equiv), 4-fluoro-N-methyl-benzylamine (58 μL, 0.44 mmol, 2.0 equiv), diisopropylethylamine (17 μL, 0.44 mmol, 2.0 equiv) and dimethyl acetamide (1 mL). The reaction mixture was stirred at 100° C. After 5 hr, the reaction mixture was cooled to room temperature and diluted with dichloromethane, washed with water, brine, dried ($Na_2SO_4$), filtered and concentrated in vacuo. The crude product was purified by column chromatography [$SiO_2$, ethyl acetate/heptane, 10:90 to 70:30, v/v] and recrystallization from ether/pentane to afford 2-{6-[(4-fluoro-benzyl)-methyl-amino]-pyrazin-2-yl}-4-methyl-thiazole-5-carboxylic acid 4-fluoro-benzylamide (45 mg, 44%). $^1$H NMR (400 MHz, $CD_2Cl_2$) δ 8.57 (s, 1H), 8.06 (s, 1H), 7.24-7.34 (m, 4H), 6.98-7.05 (m, 4H), 6.18 (bs, 1H), 4.80 (s, 2H), 4.54 (d, J=8.0 Hz, 2H), 3.13 (s, 3H), 2.70 (s, 3H); HRMS $(M+H)^+$=466.15.

Example 15

Synthesis of 4-methyl-2-[6-(3-phenethyl-pyrrolidin-1-yl)-pyrazin-2-yl]-thiazole-5-carboxylic acid 4-fluoro-benzylamide

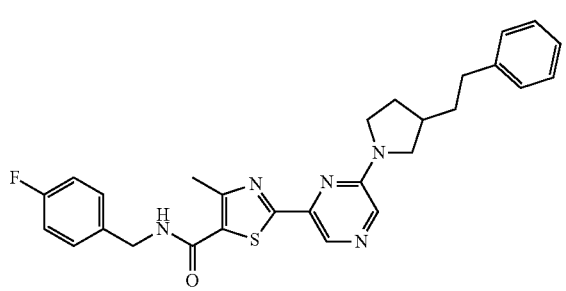

Following the procedure described in Example 14, making variations as required to replace 4-fluoro-N-methyl-benzylamine with 3-phenethyl-pyrrolidine to react with 2-(6-iodo-pyrazin-2-yl)-4-methyl-thiazole-5-carboxylic acid 4-fluoro-benzylamide, the title compound was obtained in 75% yield. $^1$H NMR (400 MHz, $CD_2Cl_2$) δ 8.50 (s, 1H), 7.89 (s, 1H), 7.31-7.38 (m, 2H), 7.24-7.30 (m, 2H), 7.14-7.23 (m, 3H), 7.00-7.09 (m, 2H), 6.18 (bs, 1H), 4.55 (d, J=4.0 Hz, 2H), 3.70-3.78 (m, 1H), 3.62-3.69 (m, 1H), 3.39-3.48 (m, 1H), 3.06-3.13 (m, 1H), 2.70 (s, 3H), 2.68-2.75 (m, 2H), 2.27-2.38 (m, 1H), 2.15-2.26 (m, 1H), 1.64-1.86 (m, 3H); MS (ES+) m/z 502.3 (M+1), $R_t$=138 min.

Example 16

Synthesis of 4-methyl-2-{6-[methyl-(3-phenyl-propyl)-amino]-pyrazin-2-yl}-thiazole-5-carboxylic acid 4-fluoro-benzylamide

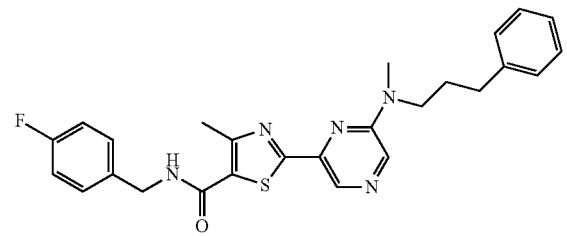

Following the procedure described in Example 14, making variations as required to replace 4-fluoro-N-methyl-benzylamine with methyl-(3-phenyl-propyl)-amine to react with 2-(6-iodo-pyrazin-2-yl)-4-methyl-thiazole-5-carboxylic acid 4-fluoro-benzylamide, the title compound was obtained in 70% yield. $^1$H NMR (400 MHz, $CD_2Cl_2$) δ 8.49 (s, 1H), 7.99 (s, 1H), 7.31-7.38 (m, 2H), 7.09-7.28 (m, 5H), 7.00-7.08 (m, 2H), 6.17 (bs, 1H), 4.56 (d, J=8.0 Hz, 2H), 3.57-3.64 (m, 2H), 3.10 (s, 3H), 2.69 (s, 3H), 2.64-2.71 (m, 2H), 1.91-2.01 (m, 2H); MS (ES+) m/z 476.2 (M+1), $R_t$=1.69 min.

Example 17

Synthesis of 2-{6-[(4-difluoromethoxy-benzyl)-methyl-amino]-pyrazin-2-yl}-4-methyl-thiazole-5-carboxylic acid 4-fluoro-benzylamide

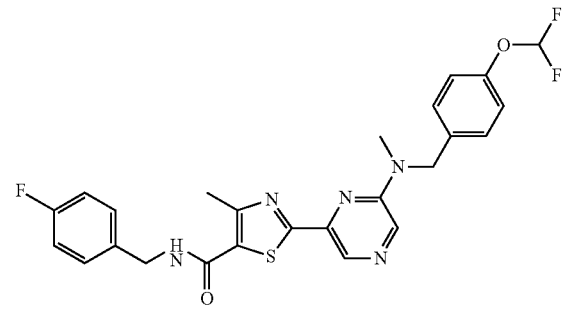

Following the procedure described in Example 14, making variations as required to replace 4-fluoro-N-methyl-benzylamine with (4-difluoromethoxy-benzyl)-methyl-amine to react with 2-(6-iodo-pyrazin-2-yl)-4-methyl-thiazole-5-carboxylic acid 4-fluoro-benzylamide, the title compound was obtained in 80% yield. $^1$H NMR (400 MHz, CD$_2$Cl$_2$) δ 8.58 (s, 1H), 8.07 (s, 1H), 7.26-7.37 (m, 4H), 7.00-7.11 (m, 4H), 6.51 (bt, J=76, 64 Hz, 1H, CH—F signal), 6.16 (bs, 1H), 4.82 (s, 2H), 4.54 (d, J=8.0 Hz, 2H), 3.14 (s, 3H), 2.70 (s, 3H); MS (ES+) m/z 514.2 (M+1), R$_t$=1.63 min.

Example 18

Synthesis of 2-(6-{[2-(4-methoxy-phenoxy)-ethyl]-methyl-amino}-pyrazin-2-yl)-4-methyl-thiazole-5-carboxylic acid 4-fluoro-benzylamide

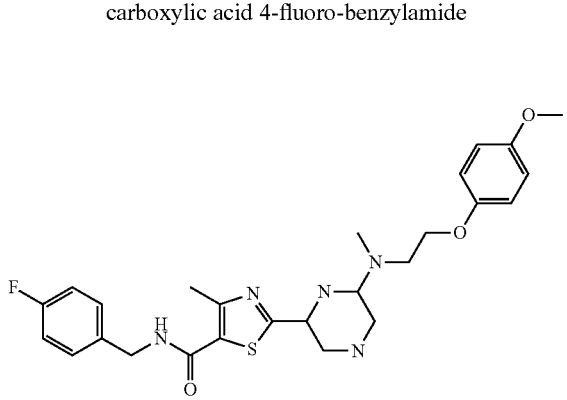

Following the procedure described in Example 14, making variations as required to replace 4-fluoro-N-methyl-benzylamine with [2-(4-methoxy-phenoxy)-ethyl]-methyl-amine to react with 2-(6-iodo-pyrazin-2-yl)-4-methyl-thiazole-5-carboxylic acid 4-fluoro-benzylamide, the title compound was obtained in 80% yield. $^1$H NMR (400 MHz, CD$_2$Cl$_2$) δ 8.50 (s, 1H), 8.04 (s, 1H), 7.31-7.38 (m, 2H), 7.02-7.09 (m, 2H), 6.72-6.82 (m, 4H), 6.25 (bs, 1H), 4.55-4.59 (m, 2H), 4.18-4.23 (m, 2H), 4.01-4.08 (m, 2H), 3.69 (s, 3H), 3.31 (s, 3H), 2.71 (s, 3H); MS (ES+) m/z 508.2 (M+1), R$_t$=1.57 min.

Example 19

Synthesis of 4-methyl-2-{6-[methyl-(2-pyridin-2-yl-ethyl)-amino]-pyrazin-2-yl}-thiazole-5-carboxylic acid 4-fluoro-benzylamide

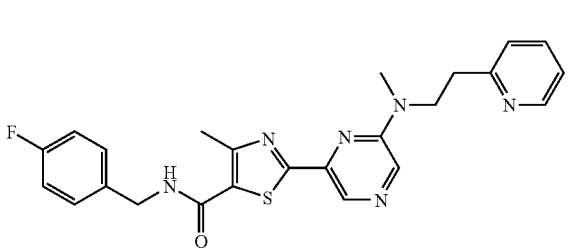

Following the procedure described in Example 14, making variations as required to replace 4-fluoro-N-methyl-benzylamine with methyl-(2-pyridin-2-yl-ethyl)-amine to react with 2-(6-iodo-pyrazin-2-yl)-4-methyl-thiazole-5-carboxylic acid 4-fluoro benzylamide, the title compound was obtained in 75% yield. $^1$H NMR (400 MHz, CD$_2$Cl$_2$) δ 8.40-8.52 (m, 2H), 8.03 (s, 1H), 7.36-7.43 (m, 3H), 7.11-7.35 (m, 3H), 7.00-7.10 (m, 2H), 4.55 (d, J=4.0 Hz, 2H), 4.00-4.15 (m, 2H), 3.15-3.40 (m, 2H), 3.12 (bs, 3H), 2.70 (s, 3H); MS (ES+) m/z 463.1 (M+1), R$_t$=1.39 min.

Example 20

Synthesis of 4-methyl-2-[6-(methyl-pyridin-3-ylmethyl-amino)-pyrazin-2-yl]-thiazole-5-carboxylic acid 4-fluoro-benzylamide

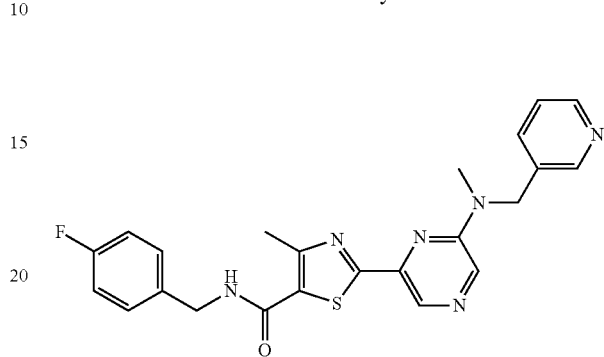

Following the procedure described in Example 14, making variations as required to replace 4-fluoro-N-methyl-benzylamine with methyl-pyridin-3-ylmethyl-amine to react with 2-(6-iodo-pyrazin-2-yl)-4-methyl-thiazole-5-carboxylic acid 4-fluoro benzylamide, the title compound was obtained in 78% yield. $^1$H NMR (400 MHz, CD$_2$Cl$_2$) δ 8.58-8.65 (m, 2H), 8.45-8.49 (m, 1H), 8.11 (s, 1H), 7.62-7.68 (m, 1H), 7.29-7.37 (m, 2H), 7.22-7.28 (m, 1H), 6.98-7.08 (m, 2H), 6.35 (bs, 1H), 4.84 (s, 2H), 4.54 (d, J=8.0 Hz, 2H), 3.18 (s, 3H), 2.69 (s, 3H); MS (ES+) m/z 449.2 (M+1), R$_t$=1.32 min.

Example 21

Synthesis of 4-methyl-2-[6-(methyl-pyridin-4-ylmethyl-amino)-pyrazin-2-yl]-thiazole-5-carboxylic acid 4-fluoro-benzylamide

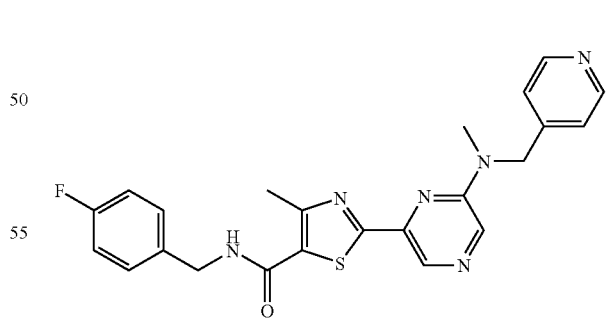

Following the procedure described in Example 14, making variations as required to replace 4-fluoro-N-methyl-benzylamine with methyl-pyridin-4-ylmethyl-amine to react with 2-(6-iodo-pyrazin-2-yl)-4-methyl-thiazole-5-carboxylic acid 4-fluoro-benzylamide, the title compound was obtained in 78% yield. $^1$H NMR (400 MHz, CD$_2$Cl$_2$) δ 8.63 (s, 1H), 8.51 (d, J=8.0 Hz, 2H), 8.14 (s, 1H), 7.27-7.36 (m, 4H), 6.99-7.08 (m, 2H), 6.18 (bs, 1H), 4.86 (s, 2H), 4.54 (d, J=4.0 Hz, 2H), 3.21 (s, 3H), 2.68 (s, 3H); MS (ES+) m/z 449.2 (M+1), $R_t$=1.30 min.

Example 22

Synthesis of 2-{6-[(4-methoxy-benzyl)-methyl-amino]-pyrazin-2-yl}-4-methyl-thiazole-5-carboxylic acid 4-fluoro-benzylamide

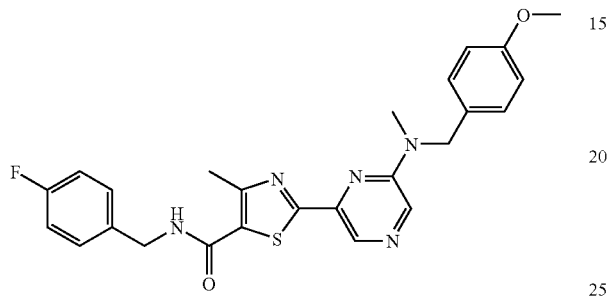

Following the procedure described in Example 14, making variations as required to replace 4-fluoro-N-methyl-benzylamine with (4-methoxy-benzyl)-methyl-amine to react with 2-(6-iodo-pyrazin-2-yl)-4-methyl-thiazole-5-carboxylic acid 4-fluoro benzylamide, the title compound was obtained in 72% yield. $^1$H NMR (400 MHz, $CD_2Cl_2$) δ 8.55 (s, 1H), 8.06 (s, 1H), 7.29-7.37 (m, 2H), 7.17-7.24 (m, 2H), 6.99-7.07 (m, 2H), 6.80-6.87 (m, 2H), 6.20 (bs, 1H), 4.75 (s, 2H), 4.53 (d, J=4.0 Hz, 2H), 3.74 (s, 3H), 3.11 (s, 3H), 2.70 (s, 3H); MS (ES+) m/z 478.2 (M+1), $R_t$=1.58 min.

Example 23

Synthesis of 2-{6-[(3-methoxy-benzyl)-methyl-amino]-pyrazin-2-yl}-4-methyl-thiazole-5-carboxylic acid 4-fluoro-benzylamide

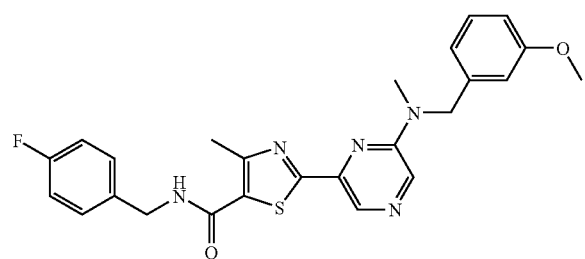

Following the procedure described in Example 14, making variations as required to replace 4-fluoro-N-methyl-benzylamine with (3-methoxy-benzyl)-methyl-amine to react with 2-(6-iodo-pyrazin-2-yl)-4-methyl-thiazole-5-carboxylic acid 4-fluoro benzylamide, the title compound was obtained in 75% yield. $^1$H NMR (400 MHz, $CD_2Cl_2$) δ 8.55 (s, 1H), 8.07 (s, 7.27-7.37 (M, 2H), 7.18-7.26 (m, 1H), 6.90-7.08 (m, 2H), 6.70-6.88 (m, 3H), 6.21 (bs, 1H), 4.79 (s, 2H), 4.53 (d, J=4.0 Hz, 2H), 3.72 (s, 3H), 3.15 (s, 3H), 2.69 (s, 3H); MS (ES+) m/z 478.2 (M+1), $R_t$=1.58 min.

Example 24

Synthesis of 2-{6-[2-(4-fluoro-phenyl)-ethyl]-pyrazin-2-yl}-4-methyl-thiazole-5-carboxylic acid 4-fluoro-benzylamide Part A. To a solution of 2-(6-iodo-pyrazin-2-yl)-4-methyl-thiazole-5-carboxylic acid 4-fluoro-benzylamide (250 mg, 0.55 mmol, 1.0 equiv) in dimethyl ether (3 mL) was added $Na_2CO_3$ (175 mg, 1.65 mmol, 3.0 equiv), trans-2-(4-fluorophenyl)vinyl boronic acid (274 mg, 1.65 mmol, 3.0 equiv), $PdCl_2$(dppf) (40 mg, 0.06 mmol, 0.1 equiv) and water (0.4 mL) in a sealed tube. The reaction vessel was immersed in an oil bath preheated to 100° C. After stirring for 12 hr, the reaction mixture was cooled and the solvent was removed in vacuo. The crude product was purified by column chromatography [$SiO_2$, methanol/dichloromethane, 0:100 to 10:90, v/v] to give 2-{6-[(E)-2-(4-fluoro-phenyl)-vinyl]-pyrazin-2-yl}-4-methyl-thiazole-5-carboxylic acid 4-fluoro-benzylamide (160 mg, 65%). MS (M+H)$^+$=449.1, $R_t$=1.64 min.

Part B. To a solution of 2-{6-[(E)-2-(4-fluoro-phenyl)-vinyl]-pyrazin-2-yl}-4-methyl-thiazole-5-carboxylic acid 4-fluoro-benzylamide (150 mg, 0.33 mmol, 1.0 equiv) in ethyl acetate/ethanol (1:1) was added Pd/C (70 mg, 10%). The flask was first purged with nitrogen, then with hydrogen in a Parr apparatus. The reaction mixture was stirred at ambient temperature for 12 hr at 50 psi. Upon completion by LCMS, the reaction mixture was diluted with ethyl acetate, filtered through Celite and concentrated in vacuo. The crude product was purified by preparative HPLC (acetonitrile/water, 0.1% trifluoroacetic acid) to afford 2-{6-[2-(4-fluoro-phenyl)-ethyl]-pyrazin-2-yl}-4-methyl-thiazole-5-carboxylic acid 4-fluoro-benzylamide (113 mg, 75%). $^1$H NMR (400 MHz, $CD_2Cl_2$) δ 9.15 (s, 1H), 8.36 (s, 1H), 7.33-7.37 (m, 2H), 7.13-7.16 (m, 2H), 7.03-7.08 (m, 2H), 6.92-6.96 (m, 2H), 6.20 (bs, 1H), 4.56 (d, J=4.0 Hz, 2H), 3.08-3.14 (m, 4H), 2.72 (s, 3H); HRMS (M+H)+=451.15.

Example 25

Synthesis of 2-(6-{[2-(4-fluoro-phenoxy)-ethyl]-methyl-amino}-pyrazin-2-yl)-4-methyl-thiazole-5-carboxylic acid benzylamide

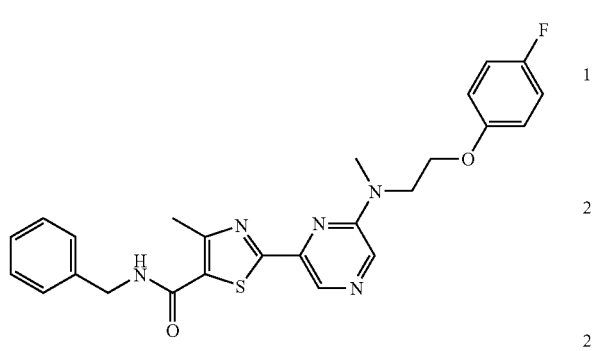

Part A. Following the procedure described in Example 1 (Part B), making variations as required to replace 2-bromo-4-methyl-thiazole-5-carboxylic acid benzylamide with 2-bromo-4-methyl-thiazole-5-carboxylic acid ethyl ester to afford 2-(6-chloro-pyrazin-2-yl)-4-methyl-thiazole-5-carboxylic acid ethyl ester in 20% yield.

Part B. To a sealed tube was added 2-(6-chloro-pyrazin-2-yl)-4-methyl-thiazole-5-carboxylic acid ethyl ester (250 mg, 0.88 mmol, 1.0 equiv), 2-(4-fluoro-phenoxy)-ethyl]-methyl-amine (298 mg, 136 mmol, 2.0 equiv), diisopropyl ethylamine (0.3 mL, 136 mmol, 2.0 equiv) and dimethyl acetamide (2.5 mL). The reaction mixture was stirred at 100° C. After 6 hr, the reaction mixture was cooled to room temperature, diluted with $CH_2Cl_2$, washed with water and brine, then dried ($Na_2SO_4$), filtered, and concentrated, in vacuo. The residue was purified by column chromatography to give 2-(6-{[2-(4-fluoro-phenoxy)-ethyl]-methyl-amino}-pyrazin-2-yl)-4-methyl-thiazole-5-carboxylic acid ethyl ester (220 mg, 60%).

Part C. To a solution of 2-(6-{[2-(4-fluoro-phenoxy)-ethyl]-methyl-amino}-pyrazin-2-yl)-4-methyl-thiazole-5-carboxylic acid ethyl ester (220 mg, 0.53 mmol) in tetrahydrofuran (8 mL) was added 1N NaOH (8 mL). The resulting reaction mixture was heated to reflux for 14 hr. The solvent was removed in vacuo, and the residue was neutralized to pH 4-5 with 10% HCl. The resulting precipitate was filtered and dried to afford 2-(6-{[2-(4-fluoro-phenoxy)-ethyl]-methyl-amino}-pyrazin-2-yl)-4-methyl-thiazole-5-carboxylic acid in 92% yield.

Part D. Following the procedure described in Example 1 (Part A), making variations as required to replace 2-bromo-4-methyl-thiazole-5-carboxylic acid with 2-(6-{[2-(4-fluoro-phenoxy)-ethyl]-methyl-amino}-pyrazin-2-yl)-4-methyl-thiazole-5-carboxylic acid, the title compound was obtained in 75% yield. $^1$H NMR (400 MHz, $CD_2Cl_2$) δ 8.55 (s, 1H), 8.12 (s, 1H), 7.36 (s, 4H), 7.27-7.35 (m, 1H), 6.90-6.97 (m, 2H), 6.79-6.84 (m, 21-1), 6.18 (bs, 1H), 4.59 (d, J=8.0 Hz, 2H), 4.17-4.22 (m, 2H), 3.97-4.02 (m, 2H), 3.25 (s, 3H), 2.71 (s, 3H); MS (ES+) m/z 478.2 (M+1), $R_t$=1.60 min.

Example 26

Synthesis of 2-(6-{[2-(4-fluoro-phenoxy)-ethyl]-methyl-amino}-pyrazin-2-yl)-4-methyl-thiazole-5-carboxylic acid (pyridin-3-ylmethyl)-amide

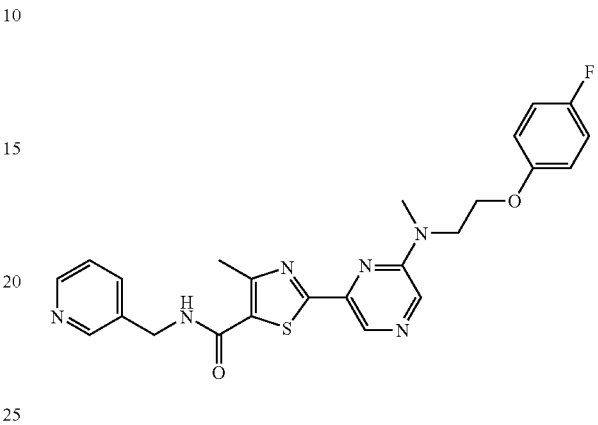

Following the procedure described in Example 1 (Part A), making variations as required to replace benzylamine with 3-(aminomethyl)-pyridine to react with 2-(6-{[2-(4-fluoro-phenoxy)-ethyl]-methyl-amino}-pyrazin-2-yl)-4-methyl-thiazole-5-carboxylic acid, the title compound was obtained in 85% yield. $^1$H NMR (400 MHz, $CD_2Cl_2$) δ 8.51 (s, 1H), 8.47-8.62 (m, 2H), 8.12 (s, 1H), 7.67-7.73 (m, 1H), 7.25-7.30 (m, 1H), 6.90-6.96 (m, 2H), 6.78-6.84 (m, 2H), 6.31 (bs, 1H), 4.59 (d, J=4.0 Hz, 2H), 4.16-4.21 (m, 2H), 3.95-4.01 (m, 2H), 3.23 (s, 3H), 2.70 (s, 3H); MS (ES+) m/z 479.2 (M+1), $R_t$=1.36 min.

Example 27

Synthesis of 2-{6-[(4-fluoro-benzyl)-methyl-amino]-pyrazin-2-yl}-4-methyl-thiazole-5-carboxylic acid (pyridin-3-ylmethyl)-amide

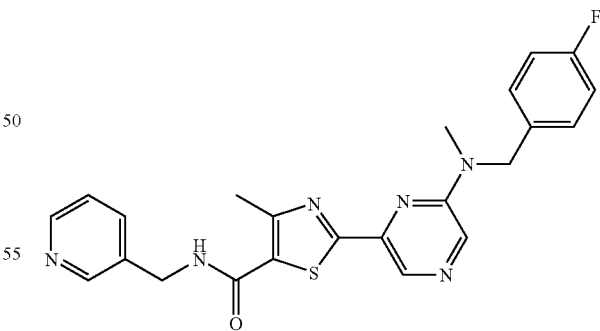

Part A. Following the procedure described in Example 25 (Part B), making variations as required to replace 2-(4-fluoro-phenoxy)-ethyl]-methyl-amine with 4-fluoro-N-methyl-benzylamine to give 2-{6-[(4-fluoro-benzyl)-methyl-amino]pyrazin-2-yl}-4-methyl-thiazole-5-carboxylic acid ethyl ester in 66% yield.

Part B. Following the procedure described in Example 25 (Part C), making variations as required to replace 2-(6-{[2-

(4-fluoro-phenoxy)-ethyl]methyl-amino}-pyrazin-2-yl)-4-methyl-thiazole-5-carboxylic acid ethyl ester with 2-{6-[(4-fluoro-benzyl)-methyl-amino]-pyrazin-2-yl}-4-methyl-thiazole-5-carboxylic acid ethyl ester to give 2-{6-[(4-fluoro-benzyl)-methyl-amino]-pyrazin-2-yl}-4-methyl-thiazole-5-carboxylic acid in 90% yield.

Part C. Following the procedure described in Example 1 (Part A), making variations as required to replace benzylamine with 3-(aminomethyl)-pyridine to react with 2-{6-[(4-fluoro-benzyl)-methyl-amino]-pyrazin-2-yl}-4-methyl-thiazole-5-carboxylic acid, the title compound was obtained in 82% yield. $^1$H NMR (400 MHz, CD$_2$Cl$_2$) δ 8.55-8.60 (m, 2H), 8.48 (d, J=4.0 Hz, 1H), 8.06 (s, 1H), 7.65-7.70 (m, 1H), 7.21-7.28 (m, 3H), 6.95-7.02 (m, 2H), 6.25 (bs, 1H), 4.78 (s, 2H), 4.56 (d, J=4.0 Hz, 2H), 3.11 (s, 3H), 2.69 (s, 3H); MS (ES+) m/z 449.2 (M-1-1), R$_t$=1.33 min.

Example 28

Synthesis of 2-{6-[(4-fluoro-benzyl)-methyl-amino]-pyrazin-2-yl}-4-methyl-thiazole-5-carboxylic acid cyclopropylmethyl-amide

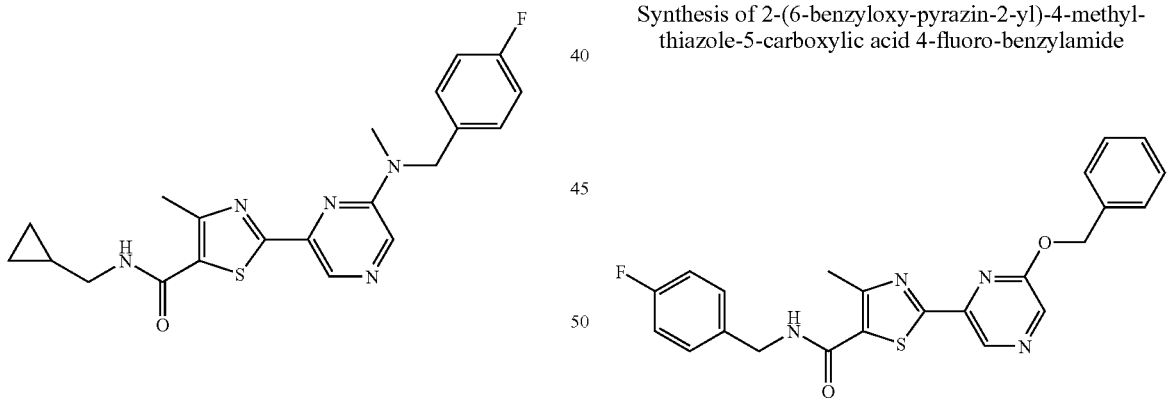

Following the procedure described in Example 1 (Part A), making variations as required to replace benzylamine with cyclopropane-methyl-amine to react with 2-{6-[(4-fluoro-benzyl)-methyl-amino]-pyrazin-2-yl}-4-methyl-thiazole-5-carboxylic acid, the title compound was obtained in 75% yield. $^1$H NMR (400 MHz, CD$_2$Cl$_2$) δ 8.58 (s, 1H), 8.05 (s, 1H), 7.25-7.31 (m, 2H), 6.98-7.05 (m, 2H), 5.95 (bs, 1H), 4.82 (s, 2H), 3.21-3.26 (m, 2H), 3.15 (s, 3H), 2.70 (s, 3H), 1.00-1.10 (m, 1H), 0.50-0.57 (m, 2H), 0.22-0.28 (m, 2H); MS (ES+) m/z 412.3 (M+1), R$_t$=1.52 min.

Example 29

Synthesis of 2-{6-[(4-fluoro-benzyl)-methyl-amino]-pyrazin-2-yl}-4-methyl-thiazole-5-carboxylic acid benzylamide

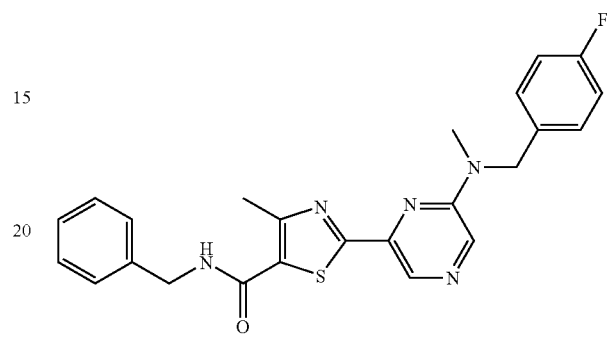

Following the procedure described in Example 1 (Part A), making variations as required to replace 2-bromo-4-methyl-thiazole-5-carboxylic acid with 2-{6-[(4-fluoro-benzyl)-methyl-amino]-pyrazin-2-yl}-4-methyl-thiazole-5-carboxylic acid, the title compound was obtained in 75% yield. $^1$H NMR (400 MHz, CD$_2$Cl$_2$) δ 8.57 (s, 1H), 8.06 (s, 1H), 7.35 (s, 5H), 7.22-7.31 (m, 2H), 6.94-7.04 (m, 2H), 6.18 (bs, 1H), 4.80 (s, 2H), 4.57 (d, J=4.0 Hz, 2H), 3.14 (s, 3H), 2.70 (s, 3H); MS (ES+) m/z 448.2 (M+1), R$_t$=1.59 min.

Example 30

Synthesis of 2-(6-benzyloxy-pyrazin-2-yl)-4-methyl-thiazole-5-carboxylic acid 4-fluoro-benzylamide To a solution of benzyl alcohol (25 μL, 0.24 mmol) in dimethyl acetamide (0.5 mL) in the sealed tube was added NaH (10.4 mg, 0.26 mmol). The reaction mixture was stirred at room temperature. After 30 min, a solution of 2-(6-iodo-pyrazin-2-yl)-4-methyl-thiazole-5-carboxylic acid 4-fluoro-benzylamide (100 mg, 0.22 mmol) and diisopropyl ethylamine (96 μL, 0.55 mmol) was added to the reaction mixture. The reaction mixture was stirred at 100° C. After 12 hr, the reaction mixture was cooled to room temperature, quenched with methanol, diluted with CH$_2$Cl$_2$, washed with water and brine, then dried (Na$_2$SO$_4$), filtered, and concentrated in vacuo. The residue was purified by column chromatography to give the title compound in 60% yield. $^1$H NMR (400 MHz, CD$_2$Cl$_2$) δ 8.92 (s, 1H), 8.29 (s, 1H), 7.47-7.51 (m, 2H), 7.31-7.40 (m, 5H), 7.02-7.08 (m, 2H), 6.20 (bs, 1H), 5.44 (s, 2H), 4.57 (d, J=8.0 Hz, 2H), 2.72 (s; 3H); MS (ES+) m/z 435.2 (M+1), R$_t$=1.65 min.

Example 31

Synthesis of 2-bromo-4-methyl-thiazole-5-carboxylic acid benzylamide

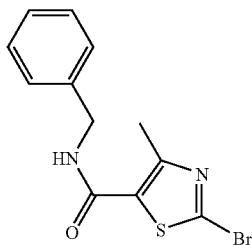

To a solution of 2-bromo-4-methyl-thiazole-5-carboxylic acid (3.00 g, 13.5 mmol) in methylene chloride (20 mL) was added benzyl amine (1.60 mL, 14.9 mmol), benzotriazol-1-yloxytris(dimethylamino)phosphonium hexafluorophosphate (BOP reagent, 6.57 g, 14.86 mmol) and N,N-diisopropylethylamine (4.71 mL; 27.02 mmol) and the mixture was stirred under nitrogen at room temperature for 16 hr. The reaction mixture was diluted with methylene chloride (100 mL), washed with water (100 mL) and brine (2×100 mL). The organic phase was dried (Na$_2$SO$_4$) and evaporated. The residue was purified by flash chromatography (hexanes:ethyl acetate, 1:1) to provide 2-bromo-4-methyl-thiazole-5-carboxylic acid benzyl amide (3.50 g, 83% yield) as a yelloW solid. $^1$H NMR (400 MHz, CDCl$_3$) δ 7.47-7.55 (m, 5H), 6.25 (bs, 1H), 4.75 (d, J=8.0 Hz, 2H), 2.79 (s, 3H); MS (M+H)$^+$= 312.1; R$_t$=1.31 min.

Example 32

Synthesis of 4-methyl-2-(2H-pyrazol-3-yl)-thiazole-5-carboxylic acid benzylamide

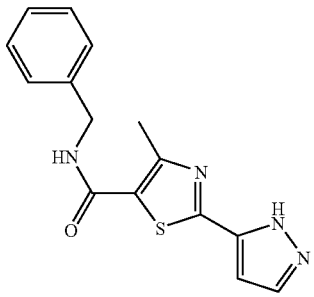

To a solution of 2-bromo-4-methyl-thiazole-5-carboxylic acid benzyl amide (2.0 g, 6.43 mmol) in toluene (30 mL), water (10 mL) and ethanol (10 mL) was added 1H-pyrazole-5-boronic acid (1.44 g, 12.9 mmol), Pd(PPh$_3$)$_4$ (0.74 g, 0.643 mmol), and potassium carbonate (2.67 g, 19.3 mmol). The resulting mixture was degassed three times and heated to 100° C. for 16 hr. The reaction mixture was cooled to room temperature, diluted with ethyl acetate (100 mL), and washed with brine (2×100 mL). The organic phase was dried (Na$_2$SO$_4$) and evaporated. The residue was purified by preparative thin layer chromatography over silica gel (ethyl acetate:hexane, 1:1) to provide 4-methyl-2-(2H-Pyrazol-3-yl)-thiazole-5-carboxylic acid benzylamide (1.25 g, 66% yield) as a white solid. $^1$H NMR (400 MHz, DMSO-d$_6$) δ 8.76 (t, J=4.0 Hz, 1H), 7.89 (d, J=4.0 Hz, 1H), 7.31-7.36 (m, 4H), 7.24-7.27 (m, 1H), 6.78 (d, J=4.0 Hz, 1H), 4.44 (d, J=4.0 Hz, 2H), 2.60 (s, 3H); MS (M+H)$^+$=299.1; R$_t$=1.06 min; HRMS (M+H)$^+$=299.10.

Example 33

Synthesis of 4-methyl-2-[1-(2-pyridin-2-yl-ethyl)-1H-pyrazole-3-yl]-thiazole-5-carboxylic acid benzylamide

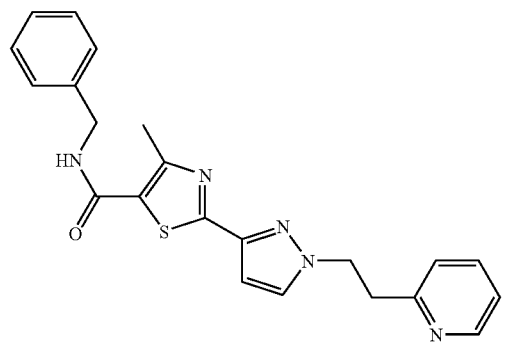

A solution of 4-methyl-2-(2H-pyrazol-3-yl)-thiazole-5-carboxylic acid benzylamide (0.1 g, 0.33 mmol) in dimethyl sulfoxide (5 mL) was treated with 2-(2-bromo-ethyl)-pyridine (0.089 g, 0.33 mmol) and potassium carbonate (0.140 g, 1.0 mmol), and the reaction mixture was heated to 90° C. for 16 hr. The reaction mixture was cooled to room temperature, diluted with ethyl acetate (50 mL), and washed with brine (2×50 mL). The organic phase was dried (Na$_2$SO$_4$) and evaporated. The residue, was purified by preparative thin layer chromatography over silica gel eluting with (5% methanol, 95% methylene chloride) to provide 4-methyl-2-[1-(2-pyridin-2-yl-ethyl)-1H-pyrazole-3-yl]-thiazole-5-carboxylic acid benzylamide (56 mg, 43% yield) as a white solid. $^1$H NMR (400 MHz, CDCl$_3$) δ 8.56 (d, J=4.0 Hz, 1H), 7.50-7.57 (m, 1H), 7.29-7.42 (m, 5H), 7.21 (s, 1H), 7.12-7.19 (m, 1H), 6.98 (d, J=8.0 Hz, 1H), 6.68 (s, 1H), 6.01 (bs, 1H), 4.62 (d, J=8.0 Hz, 2H), 4.61 (t, J=8.0 Hz, 2H), 3.36 (t, J=8.0 Hz, 2H), 2.75 (s, 3H); MS (M+H)⁺=404.2; $R_t$=1.25 min; HRMS (M+H)⁺=404.15.

Example 34

Synthesis of 4-methyl-2-(1-phenethyl-1H-pyrazol-3-yl)-thiazole-5-carboxylic acid benzylamide

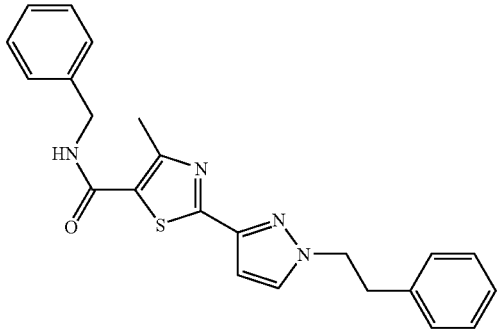

The title compound was made from 4-methyl-2-(2H-pyrazol-3-yl)-thiazole-5-carboxylic acid benzylamide and (2-bromo-ethyl)-benzene as described in Example 33 and isolated as a white solid (55 mg, 40% yield): ¹H NMR (400 MHz, CDCl₃) δ 7.22-7.39 (m, 8H), 7.16 (d, J=4 Hz, 1H), 7.07-7.09 (m, 2H), 6.72 (d, J=4 Hz, 1H), 6.02 (bs, 1H), 4.62 (d, J=8.0 Hz, 2H), 4.37 (t, J=8.0 Hz, 2H), 3.19 (t, J=8.0 Hz, 2H), 2.76 (s, 3H); MS (M+H)⁺=403.2; $R_t$=1.52 min; HRMS (M+H)⁺=403.16.

Example 35

Synthesis of 2-{1-[2-(4-fluoro-phenyl)-ethyl]-1H-pyrazol-3-yl}-4-methyl-thiazole-5-carboxylic acid benzylamide

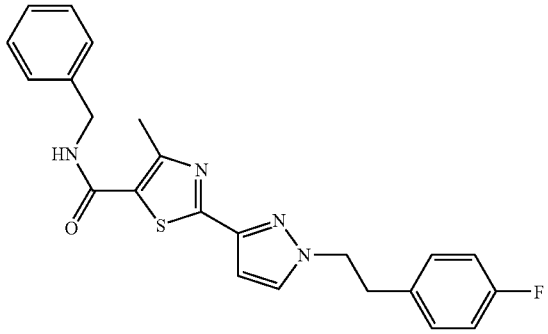

The title compound was made from 4-methyl-2-(2H-pyrazol-3-yl)-thiazole-5-carboxylic acid benzylamide and 1-(2-bromo-ethyl)-4-fluoro-benzene as described in Example 33 and isolated as a white solid (62 mg, 44% yield). ¹H NMR (400 MHz, CDCl₃) δ 7.31-7.39 (m, 5H), 7.14 (d, J=4.0 Hz, 1H), 6.92-7.03 (m, 4H), 6.74 (d, J=4.0 Hz, 1H), 6.01 (bs, 1H), 4.62 (d, J=4.0 Hz, 2H), 4.34 (t, J=8.0 Hz, 2H), 3.16 (t, J=8.0 Hz, 2H), 2.76 (s, 3H); MS (M+H)⁺=421.1; $R_t$=1.49 min; HRMS (M+H)⁺=421.15.

Example 36

Synthesis of 2-{1-[2-(3-fluoro-phenyl)-ethyl]-1H-pyrazol-3-yl}-4-methyl-thiazole-5-carboxylic acid benzylamide

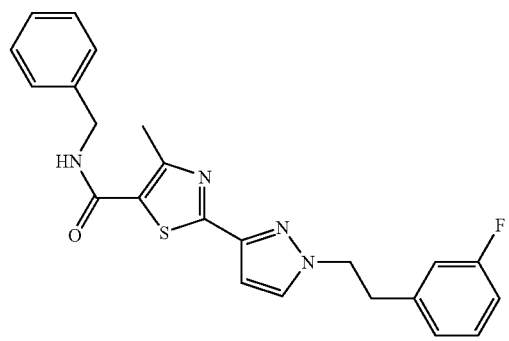

The title compound was made from 4-methyl-2-(2H-pyrazol-3-yl)-thiazole-5-carboxylic acid benzylamide and 1-(2-bromo-ethyl)-3-fluoro-benzene as described in Example 33 and isolated as a white solid (56 mg, 41% yield). ¹H NMR (400 MHz, CDCl₃) δ 7.19-7.39 (m, 6H), 7.18 (d, J=4.0 Hz, 1H), 6.91-6.94 (m, 1H), 6.78-6.84 (m, 2H), 6.72 (d, J=4.0 Hz, 1H), 6.03 (bs, 1H), 4.62 (d, J=8.0 Hz, 2H), 4.37 (t, J=8.0 Hz, 2H), 3.19 (t, J=8.0 Hz, 2H), 2.76 (s, 3H); MS (M+H)⁺=421.1; $R_t$=1.52 min; HRMS (M+H)⁺=421.15.

Example 37

Synthesis of 4-methyl-2-[1-(3-phenyl-propyl)-1H-pyrazol-3-yl]-thiazole-5-carboxylic acid benzylamide

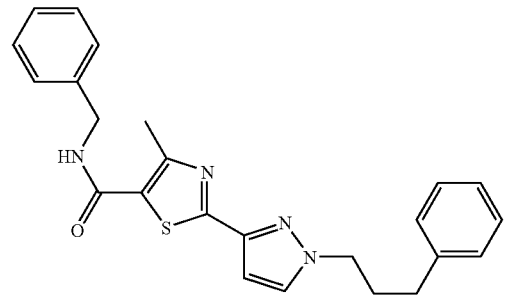

The title compound was made from 4-methyl-2-(2H-pyrazol-3-yl)-thiazole-5-carboxylic acid benzylamide and 1-(2-bromo-ethyl)-3-fluoro-benzene) as described in Example 33 and isolated as a yellow solid (65 mg, 46% yield). ¹H NMR (400 MHz, CDCl₃) δ 7.28-7.42 (m, 8H), 7.18-7.24 (m, 3H), 6.84 (d, J=4.0 Hz, 1H), 6.05 (bs, 1H), 4.64 (d, J=4.0 Hz, 2H), 4.17 (t, J=8.0 Hz, 2H), 2.78 (s, 3H), 2.66 (t, J=8.0 Hz, 2H), 2.23-2.30 (m, 2H); MS (M+H)⁺=417.2; R_t=1.58 min; HRMS (M+H)⁺=417.17

Example 38

Synthesis of 2-{1-[2-(4-methoxy-phenyl)-ethyl]-1H-pyrazol-3-yl}-4-methyl-thiazole-5-carboxylic acid benzylamide

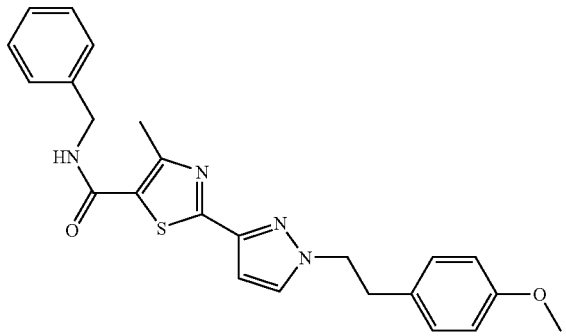

The title compound was made from 4-methyl-2-(2H-pyrazol-3-yl)-thiazole-5-carboxylic acid benzylamide and 1-(2-bromo-ethyl)-4-methoxy-benzene as described in Example 33 and isolated as a white solid (45 mg, 32% yield). ¹H NMR (400 MHz, CDCl₃) δ 7.31-7.38 (m, 5H), 7.14 (d, J=4 Hz, 2H), 6.96-6.99 (m, 2H), 6.79-6.81 (m, 2H), 6.72 (d, J=4.0 Hz, 1H), 6.02 (bs, 1H), 4.62 (d, J=8.0 Hz, 2H), 4.33 (t, J=8.0 Hz, 2H), 3.77 (s, 3H), 3.12 (t, J=8.0 Hz, 2H), 2.76 (s, 3H); MS (M+H)⁺= 433.2; R_t=1.47 min; HRMS (M+H)⁺=433.17.

Example 39

Synthesis of 2-{1-[2-(4-Hydroxy-phenyl)-ethyl]-1H-pyrazol-3-yl}-4-methyl-thiazole-5-carboxylic acid benzylamide

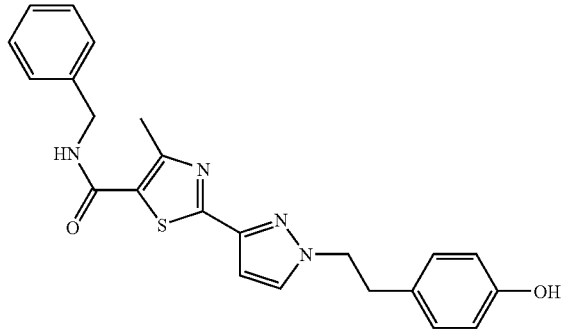

The title compound was made from 4-methyl-2-(2H-pyrazol-3-yl)-thiazole-5-carboxylic acid benzylamide and 1-(2-bromo-ethyl)-4-hydroxy-benzene as described in Example 33 and isolated as a white solid (25 mg, 18% yield). ¹H NMR (400 MHz, CDCl₃) δ 7.30-7.39 (m, 5H), 7.14 (d, J=4.0 Hz, 1H), 6.89-6.92 (m, 2H), 6.71-6.74 (m, 3H), 6.01 (bs, 1H), 4.62 (d, J=8.0 Hz, 2H), 4.32 (t, J=8 Hz, 2H), 3.11 (t, J=8.0 Hz, 2H), 2.75 (s, 3H); MS (M+H)⁺=419.1; R_t=1.30 min; HRMS (M+H)⁺=419.15.

Example 40

Synthesis of 4-methyl-2-[1-(2-phenoxy-ethyl)-1H-pyrazol-3-yl]-thiazole-5-carboxylic acid benzylamide

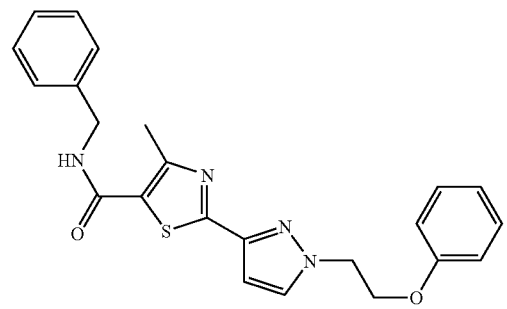

The title compound was made from 4-methyl-2-(2H-pyrazol-3-yl)-thiazole-5-carboxylic acid benzylamide and (2-bromo-ethoxy)-benzene as described in Example 33 and isolated as a white solid (75 mg, 54% yield). ¹HNMR (400 MHz, CDCl₃) δ 7.60 (d, J=4.0 Hz, 1H), 7.25-7.38 (m, 7H), 6.96 (t, J=8.0 Hz, 1H), 6.86 (d, J=8.0 Hz, 2H), 6.80 (d, J=4.0 Hz, 1H), 6.02 (bs, 1H), 4.61 (d, J=8.0 Hz, 2H), 4.55 (t, J=4.0 Hz, 2H), 4.35 J=4.0 Hz, 2H), 2.74 (s, 3H); MS (M+H)⁺= 419.2; R_t=1.48 min; HRMS (M+H)⁺=419.15.

Example 41

Synthesis of 4-methyl-2-[1-(3-methyl-butyl)-1H-pyrazol-3-yl]-thiazole-5-carboxylic acid benzylamide

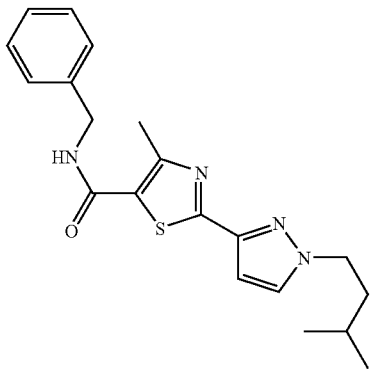

The title compound was made from 4-methyl-2-(2H-pyrazol-3-yl)-thiazole-5-carboxylic acid benzylamide and 1 bromo-3-methyl-butane as described in Example 33 and isolated as a white solid (62 mg, 53% yield). ¹NMR (400 MHz, CDCl₃) δ 7.41 (d, J=4.0 Hz, 1H), 7.30-7.38 (m, 5H), 6.80 (d, J=4.0 Hz, 1H), 6.04 (bs, 1H), 4.60 (d, J=4.0 Hz, 2H), 4.16 (t, J=8.0 Hz, 2H), 2.75 (s, 3H), 1.76-1.82 (m, 2H), 1.58-1.63 (m, 1H), 0.95 (d, J=8.0 Hz, 6H); MS (M+H)⁺=369.2; R$_t$=1.58 min; HRMS (M+H)⁺=369.17.

Example 42

Synthesis of 4-methyl-2-[1-(2-phenyl-propyl)-1H-pyrazol-3-yl]-thiazole-5-carboxylic acid benzylamide

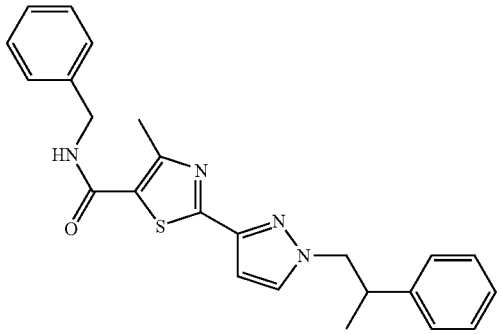

The title compound was made from 4-methyl-2-(2H-pyrazol-3-yl)-thiazole-5-carboxylic acid benzylamide and 1-bromo-3-methyl-butane as described in Example 33 and isolated as a white solid (56 mg, 40% yield). ¹H NMR (400 MHz, CDCl₃) δ 7.20-7.39 (m, 8H), 7.12-7.14 (m, 2H), 7.04 (d, J=4.0 Hz; 1H), 6.66 (d, J=4.0 Hz, 1H), 6.03 (bs, 1H), 4.62 (d, J=4.0 Hz, 2H), 4.19-4.30 (m, 2H), 3.37-3.42 (m, 1H), 2.75 (s, 3H), 1.29 (d, J=8.0 Hz, 3H); MS (M+H)⁺=417.2; R$_t$=1.60 min; HRMS (M+H)⁺=417.18.

Example 43

Synthesis of 2-[1-(2-cyclohexyl-ethyl)-1H-pyrazol-3-yl]-4-methyl-thiazole-5-carboxylic acid benzylamide

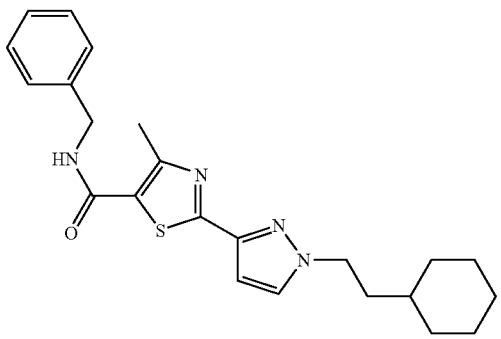

The title compound was made from 4-methyl-2-(2H-pyrazol-3-yl)-thiazole-5-carboxylic acid benzylamide and 1-bromo-3-methyl-butane as described in Example 33 isolated as a yellow solid (35 mg, 27% yield). ¹H NMR (400 MHz, CDCl₃) δ 7.42 (d, J=4.0 Hz, 1H), 7.32-7.40 (m, 5H), 6.82 (d, J=4.0 Hz, 1H), 6.07 (bs, 1H), 4.62 (d, J=4.0 Hz, 2H), 4.19 (t, J=8.0 Hz, 2H), 2.77 (s, 3H), 1.68-1.83 (m, 7H), 1.18-1.29 (m, 4H), 0.96-0.99 (m, 2H); MS (M+H)⁺=409.2; R$_t$=1.73 min; HRMS (M+H)⁺=409.21.

Example 44

Synthesis of 2-[1-((R)-2-hydroxy-2-phenyl-ethyl)-1H-pyrazol-3-yl]-4-methyl-thiazole-5-carboxylic acid benzylamide

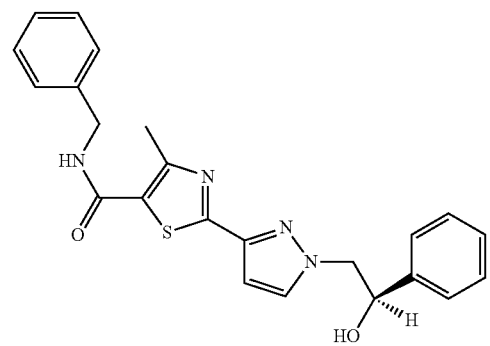

To a solution of 4-methyl-2-(2H-pyrazol-3-yl)-thiazole-5-carboxylic acid benzylamide (0.15 g, 0.50 mmol) in trifluorotoluene (5 mL) was added R-(t)-styrene oxide (0.1 mL, 1.01 mmol), cesium carbonate (0.08 g, 0.25 mmol) and the mixture was refluxed at 100° C. for 16 hr. After cooling, the reaction mixture was filtered and the filtrate was extracted with methylene chloride (50 mL). The organic phase was dried (Na₂SO₄) and evaporated. The residue was purified by preparative thin layer chromatography over silica gel (methylene chloride:methanol, 95:5) to provide 2-[1-((R)-2-hydroxy-2-phenyl-ethyl)-1H-pyrazol-3-yl]-4-methyl-thiazole-5-carboxylic acid benzylamide (17 mg, 10% yield) as a white solid. ¹H NMR (400 MHz, DMSO-d₆) δ 8.77 (bt, J=4.0 Hz, 1H), 7.80 (d, J=4.0 Hz, 1H), 7.29-7.38 (m, 8H), 7.23-7.28 (m, 2H), 6.74 (d, J=4.0 Hz, 1H), 5.74 (d, J 4.0 Hz, 1H), 4.94-5.06 (m, 1H), 4.46 (d, J=4.0 Hz, 2H), 4.31 (d, J=8.0 Hz, 2H), 2.61 (s, 3H); MS (M+H)⁺=419.2; R$_t$=4.19 min; HRMS (M+H)⁺=419.15.

Example 45

Synthesis of 2-{1-[(R)-2-(4-fluoro-phenyl)-2-hydroxy-ethyl]-1H-pyrazol-3-yl}-4-methyl-thiazole-5-carboxylic acid benzylamide

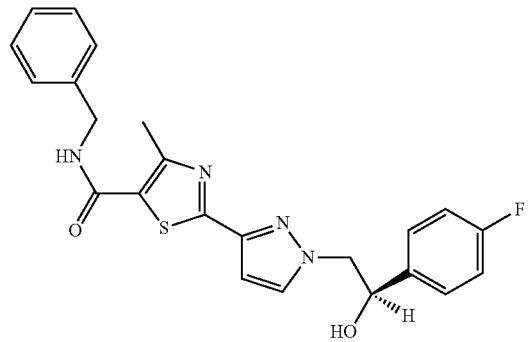

The title compound was made from 4-methyl-2-(2H-pyrazol-3-yl)-thiazole-5-carboxylic acid benzylamide and R-2-(4-fluoro-phenyl) as described above in Example 44 and isolated as a white solid (21 mg, 21% yield). $^1$H NMR (400 MHz, DMSO-d$_6$) δ 8.78 (bt, J=8.0 Hz; 1H), 7.80 (d, J=4.0 Hz, 1H), 7.34-7.42 (m, 6H), 7.26-7.29 (m, 1H), 7.15-7.21 (m, 2H), 6.74 (d, J=4.0 Hz, 1H), 5.80 (bs, 1H), 5.02 (t, J=8.0 Hz, 1H), 4.46 (d, J=4.0 Hz, 2H), 4.31 (d, J=8.0 Hz, 2H), 2.61 (s, 3H); MS (M+H)$^+$=437.1; R$_t$=1.36 min; HRMS (M+H)$^+$=437.14.

Example 46

Synthesis of 2-[1-((S)-2-hydroxy-2-phenyl-ethyl)-1H-pyrazol-3-yl]-4-methyl-thiazole-5-carboxylic acid benzylamide

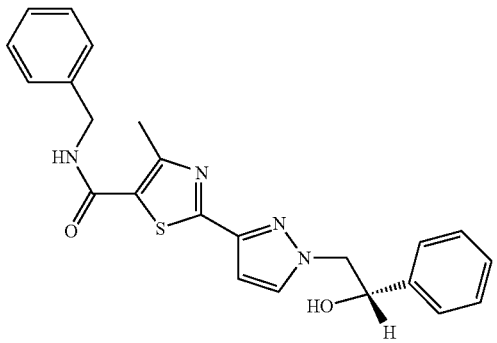

The title compound was made from 4-methyl-2-(2H-pyrazol-3-yl)-thiazole-5-carboxylic acid benzylamide and S-(t)-styrene oxide as described above in Example 44 and isolated as a white solid (15 mg, 21% yield). $^1$H NMR (400 MHz, DMSO-d$_6$) δ 8.76 (bt, J=4.0 Hz, 1H), 7.78 (d, J=4.0 Hz, 1H), 7.32-7.38 (in, 8H), 7.23-7.29 (m, 2H), 6.72 (d, J=4.0 Hz, 1H), 5.72 (d, J=4.0 Hz, 1H), 4.96-5.00 (m, 1H), 4.44 (d, J=4.0 Hz, 2H), 4.30 (d, J=4.0 Hz, 2H), 2.60 (s, 3H); MS (M+H)$^+$=419.2; R$_t$=4.19 min; HRMS (M+H)$^+$=419.16.

Example 47

Synthesis of 2-{1-[2-(4-fluoro-phenyl)-ethyl]-1H-pyrazol-3-yl}-4-methyl-thiazole-5-carboxylic acid 4-fluoro-benzylamide

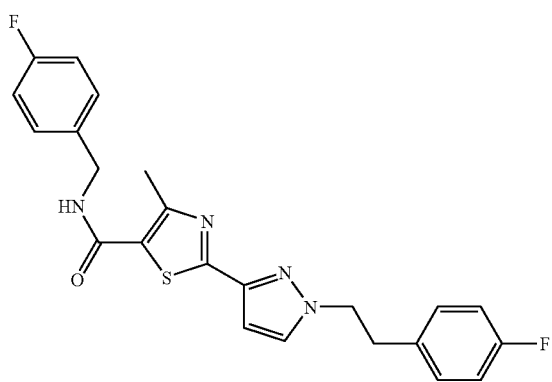

Part A. Synthesis of 4-methyl-2-(2H-pyrazol-3-yl)-thiazole-5-carboxylic acid ethyl ester To a solution of 2-bromo-4-methyl-thiazole-5-carboxylic acid ethyl ester (2.0 g, 7.99 mmol) in toluene (60 mL), water (20 mL) and ethanol (20 mL) was added 1H-pyrazole-5-boronic acid (1.79 g, 15.99 mmol), Pd(PPh$_3$)$_4$ (0.92 g, 0.80 mmol), and potassium carbonate (3.30 g, 23.98 mmol). The resulting mixture was degassed three times and heated to 100° C. for 16 hr. The reaction mixture was cooled to room temperature, diluted with ethyl acetate (200 mL) and washed with brine (2×100 mL). The organic phase was dried (Na$_2$SO$_4$) and evaporated. The residue was purified by flash column chromatography (hexanes:ethyl acetate, 1:1) to provide 4-methyl-2-(2H-pyrazol-3-yl)-thiazole-5-carboxylic acid ethyl ester (1.5 g, 83% yield) as a yellow solid. MS (M+H)$^+$=238; R$_t$=1.2 min.

Part B. Synthesis of 2-{1-[2-(4-fluoro-phenyl)-ethyl]-1H-pyrazol-3-yl}-4-methyl-thiazole-5-carboxylic acid ethyl ester A solution of 4-methyl-2-(2H-pyrazol-3-yl)-thiazole-5-carboxylic acid ethyl ester (2.5 g, 10.54 mmol) in dimethyl sulfoxide (50 mL) was treated with 1-(2-bromo-ethyl)-4-fluoro-benzene (2.10 g, 10.54 mmol) and potassium carbonate (4.30 g, 31.64 mmol), and the reaction mixture was heated to 90° C. for 16 hr. The reaction mixture was cooled to room temperature, diluted with ethyl acetate (100 mL), and washed with brine (2×100 mL). The organic phase was dried (Na$_2$SO$_4$) and evaporated. The residue was purified by flash column chromatography (hexanes:ethyl acetate, 1:1) to provide 2-{1-[2-(4-fluoro-phenyl)-ethyl]-1H-pyrazol-3-yl}-4-methyl-thiazole-5-carboxylic acid ethyl ester (1.57 g, 45% yield) as a white solid. MS (M+H)$^+$=360; R$_t$=1.65 min.

Part C. Synthesis of 2-{1-[2-(4-fluoro-phenyl)-ethyl]-1H-pyrazol-3-yl}-4-methyl-thiazole-5-carboxylic acid A mixture of 2-{1-[2-(4-fluoro-phenyl)-ethyl]-1H-pyrazol-3-yl}-4-methyl-thiazole-5-carboxylic acid ethyl ester (0.5 g, 1.39 mmol) and NaOH (0.22 g, 5.57 mmol) in tetrahydrofuran (10 mL) and water (5 mL) was heated to reflux for 16 hr. The reaction mixture was cooled to room temperature and neutralized with 5% HCl to pH 6. The precipitate was filtered and dried to provide 2-{1-[2-(4-fluoro-phenyl)-ethyl]-1H-pyrazol-3-yl}-4-methyl-thiazole-5-carboxylic acid (0.40 g, 87%) as a yellow solid. MS (M+H)$^+$=332; R$_t$=1.04 min.

Part D. Synthesis of 2-{1-[2-(4-fluoro-phenyl)-ethyl]-1H-pyrazol-3-yl}-4-methyl-thiazole-5-carboxylic acid 4-fluoro-benzylamide To a solution of 2-{1-[2-(4-fluoro-phenyl)-ethyl]-1H-pyrazol-3-yl}-4-methyl-thiazole-5-carboxylic acid (0.1 g, 0.30 mmol) in methylene chloride (5 mL) was added 4-fluoro benzyl amine (0.04 g, 0.33 mmol), benzotriazol-1-yloxytris-(dimethylamino)-phosphonium hexafluorophosphate (BOP reagent, 0.146 g, 0.33 mmol) and N,N-diisopropylethylamine (0.1 mL, 0.60 mmol) and the mixture was stirred under nitrogen at room temperature for 16 hr. The reaction mixture was diluted with methylene chloride (50 mL), washed with water (50 mL) and brine (2×50 mL). The organic phase was dried (Na$_2$SO$_4$) and evaporated. The residue was purified by preparative thin layer chromatography over silica gel (hexanes: ethyl acetate, 1:1) to provide 2-{1-[2-(4-fluoro-phenyl)- ethyl]-1H-pyrazol-3-yl}-4-methyl-thiazole-5-carboxylic acid 4-fluoro-benzylamide (83 mg, 62% yield) as a white solid. $^1$H NMR (400 MHz, CDCl$_3$) δ 7.30 (m, 2H), 7.14 (d, J=4.0 Hz, 1H), 6.92-7.07 (m, 6H), 6.72 (d, J=4.0 Hz, 1H), 6.06 (bs, 1H), 4.58 (d, J=4.0 Hz, 2H), 4.34 (t, J=8.0 Hz, 2H), 3.16 (t, J=8.0 Hz, 2H), 2.75 (s, 3H); MS (M+H)$^+$=439.1; R$_t$=1.55 min; HRMS (M+H)$^+$=439.14.

Example 48

Synthesis of 2-{1-[2-(4-fluoro-phenyl)-ethyl]-1H-pyrazol-3-yl}-4-methyl-thiazole-5-carboxylic acid (pyridin-3-ylmethyl)amide

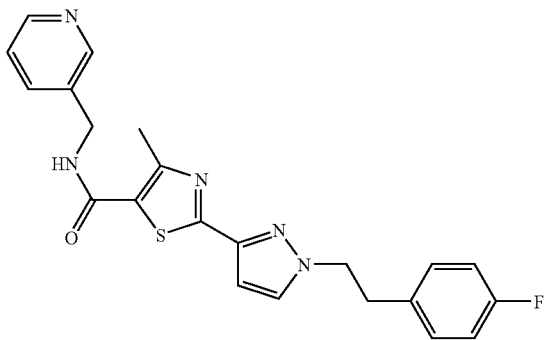

The title compound was made from 2-bromo-4-methyl-thiazole-5-carboxylic acid ethyl ester and pyridin-3-yl-methylamine as described above in Example 47 and isolated as a white solid (55 mg, 42% yield). $^1$H NMR (400 MHz, CDCl$_3$) δ 8.59 (s, 1H), 8.53-8.55 (m, 1H), 7.69-7.72 (m, 1H), 7.28-7.30 (m, 1H), 7.14 (d, J=4.0 Hz, 1H), 6.92-7.02 (m, 4H), 6.72 (d, J=4.0 Hz, 1H), 6.33 (bs, 1H), 4.62 (d, J=4.0 Hz, 2H), 4.34 (t, J=8.0 Hz, 2H), 3.16 (t, J=8.0 Hz, 2H), 2.75 (s, 3H); MS (M+H)$^+$=422.1; R$_t$=1.31 min; HRMS (M+H)$^+$=422.14.

Example 49

Synthesis of 2-[1-(4-chloro-benzyl)-1H-pyrazol-3-yl]-4-methyl-thiazole-5-carboxylic acid (pyridin-3-ylmethyl)amide

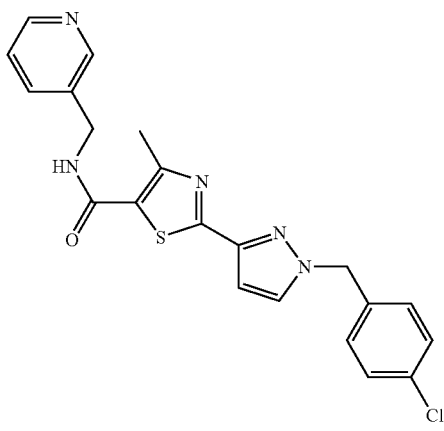

Part A. Synthesis of 2-bromo-4-methyl-thiazole-5-carboxylic acid (pyridine-3-ylmethyl)-amide To a solution of 2-bromo-4-methyl-thiazole-5-carboxylic acid (10.0 g, 45.0 mmol) in methylene chloride (200 mL) was added 3-(aminomethyl) pyridine (5.05 mL, 49.5 mmol), benzotriazol-1-yloxytris(dimethylamino)phosphonium hexafluorophosphate (BOP reagent, 21.9 g, 49.5 mmol) and N,N-diisopropylethylamine (15.7 mL, 90.1 mmol). The mixture was stirred under nitrogen at room temperature for 16 hr, then diluted with methylene chloride (300 mL), washed with water (300 mL) and brine (2×200 mL). The organic phase was dried (Na$_2$SO$_4$) and evaporated. The residue was purified by flash chromatography over silica gel (methylene chloride: methanol, 95:5) to provide 2-bromo-4-methyl-thiazole-5-carboxylic acid (pyridine-3-ylmethyl)-amide as a yellow solid (13.5 g, 96% yield). MS (M+H)$^+$=313; R$_t$=1.01 min.

Part B. Synthesis of 4-methyl-2-(2H-pyrazol-3-yl)-thiazole-5-carboxylic acid (pyridin-3-ylmethyl) amide To a solution of 2-bromo-4-methyl-thiazole-5-carboxylic acid (pyridine-3-ylmethyl)-amide (5.0 g, 16.0 mmol) in toluene (30 mL), water (10 mL) and ethanol (10 mL) was added 1H-pyrazole-5-boronic acid (2.15 g, 19.2 mmol), Pd(PPh$_3$)$_4$ (1.85 g, 1.60 mmol), and potassium carbonate (6.64 g, 48.1 mmol). The resulting mixture was degassed three times and heated to 100° C. for 16 hr. The reaction mixture was cooled to room temperature, diluted with ethyl acetate (200 mL) and washed with brine (2×100 mL). The organic phase was dried (Na$_2$SO$_4$) and evaporated. The residue was recrystallized from ethyl acetate to provide 4-methyl-2-(2H-pyrazol-3-yl)-thiazole-5-carboxylic acid (pyridine-3-ylmethyl)amide as a white solid (4.20 g, 85% yield).

Part C. Synthesis of 2-[1-(4-chloro-benzyl)-1H-pyrazol-3-yl]-4-methyl-thiazole-5-carboxylic acid (pyridin-3-ylmethyl)-amide To a solution of 4-methyl-2-(2H-pyrazol-3-yl)-thiazole-5-carboxylic acid (pyridin-3-ylmethyl)-amide (0.2 g, 0.67 mmol) in dimethyl sulfoxide (5 mL) was added with 4-chlorobenzyl bromide (0.14 g, 0.67 mmol) and potassium carbonate (0.30 g, 2.0 mmol). The reaction mixture was heated to 90° C. for 16 hr. The reaction mixture was cooled to room temperature, diluted with ethyl acetate (50 mL), and washed with brine (2×50 mL). The organic phase was dried (Na$_2$SO$_4$) and evaporated. The residue was purified by preparative thin layer chromatography over silica gel (methylene chloride: methanol, 95:5) to provide 2-[1-(4-chloro-benzyl)-1H-pyrazol-3-yl]-4-methyl-thiazole-5-carboxylic acid (pyridin-3-ylmethyl)amide as a white solid (0.071 g, 51% yield). $^1$H NMR (400 MHz, CDCl$_3$) δ 8.60 (s, 1H), 8.54-8.56 (m, 1H), 7.71 (d, J=8 Hz, 1H), 7.39 (s, 1H) 7.26-7.33 (m, 3H), 7.18 (d, J=4 Hz, 2H), 6.84 (d, J=4 Hz, 1H), 6.18-6.21 (m, 1H), 5.31 (s, 2H), 4.62 (d, J=4 Hz, 2H), 2.74 (s, 3H). MS (M+H)⁺=423.9; R$_t$=1.29 min; HRMS (M+H)⁺=424.10.

Example 50

Synthesis of 2-[1-(4-chloro-2-fluoro-benzyl)-1H-pyrazol-3-yl]-4-methyl-thiazole-5-carboxylic acid (pyridin-3-ylmethyl)amide

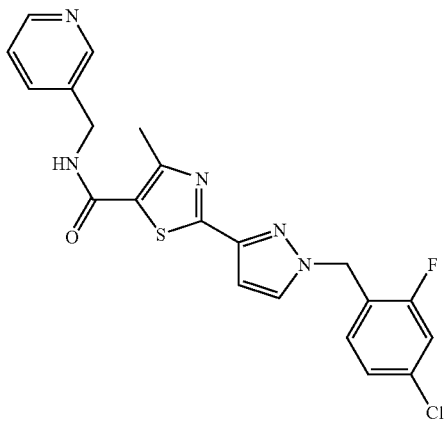

The title compound was prepared from 4-methyl-2-(2H-pyrazol-3-yl)-thiazole-5-carboxylic acid (pyridin-3-ylmethyl)-amide and 1-bromomethyl-4-chloro-2-fluoro-benzene as described in Example 49 and isolated as a white solid (0.075 g; 51% yield). ¹H NMR (400 MHz, CDCl$_3$) δ 8.61 (s, 1H), 8.56-8.58 (m, 1H), 7.71 (d, J=8 Hz, 1H), 7.46 (d, J=4 Hz, 1H), 7.26-7.31 (m, 1H), 7.10-7.17 (m, 3H), 6.85 (s, 1H), 6.07-6.15 (m, 1H), 5.36 (s, 2H), 4.62 (d, J=8 Hz, 2H), 2.75 (s, 3H). MS (M+H)⁺=442.1; R$_t$=1.35 min; HRMS (M+H)⁺=442.09.

Example 51

Synthesis of 2-[1-(4-ethyl-benzyl)-1H-pyrazol-3-yl]-4-methyl-thiazole-5-carboxylic acid (pyridin-3-ylmethyl)amide

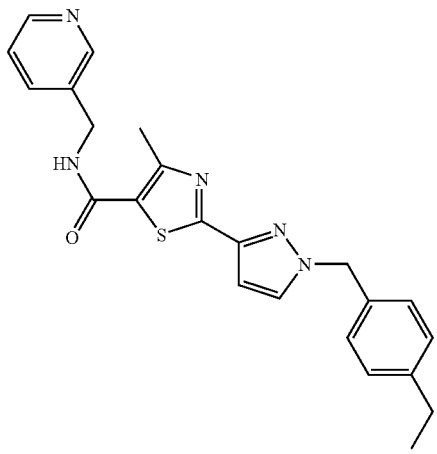

The title compound was prepared from 4-methyl-2-(2H-pyrazol-3-yl)-thiazole-5-carboxylic acid (pyridin-3-ylmethyl)-amide and 1-bromomethyl-4-ethyl-benzene as described in Example 49 and isolated as a white solid (0.056 g, 42 (% yield). ¹H NMR (400 MHz, CDCl$_3$) δ 8.61 (s, 1H), 8.52-8.58 (m, 1H), 7.72 (d, J=8 Hz, 1H), 7.06-7.48 (m, 6H), 6.80-6.84 (m, 1H), 6.08-6.15 (m, 1H), 4.63 (d, J=8 Hz, 2H), 2.75 (s, 3H), 2.61-2.70 (m, 2H), 1.13-1.26 (m, 3H); MS (M+H)⁺=418.2; R$_t$=1.38 min; HRMS (M+H)⁺=418.17.

Example 52

Synthesis of 2-[1-(4-cyano-benzyl)-1H-pyrazol-3-yl]-4-methyl-thiazole-5-carboxylic acid (pyridin-3-ylmethyl)amide

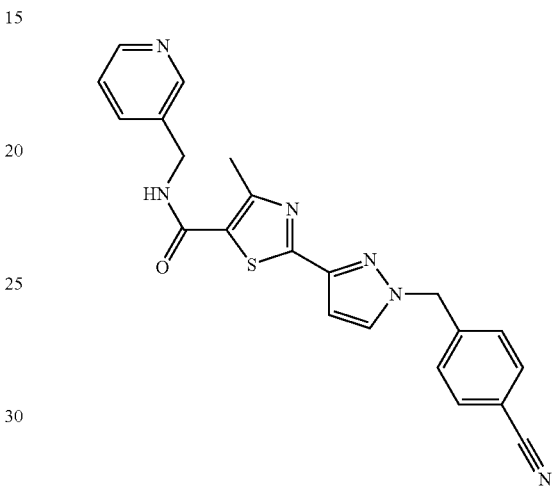

The title compound was prepared from 4-methyl-2-(2H-pyrazol-3-yl)-thiazole-5-carboxylic acid (pyridin-3-ylmethyl)-amide and 4-bromomethyl-benzonitrile as described in Example 49 and isolated as a white solid (0.065 g, 46% ¹H NMR (400 CDCl$_3$) δ 3.60 (s, 1H), 8.55-8.57 (m, 1H), 7.71 (d, J=8 Hz, 1H), 7.64 (d, J=8 Hz, 2H), 7.46 (s, 1H), 7.26-7.31 (m, 3H), 6.90 (d, J=4 Hz, 1H), 6.11-6.16 (m, 1H), 5.41 (s, 2H), 4.63 (d, J=8 Hz, 2H), 2.75 (s, 3H); MS (M+H)⁺=415.2; R$_t$=1.15 min; HRMS (M+H)⁺=415.14.

Example 53

Synthesis of 2-[1-(3-chloro-benzyl)-1H-pyrazol-3-yl]-4-methyl-thiazole-5-carboxylic acid (pyridin-3-ylmethyl)amide

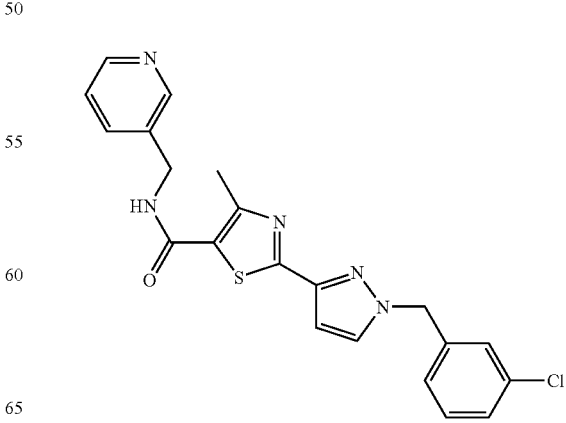

The title compound was made from 4-methyl-2-(2H-pyrazol-3-yl)-thiazole-5-carboxylic acid (pyridin-3-ylmethyl)-amide and 3-chlorobenzyl bromide as described in Example 49 and isolated as a yellow solid (0.07 g, 50% yield). $^1$H NMR (400 MHz, CDCl$_3$) δ 8.61 (s, 1H), 8.54-8.58 (m, 1H), 7.72 (d, J=8 Hz, 1H), 7.42 (d, J=4 Hz, 1H), 7.25-7.33 (m, 4H), 7.09-7.14 (m, 1H), 6.87 (d, J=2 Hz, 1H), 6.08-6.14 (m, 1H), 5.33 (s, 2H), 4.63 (d, J=4 Hz, 2H), 2.76 (s, 3H); MS (M+H)$^+$=424.1; R$_f$=1.36 min; HRMS (M+H)$^+$=424.10.

Example 54

Synthesis of 4-methyl-2-[1-(4-pyrrol-1-yl-benzyl)-1H-pyrazol-3-yl]-thiazole-5-carboxylic acid (pyridin-3-ylmethyl)amide

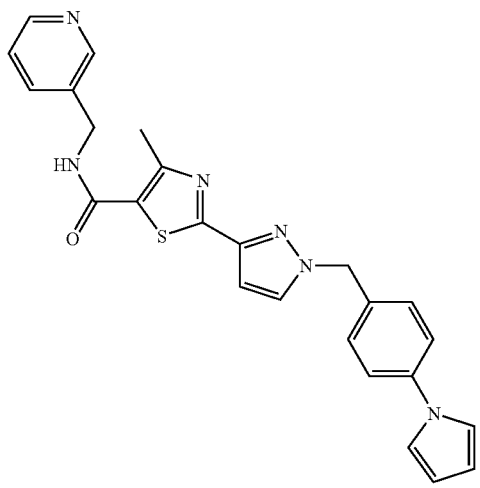

The title compound was prepared from 4-methyl-2-(2H-pyrazol-3-yl)-thiazole-5-carboxylic acid (pyridin-3-ylmethyl)-amide and 1-(4-bromomethyl-phenyl)-1H-pyrrole as described in Example 49 and isolated as a white solid (0.08 g, 52% yield). $^1$H NMR (400 MHz, CDCl$_3$) δ 8.60 (s, 1H), 8.54-8.57 (m, 1H), 7.71 (d, J=8.1 Hz, 1H), 7.26-7.43 (m, 6H), 7.07 (d, J=8 Hz, 2H), 6.86 (s, 1H), 6.35 (d, J=4 Hz, 2H), 6.18-6.25 (m, 1H), 5.36 (s, 2H), J=8 Hz, 2H), 2.75 (s, 3H); MS (M+H)$^+$=455.2; R$_f$=1.38 min; HRMS (M+H)$^+$=455.17.

Example 55

Synthesis of 4-methyl-2-[1-(4-[1,2,4]triazol-1-yl-benzyl)-1H-pyrazol-3-yl]-thiazole-5-carboxylic acid (pyridin-3-ylmethyl)amide

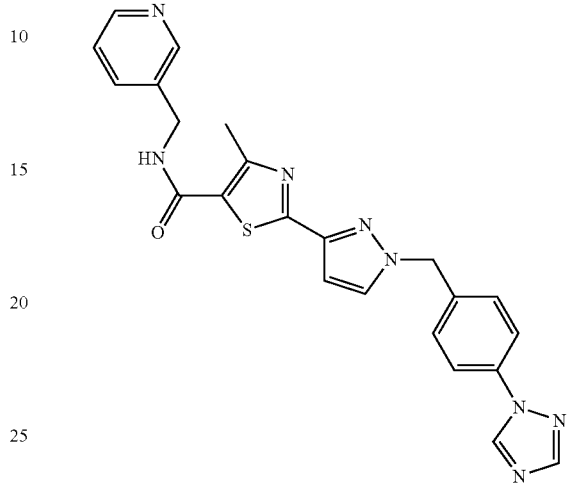

The title compound was prepared from 4-methyl-2-(2H-pyrazol-3-yl)-thiazole-5-carboxylic acid (pyridin-3-ylmethyl)-amide and 1-(4-bromomethyl-phenyl)-1H-[1,2,4]-triazole as described in Example 49 and isolated as a white solid (76 mg, 51% yield). $^1$H NMR (400 MHz, CDCl$_3$) δ 8.62 (s, 1H), 8.53-8.57 (m, 1H), 8.54 (s, 1H), 8.10 (s, 1H), 7.66-7.71 (m, 3H), 7.45 (bs, 1H), 7.39 (d, J=8 Hz, 1H), 7.37-7.41 (m, 1H), 6.88 (s, 1H), 6.05-6.12 (m, 1H), 5.41 (s, 2H), 4.63 (d, J=4 Hz, 2H), 2.75 (s, 3H); MS (M+H)$^+$=457.2; R$_f$=1.08 min; HRMS (M+H)$^+$=457.16.

Example 56

Synthesis of 4-methyl-2-[1-(4-pyrazol-1-yl-benzyl)-1H-pyrazol-3-yl]-thiazole-5-carboxylic acid (pyridin-3-ylmethyl)amide

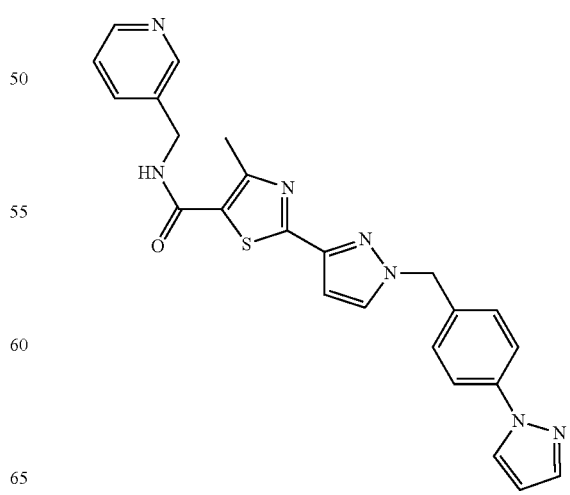

The title compound was prepared from 4-methyl-2-(2H-pyrazol-3-yl)-thiazole-5-carboxylic acid (pyridin-3-ylm-ethyl)-amide and 1-(4-bromomethyl-phenyl)-1H-pyrazole as described in Example 49 and isolated as white solid (0.075 g, 50% yield). ¹H NMR (400 MHz, CDCl₃) δ 8.61 (s, 1H), 8.55-8.58 (m, 1H), 7.91 (d, J=4 Hz, 1H) 7.65-7.73 (m, 4H), 7.29-7.31 (m, 1H), 7.34 (d, J=8 Hz, 2H), 7.40 (d, J=4 Hz, 1H), 6.86 (d, J=2 Hz, 1H), 6.47 (d, J=2 Hz, 1H), 6.09-6.14 (m, 1H), 5.37 (s, 2H), 4.63 (d, J=8 Hz, 2H), 2.75 (s, 3H); MS (M+H)⁺= 456.2; R_t=1.19 min; HRMS (M+H)⁺=456.16.

Example 57

Synthesis of 2-[1-(3-cyano-benzyl)-1H-pyrazol-3-yl]-4-methyl-thiazole-5-carboxylic acid (pyridin-3-ylmethyl)amide

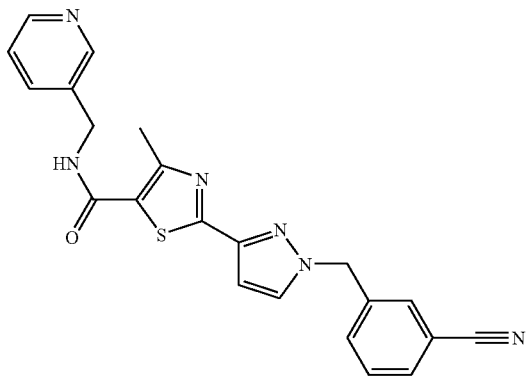

The title compound was prepared from 4-methyl-2-(2H-pyrazol-3-yl)-thiazole-5-carboxylic acid (pyridin-3-ylm-ethyl)-amide and 3-bromomethyl-benzonitrile as described in Example 49 and isolated as white solid (0.054 g, 40% yield). ¹H NMR (400 MHz, CDCl₃) δ 8.61 (s, 1H), 8.54-8.56 (m, 1H), 7.71 (d, J=8 Hz, 1H), 7.60-7.63 (m, 1H), 7.46-7.51 (m, 3H), 7.28-7.31 (m, 2H), 6.89 (s, 1H), 6.17-6.21 (m, 1H), 5.38 (s, 2H), 4.63 (d, J=8 Hz, 2H), 2.75 (s, 3H); MS (M+H)⁺= 415.2; R_t=1.16 min; HRMS (M+H)⁺=415.13.

Example 58

Synthesis of 2-[1-(4-fluoro-benzyl)-1H-pyrazol-3-yl]-4-methyl-thiazole-5-carboxylic acid (pyridin-3-ylmethyl)amide

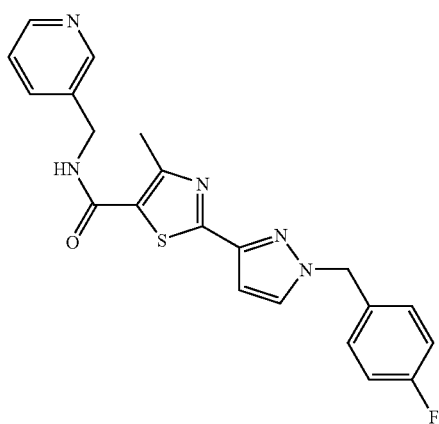

The title compound was prepared from 4-methyl-2-(2H-pyrazol-3-yl)-thiazole-5-carboxylic acid (pyridin-3-ylm-ethyl)-amide and 1-bromomethyl-4-fluoro-benzene as described in Example 49 and isolated as a white solid (0.072 g, 51% yield). ¹H NMR (400 MHz, CDCl₃) δ 8.61 (s, 1H), 8.54-8.57 (m, 2H), 7.71 (d, J=8 Hz, 1H), 7.38 (d, J=4 Hz, 1H), 7.21-7.32 (m, 3H), 7.02-7.06 (m, 2H), 6.84 (d, J=2 Hz, 1H), 6.12-6.15 (m, 1H), 5.31 (s, 2H), 4.63 (d, J=8 Hz, 2H), 2.75 (s, 3H); MS (M+H)⁺=408.3; R_t=1.22 min; HRMS (M+H)⁺= 408.13.

Example 59

Synthesis of 4-methyl-2-[1-(4-trifluoromethyl-ben-zyl)-1H-pyrazol-3-yl]-thiazole-5-carboxylic acid (pyridin-3-ylmethyl)amide

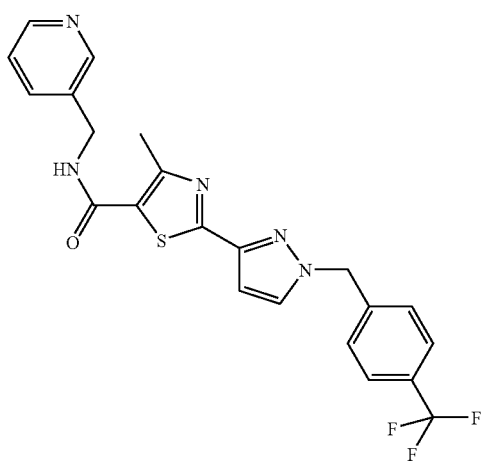

The title compound was prepared from 4-methyl-2-(2H-pyrazol-3-yl)-thiazole-5-carboxylic acid (pyridin-3-ylm-ethyl)-amide and bromomethyl-4-trifluoromethyl-benzene as described in Example 49 and isolated as yellow solid (0.075 g, 50% yield). ¹H NMR (400 MHz, CDCl₃) δ 8.61 (s, 1H), 8.56 (d, J=4 Hz, 2H), 7.70 (d, J=4 Hz, 1H), 7.61 (d, J=8 Hz, 2H), 7.44 (d, J=4 Hz, 1H), 7.26-7.36 (m, 3H), 6.88 (d, J=2 Hz, 1H), 6.13 (t, J=5 Hz, 1H), 5.41 (s, 2H), 4.63 (d, J=8 Hz, 2H), 2.75 (s, 3H); MS (M+H)⁺=458.1; R_t=1.35 min; HRMS (M+H)⁺=458.13.

Example 60

Synthesis of 4-methyl-2-[1-(3-trifluoromethyl-benzyl)-1H-pyrazol-3-yl]-thiazole-5-carboxylic acid (pyridin-3-ylmethyl)amide

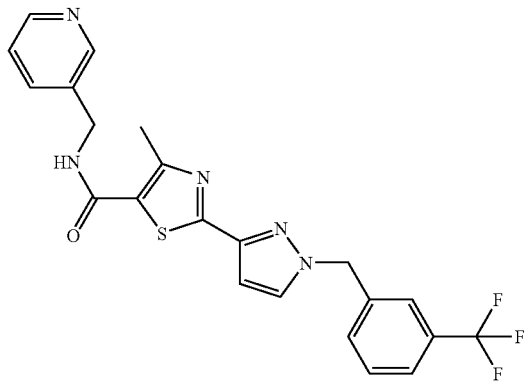

The title compound was made from 4-methyl-2-(2H-pyrazol-3-yl)-thiazole-5-carboxylic acid (pyridin-3-ylmethyl)-amide and bromomethyl-3-trifluoromethyl-benzene as described in Example 49 and isolated as a yellow solid (0:073 g, 48% yield). $^1$H NMR (400 MHz, CDCl$_3$) δ 8.61 (s, 1H), 8.56 (d, J=4 Hz, 1H), 7.71 (d, J=8 Hz, 1H), 7.59 (d, J=4 Hz, 2H), 7.41-7.53 (m, 4H), 7.28-7.33 (m, 3H), 6.88 (d, J=2 Hz, 1H), 6.06-6.12 (bm, 1H), 5.41 (s, 2H), 4.63 (d, J=4 Hz, 2H), 2.75 (s, 3H); MS (M+H)$^+$=457.9; R$_t$=1.35 min; HRMS (M+H)$^+$=458.12.

Example 61

Synthesis of 4-methyl-2-[1-(4-trifluoromethoxy-benzyl)-1H-pyrazol-3-yl]-thiazole-5-carboxylic acid (pyridin-3-ylmethyl)amide

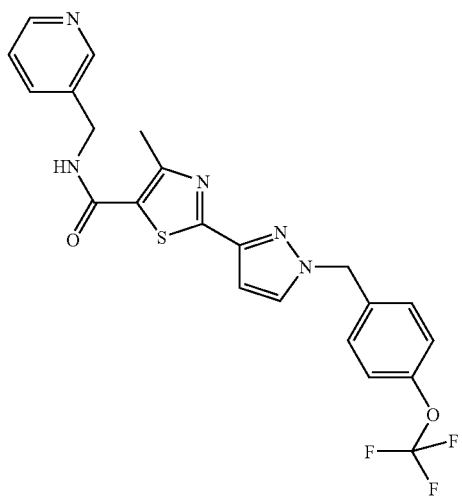

The title compound was prepared from 4-methyl-2-(2H-pyrazol-3-yl)-thiazole-5-carboxylic acid (pyridin-3-ylmethyl)-amide and bromomethyl-4-trifluoromethoxy-benzene as described in Example 49 and isolated as a yellow solid (0.078 g, 52% yield) $^1$H NMR (400 MHz, CDCl$_3$) δ 8.61 (s, 1H), 8.56 (d, J=4 Hz, 1H), 7.71 (d, J=8 Hz, 1H), 7.41 (d, J=2 Hz, 1H), 7.26-7:31 (m, 3H), 7.17-7.23 (m, 2H), 6.86 (d, J=2 Hz, 1H), 6.10-6.16 (m, 1H), 5.35 (s, 2H), 4.63 (d, J=8 Hz, 2H), 2.75 (s, 3H); MS (M+H)$^+$=474.1; R$_t$=1.38 min; HRMS (M+H)$^+$=474.12.

Example 62

Synthesis of 4-{3-[4-methyl-5-(2-pyridin-3-yl-acetyl)-2,5-dihydro-thiazol-2-yl]-pyrazol-1-ylmethyl}-benzoic acid ethyl ester

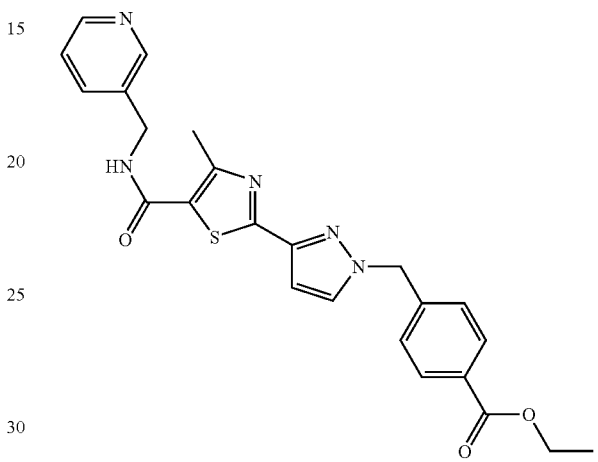

The title compound was prepared from 4-methyl-2-(2H-pyrazol-3-yl)-thiazole-5-carboxylic acid (pyridin-3-ylmethyl)-amide and 4-bromomethyl-benzoic acid ethyl ester as described in Example 49 and isolated as yellow oil (0.210 g, 70% yield). $^1$H NMR (400 MHz, CDCl$_3$) δ 8.61 (s, 1H), 8.56 (d, J=4 Hz, 1H), 8.02 (d, J=8 Hz, 2H), 7.71 (d, J=8 Hz, 1H), 7.42 (d, J=2 Hz, 1H), 7.26-7.31 (m, 3H), 6.87 (d, J=2 Hz, 1H), 6.10-6.16 (m, 1H), 5.40 (s, 2H), 4.63 (d, J=8 Hz, 2H), 4.37 (q, J=8 Hz, 2H), 2.75 (s, 3H), 1.38 (t, J=8 Hz, 3H); MS (M+H)$^+$=462.2; R$_t$=1.30 min; HRMS (M+H)$^+$=462.16.

Example 63

Synthesis of 2-[1-(4-tert-butyl-benzyl)-1H-pyrazol-3-yl]-4-methyl-thiazole-5-carboxylic acid (pyridin-3-ylmethyl)amide

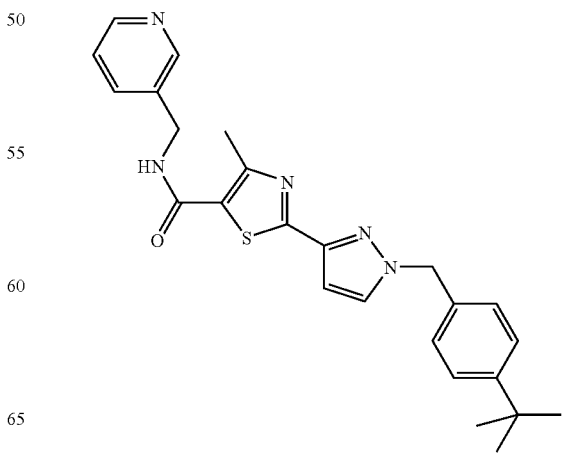

The title compound was prepared from 4-methyl-2-(2H-pyrazol-3-yl)-thiazole-5-carboxylic acid (pyridin-3-ylmethyl)-amide and 1-bromomethyl-4-tert-butyl-benzene as described in Example 49 and isolated as a yellow solid (0.080 g, 53% yield). $^1$H NMR (400 MHz, CDCl$_3$) δ 8.61 (s, 1H), 8.56 (d, J=4 Hz, 1H), 7.71 (d, J=8 Hz, 1H), 7.36-7.40 (m, 3H), 7.26-7.30 (m, 1H), 7.20 (d, J=8 Hz, 2H), 6.82 (d, J=2 Hz, 1H), 6.09-6.14 (m, 1H), 5.31 (s, 2H), 4.63 (d, J=8 Hz, 2H), 2.75 (s, 3H), 1.30 (s, 9H); MS (M+H)$^+$=445.9; R$_t$=1.47 min; HRMS (M+H)$^+$=446.20.

Example 64

Synthesis of 2-[1-(3,5-difluoro-benzyl)-1H-pyrazol-3-yl]-4-methyl-thiazole-5-carboxylic acid (pyridin-3-ylmethyl)amide

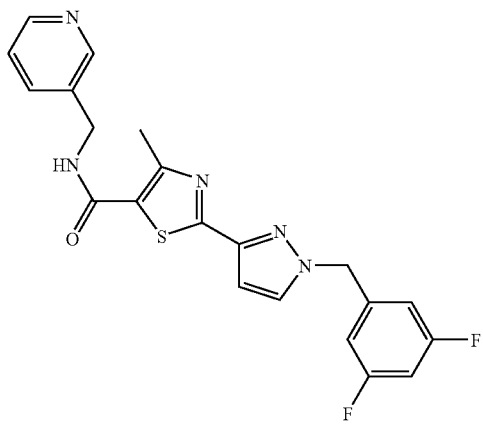

The title compound was prepared from 4-methyl-2-(2H-pyrazol-3-yl)-thiazole-5-carboxylic acid (pyridin-3-ylmethyl)-amide and 1-bromomethyl-3,5-difluoro-benzene as described in Example 49 and isolated as a white solid (0.071 mg, 51% yield). $^1$H NMR (400 MHz, CDCl$_3$) δ 8.61 (s, 1H), 8.56 (d, J=4 Hz, 1H), 7.71 (d, J=8 Hz, 1H), 7.45 (d, J=2 Hz, 1H), 7.28-7.34 (m, 1H), 6.89 (d, J=2 Hz, 1H), 6.70-6.79 (m, 3H), 6.12-6.18 (m, 1H), 5.32 (s, 2H), 4.63 (d, J=8 Hz, 2H), 2.75 (s, 3H); MS (M+H)$^+$=425.9; R$_t$=1.25 min; HRMS (M+H)$^+$=426.12.

Example 65

Synthesis of 2-[1-(3-fluoro-benzyl)-1H-pyrazol-3-yl]-4-methyl-thiazole-5-carboxylic acid (pyridin-3-ylmethyl)amide

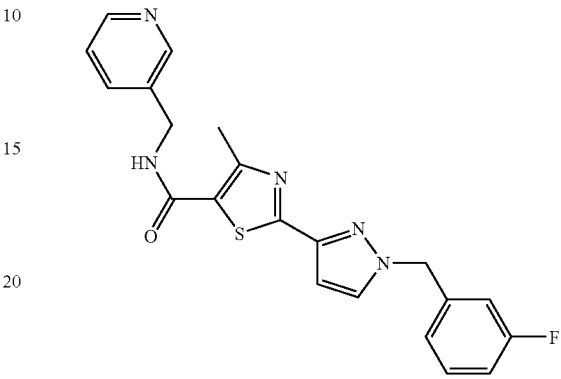

The title compound was prepared from 4-methyl-2-(2H-pyrazol-3-yl)-thiazole-5-carboxylic acid (pyridin-3-ylmethyl)-amide and 1-bromomethyl-3-fluoro-benzene as described in Example 49 and isolated as white solid (0.068 mg, 49% yield). $^1$H NMR (400 MHz, CDCl$_3$) δ 8.61 (s, 1H), 8.56 (d, J=4 Hz, 1H), 7.71 (d, J=8 Hz, 1H), 7.42 (d, J=2 Hz, 1H), 7.26-7.35 (m, 2H), 6.99-7.06 (m, 2H), 6.93 (d, J=8 Hz, 1H), 6.86 (d, J=2 Hz, 1H), 6.05-6.13 (m, 1H), 5.35 (s, 2H), 4.63 (d, J=8 Hz, 2H), 2.75 (s, 3H); MS (M+H)$^+$=408.2; R$_t$=1.25 min; HRMS (M+H)$^+$=408.13.

Example 66

Synthesis of 2-[1-(4-methanesulfonyl-benzyl)-1H-pyrazol-3-yl]-4-methyl-thiazole-5-carboxylic acid (pyridin-3-ylmethyl)amide

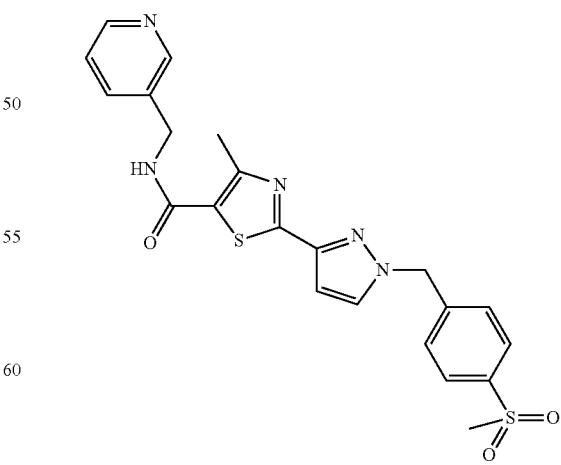

The title compound was prepared from 4-methyl-2-(2H-pyrazol-3-yl)-thiazole-5-carboxylic acid (pyridin-3-ylmethyl)-amide and 1-bromomethyl-4-methanesulfonyl-benzene as described in Example 49 and isolated as a white solid (0.058 mg, 45% yield). ¹HNMR (400 MHz, CDCl₃) δ 8.61 (s, 1H), 8.57 (d, J=4 Hz, 1H), 7.91 (d, J=8 Hz, 2H), 7.70 (d, J=8 Hz, 1H), 7.48 (d, J=2 Hz, 1H), 7.40 (d, J=8 Hz, 2H), 7.26-7.32 (m, 1H), 6.89 (d, J=4 Hz, 1H), 6.03-6.12 (m, 1H), 5.44 (s, 2H), 4.63 (d, J=4 Hz, 2H), 3.03 (s, 3H), 2.75 (s, 3H); MS (M+H)⁺=468.1; R_t=0.99 min; HRMS (M+H)⁺=468.12.

Example 67

Synthesis of 2-{1-[2-(4-methoxy-phenyl)-ethyl]-1H-pyrazol-3-yl}-4-methyl-thiazole-5-carboxylic acid (pyridin-3-ylmethyl)amide

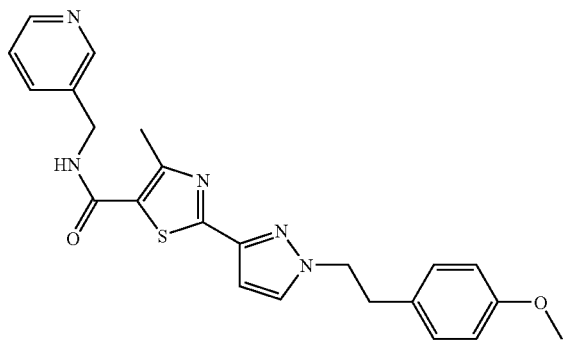

The title compound was prepared from 4-methyl-2-(2H-pyrazol-3-yl)-thiazole-5-carboxylic acid (pyridin-3-ylmethyl)-amide and 1-(2-bromo-ethyl)-4-methoxy-benzene as described in Example 49 and isolated as a white solid (0.030 mg, 21% yield). ¹H NMR (400 MHz, CDCl₃) δ 8.55-8.63 (bm, 2H), 7.72 (d, J=8 Hz, 1H), 7.28-7.33 (m, 1H), 7.15 (d, J=2 Hz, 1H), 6.97 (d, J=8 Hz, 2H), 6.80 (d, J=8 Hz, 2H), 6.72 (d, J=2 Hz, 1H), 6.12-6.19 (m, 1H), 4.64 (d, J=8 Hz, 2H), 4.33 (t, J=8 Hz, 2H), 3.77 (s, 3H), 3.12 (t, J=8 Hz, 3H), 2.76 (s, 3H); MS (M+H)⁺=433.9; R_t=1.25 min; HRMS (M+H)⁺=434.16.

Example 68

Synthesis of 4-methyl-2-[1-(2-methyl-2-phenyl-propyl)-1H-pyrazol-3-yl]-thiazole-5-carboxylic acid (pyridin-3-ylmethyl)amide

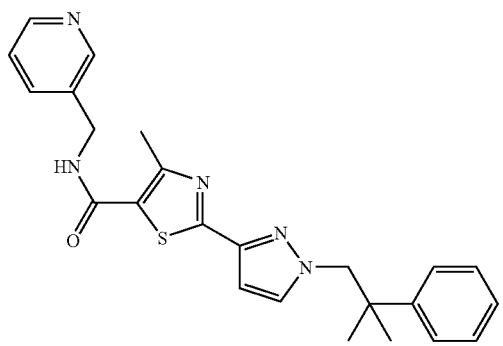

The title compound was prepared from 4-methyl-2-(2H-pyrazol-3-yl)-thiazole-5-carboxylic acid (pyridin-3-ylmethyl)-amide and (2-chloro-1,1-dimethyl-ethyl)benzene as described in Example 49 and isolated as a white solid, (0.025 mg, 20% yield). ¹H NMR (400 MHz, CDCl₃) δ 8.65 (bs, 1H), 8.57 (d, J=4 Hz, 1H), 7.78 (d, J=8 Hz, 1H), 7.23-7.49 (m, 6H) 6.69 (d, J=2 Hz, 1H), 6.63 (d, J=2 Hz, 1H), 6.12-6.18 (bm, 1H), 4.64 (d, J=4 Hz, 2H), 4.28 (s, 2H), 2.75 (s; 3H), 1.40 (s, 6H); MS (M+H)⁺=432.2; R_t=1.39 min; HRMS (M+H)⁺= 432.19.

Example 69

Synthesis of 4-methyl-2-[1-(2-phenyl-propyl)-1H-pyrazol-3-yl]-thiazole-5-carboxylic acid (pyridin-3-ylmethyl)amide

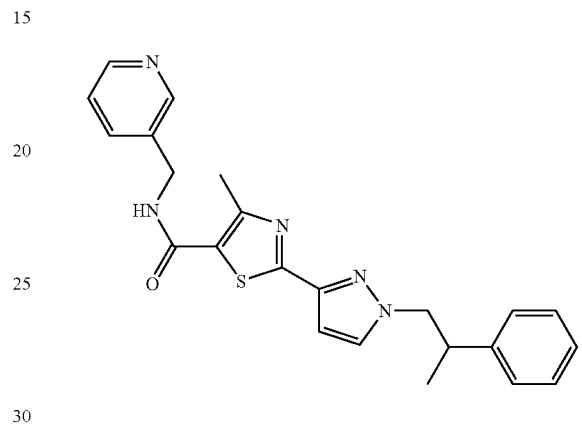

The title compound was prepared from 4-methyl-2-(2H-pyrazol-3-yl)-thiazole-5-carboxylic acid (pyridin-3-ylmethyl)-amide and (2-bromo-1-methyl-ethyl)benzene as described in Example 49 and isolated as a white solid (0.120 mg, 45% yield). ¹H NMR (400 MHz, CDCl₃) δ 8.60 (s, 1H), 8.55 (d, J=4 Hz, 1H), 7.71 (d, J=8 Hz, 1H), 7.18-7.33 (m, 4H), 7.12 (d, J=8 Hz, 2H), 7.03 (d, J=2 Hz, 1H), 6.67 (d, J=2 Hz, 1H), 6.16-6.24 (m, 1H), 4.63 (d, J=4 Hz, 2H), 4.18-4.31 (m, 2H), 3.34-3.44 (m, 1H), 2.74 (s, 3H), 1.29 (d, J=4 Hz, 3H); MS (M+H)⁺=418.2; R_t=1.31 min; HRMS (M+H)⁺=418.17.

Example 70

Synthesis of 4-methyl-2-[(1-((R)-2-phenyl-propyl)-1H-pyrazol-3-yl]-thiazole-5-carboxylic acid (pyridin-3-ylmethyl)amide

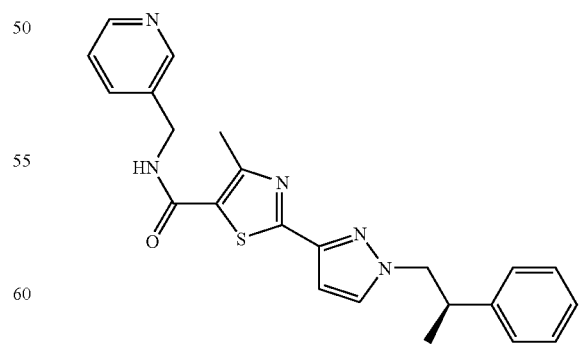

The title compound was made from 4-methyl-2-(2H-pyrazol-3-yl)-thiazole-5-carboxylic acid (pyridin-3-ylmethyl)-amide and (2-bromo-1-methyl-ethyl)benzene as described in Example 49 and isolated by chiral separation (80/20 heptane/ ethanol) (0.0033 mg, 15% yield). ¹H NMR (400 MHz, CDCl₃) δ 8.61 (s, 1H), 8.56 (d, J=4 Hz, 1H), 7.72 (d, J=8 Hz, 1H), 7.19-7.32 (m, 4H), 7.13 (d, J=8 Hz, 2H); 7.04 (d, J=2 Hz, 1H), 6.67 (d, J=2 Hz, 1H), 6.12-6.19 (m, 1H), 4.63 (d, J=4 Hz, 2H), 4.17-4.32 (m, 2H), 3.35-3.45 (m, 1H), 2.75 (s, 3H), 1.30 (d, J=8 Hz, 3H); MS (M+H)⁺=418.3; R$_t$=1.32 min; HRMS (M+H)⁺=418.17.

Example 71

Synthesis of 4-methyl-2-[1-((S)-2-phenyl-propyl)-1H-pyrazol-3-yl]-thiazole-5-carboxylic acid (pyridin-3-ylmethyl)amide

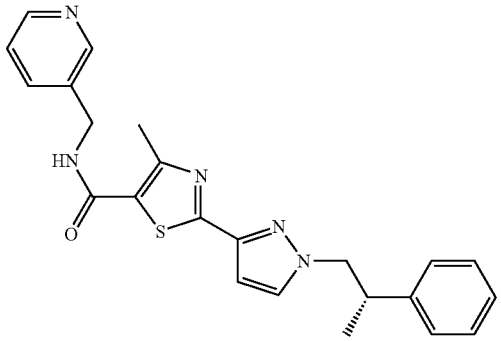

The title compound was prepared from 4-methyl-2-(2H-pyrazol-3-yl)-thiazole-5-carboxylic acid (pyridin-3-ylmethyl)-amide and (2-bromo-1-methyl-ethyl)benzene as described in Example 49 and isolated by chiral separation (80/20 heptane/ethanol) (0.0033 mg, 15% yield). ¹HNMR (400 MHz, CDCl₃) δ 8.61 (s, 1H), 8.56 (d, J=4 Hz, 1H), 7.71 (d, J=8 Hz, 1H), 7.18-7.34 (m, 4H), 7.13 (d, J=8 Hz, 2H), 7.04 (d, J=2 Hz, 1H), 6.67 (d, J=2 Hz, 1H), 6.12-6.20 (m, 1H), 4.63 (d, J=4 Hz, 2H), 4.18-4.38 (m, 2H), 3.37-3.46 (m, 1H), 2.75 (s, 3H), 1.30 (d, J=8 Hz, 3H); MS (M+H)⁺=418.4; R$_t$=1.31 min; HRMS (M+H)⁺=418.17.

Example 72

Synthesis of 2-{1-[(2-phenoxy)-ethyl]-1H-pyrazol-3-yl}-4-methyl-thiazole-5-carboxylic acid (pyridin-3-ylmethyl)amide

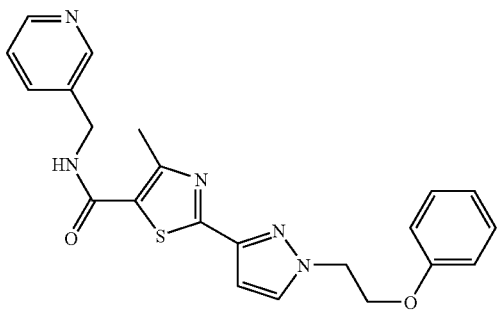

The title compound was made from 4-methyl-2-(2H-pyrazol-3-yl)-thiazole-5-carboxylic acid (pyridin-3-ylmethyl)-amide and (2-bromo-ethoxy)-benzene as described in Example 49 and isolated as a white solid (0.0032 mg, 15% yield). ¹H NMR (400 MHz, CDCl₃) δ 8.58 (d, J=2 Hz, 1H), 8.54 (d, J=4 Hz, 1H), 7.70 (d, J=4 Hz, 1H), 7.59 (d, J=2 Hz, 1H), 7.22-7.30 (m, 3H), 6.93-6.99 (m, 1H), 6.86 (d, J=8 Hz, 2H), 6.80 J=2 Hz, 1H), 6.23-6.30 (m, 1H), 4.61 (d, J=4 Hz, 2H), 4.54 (t, J=5 Hz, 2H), 4.35 (t, J=5 Hz, 2H), 2.73 (s, 3H); MS (M+H)⁺=420.2; R$_t$=1.35 min; HRMS (M+H)⁺=420.15.

Example 73

Synthesis of 2-{1-[2-(4-fluoro-phenoxy)-ethyl]-1H-pyrazol-3-yl}-4-methyl-thiazole-5-carboxylic acid (pyridin-3-ylmethyl)amide

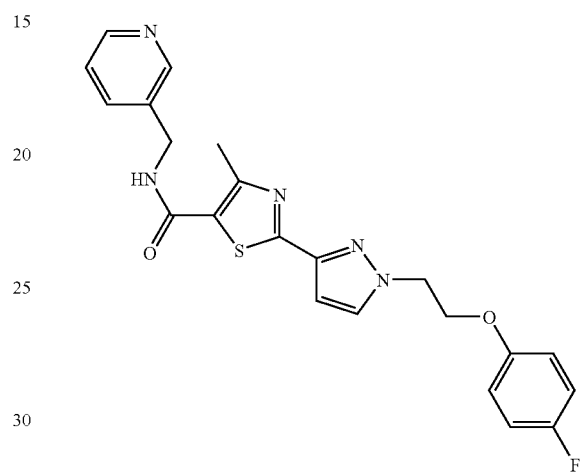

The title compound was made from 4-methyl-2-(2H-pyrazol-3-yl)-thiazole-5-carboxylic acid (pyridin-3-ylmethyl)-amide and 1-(2-bromo-ethoxy)-4-fluoro-benzene as described in Example 49 and isolated as a white solid (0.0032 mg, 15% yield). ¹H NMR (400 MHz, CDCl₃) δ 8.60 (d, J=2 Hz, 1H), 8.55 (d, J=4 Hz, 1H), 7.71 (d, J=4 Hz, 1H), 7.58 (d, J=2 Hz, 1H), 7.26-7.32 (m, 1H), 6.90-6.98 (m, 2H), 6.76-6.84 (m, 3H), 6.10-6.17 (m, 1H), 4.63 (d, J=8 Hz, 2H), 4.53 (t, J=5 Hz, 2H), 4.32 (t, J=5 Hz, 2H), 2.74 (s, 3H); MS (M+H)⁺= 438.0; R$_t$=1.27 min; HRMS (M+H)⁺=438.14.

Example 74

Synthesis of 4-methyl-2-{1-[2-(4-trifluoromethoxy-phenyl)-ethyl]-1H-pyrazol-3-yl}-thiazole-5-carboxylic acid (pyridin-3-ylmethyl)amide

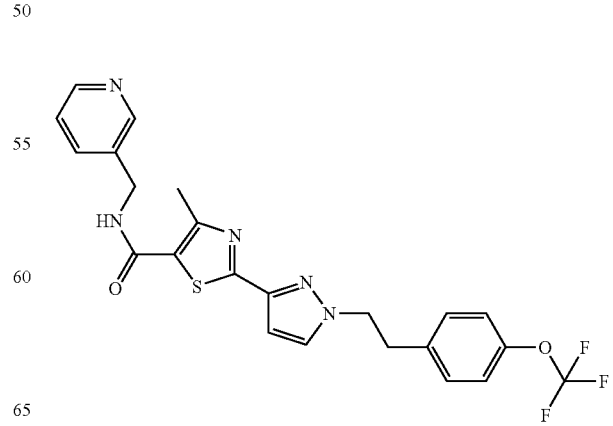

The title compound was made from 4-methyl-2-(2H-pyrazol-3-yl)-thiazole-5-carboxylic acid (pyridin-3-ylmethyl)-amide and 1-(2-bromo-ethyl)-4-trifluoromethoxy-benzene as described in Example 49 and isolated as a white solid (0.0032 mg, 15% yield). $^1$H NMR (400 MHz, CDCl$_3$) δ 8.61 (bs, 1H), 8.56 (d, J=4 Hz, 1H), 7.71 (d, J=8 Hz, 1H), 7.26-7.33 (m, 1H), 7.17 (d, J=2 Hz, 1H), 7.05-7.13 (m, 4H), 6.74 (d, J=2 Hz, 1H), 6.07-6.13 (m, 1H), 4.64 (d, J=4 Hz, 2H), 4.37 (t, J=8 Hz, 2H), 3.21 (t, J=8 Hz, 2H), 2.76 (s, 3H); MS (M+H)$^+$=488.2; R$_t$=1.45 min; HRMS (M+H)$^+$=488.14.

Example 75

Synthesis of 2-[1-(2-hydroxy-ethyl)-1H-pyrazol-3-yl]-4-methyl-thiazole-5-carboxylic acid (pyridin-3-ylmethyl)amide

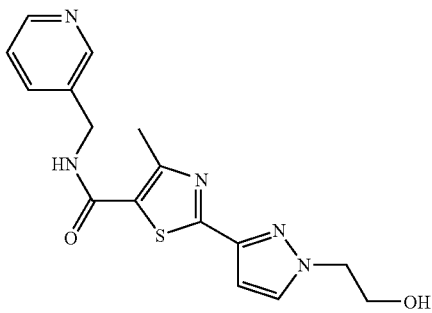

The title compound was prepared from 4-methyl-2-(2H-pyrazol-3-yl)-thiazole-5-carboxylic acid (pyridin-3-ylmethyl)-amide and 2-iodo-ethanol as described in Example 49 and isolated as a yellow oil (0.11 g, 55% yield). $^1$H NMR (400 MHz, CDCl$_3$) δ 8.59 (s, 1H), 8.54 (d, J=3 Hz, 1H), 7.71 (d, J=4 Hz, 1H), 7.50 (d, J=2 Hz, 1H), 7.27-7.31 (m, 1H), 6.82 (d, J=2 Hz, 1H), 6.24-6.28 (bm, 1H), 4.62 (d, J=8 Hz, 2H), 4.29 (t, J=4 Hz, 2H), 4.04 (t, J=4 Hz, 2H), 2.89-2.95 (bm, 1H), 2.74 (s, 3H); MS (M+H)$^+$=344.1; R$_t$=0.85 min; HRMS (M+H)$^+$=344.12.

Example 76

Synthesis of methanesulfonic acid 2-(3-{4-methyl-5-[(pyridin-3-ylmethyl)-carbamoyl]-thiazol-2-yl}-pyrazol-1-yl)ethyl ester

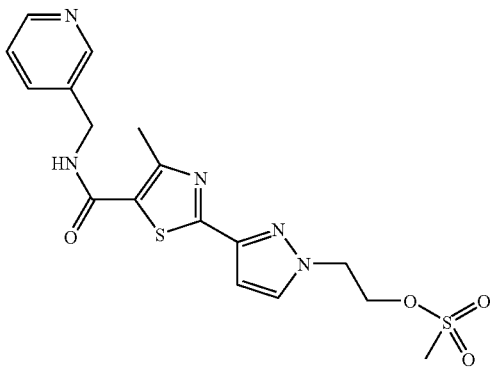

To a solution of -[1-(2-hydroxy-ethyl)-1H-pyrazol-3-yl]-4-thiazole-5-carboxylic acid (pyridin-3-ylmethyl)-amide (0.16 g, 0.46 mmol) in pyridine (2 mL), under nitrogen at 0° C. was added methanesulfonyl chloride (0.04 mL, 0.51 mmol). The reaction mixture was stirred at room temperature for 3 hr. The reaction mixture was diluted with methylene chloride (50 mL), washed with NaHCO$_3$ (100 mL), water (100 mL) and brine (100 mL). The organic phase was dried (Na$_2$SO$_4$) and evaporated. This material, methanesulfonic acid 2-(3-{4-methyl-5-[(pyridin-3-ylmethyl)-carbamoyl]-thiazol-2-yl}-yrazol-1-yl)-ethyl ester, was used without further purification as a yellow oil (0.15 g, 79%). MS (M+H)$^+$=422.

Example 77

Synthesis of 4-methyl-2-[1-(2-phenylamino-ethyl)-1H-pyrazol-3-yl]-thiazole-5-carboxylic acid (pyridin-3-ylmethyl)amide

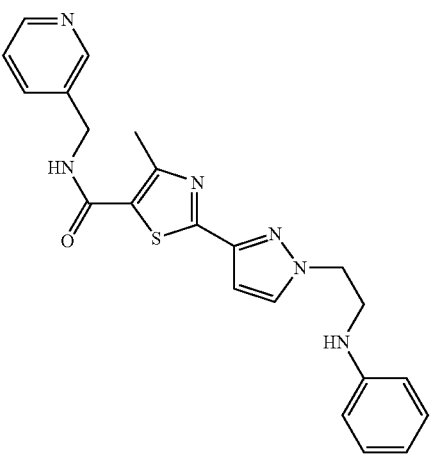

To a solution of methanesulfonic acid 2-(3-{4-methyl-5-[(pyridin-3-ylmethyl)-carbamoyl]-thiazol-2-yl}-pyrazol-1-yl)-ethyl ester (0.19 g, 0.45 mmol) in methylene chloride (2 mL) was added aniline (0.91 mL, 9.93 mmol). The reaction mixture was heated under nitrogen at 85° C. for 16 hr. The reaction mixture was diluted with ethyl acetate (50 mL), washed with NaHCO$_3$ (100 mL), water (100 mL) and brine (100 mL). The organic phase was dried (Na$_2$SO$_4$) and evaporated. The residue was purified by preparative thin layer chromatography over silica gel (methylene chloride:methanol, 95:5) to provide 4-methyl-2-[1-(2-phenylamino-ethyl)-1H-pyrazol-3-yl]-4-methyl-thiazole-5-carboxylic acid (pyridin-3-ylmethyl)-amide as a white solid (0.052 g, 52%). $^1$H NMR (400 MHz, CDCl$_3$) δ 8.66 (s, 1H), 8.58 (d, J=4 Hz, 1H), 7.78 (d, J=8 Hz, 1H), 7.41 (d, J=2 Hz, 1H), 7.32-7.37 (m, 1H), 7.17-7.23 (m, 2H), 6.83 (d, J=2 Hz, 1H), 6.76 (t, J=8 Hz, 1H), 6.63 (d, J=5 Hz, 2H), 6.18-6.23 (m, 1H), 4.67 (d, J=8 Hz, 2H), 4.38 (t, J=4 Hz, 2H), 3.68 (t, J=4 Hz, 2H), 2.77 (s, 3H); MS (M+H)$^+$=419.2; R$_t$=1.23 min; HRMS (M+H)$^+$=419.17.

Example 78

Synthesis of 2-{1-[2-(4-fluoro-phenyl)amino-ethyl]-1H-pyrazol-3-yl}-4-methyl-thiazole-5-carboxylic acid (pyridin-3-ylmethyl)amide

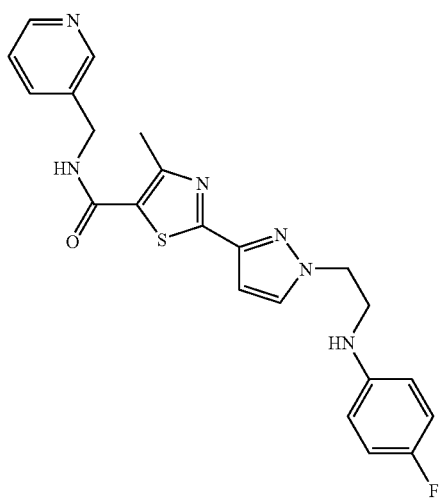

The title compound was prepared from methanesulfonic acid 2-(3-{4-methyl-5-[(pyridin-3-ylmethyl)-carbamoyl]-thiazol-2-yl}-pyrazol-1-yl)-ethyl ester and 4-fluoro-phenylamine as describe in Example 77 and isolated as a white solid (0.032 g, 53% yield). $^1$H NMR (400 MHz, CDCl$_3$) δ 8.63 (s, 1H), 8.56 (d, J=4 Hz, 1H), 7.72 (d, J=8 Hz, 1H), 7.39 (d, J=2 Hz, 1H), 7.28-7.34 (m, 1H), 6.89 (t, J=8 Hz, 2H), 6.83 (d, J=2 Hz, 1H), 6.51-6.56 (m, 2H), 6.09 (bs, 1H), 4.65 (d, J=8 Hz, 2H), 4.47 (t, J=6 Hz, 2), 3.58-3.63 (m, 2H), 2.76 (s, 3H); MS (M+H)$^+$=436.9; R$_t$=1.20 min; HRMS (M+H)$^+$=437.12.

Example 79

Synthesis of 4-methyl-2-{1-[2-(methyl-phenylamino)-ethyl]-1H-pyrazol-3-yl}-thiazole-5-carboxylic acid (pyridin-3-ylmethyl)amide

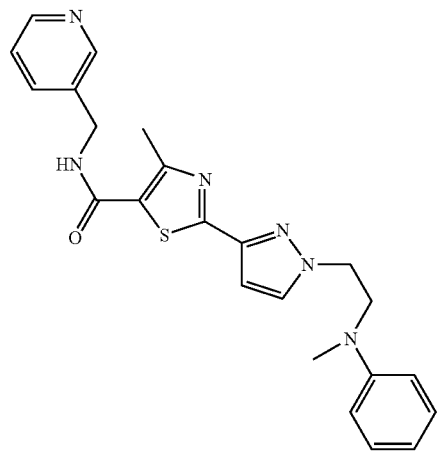

The title compound was prepared from methanesulfonic acid 2-(3-{4-methyl-5-[(pyridin-3-ylmethyl)-carbamoyl]-thiazol-2-yl}-pyrazol-1-yl)-ethyl ester and methyl-phenyl amine as describe in Example 77 and isolated as a white solid (0.043 g, 54% yield). $^1$H NMR (400 MHz, CDCl$_3$) δ 8.63 (bs, 1H), 8.57 (d, J=4 Hz, 1H), 7.73 (d, J=8 Hz, 1H), 7.28-7.34 (m, 1H), 7.29 (d, J=2 Hz, 1H), 7.21-7.26 (m, 2H), 6.77 (d, J=2 Hz, 1H), 6.73 (t, J=8 Hz, 1H), 6.65 (d, J=8 Hz, 2H), 6.06-6.13 (bm, 2H), 4.64 (d, J=4 Hz, 2H), 4.34 (t, J=5 Hz, 2H), 3.83 (t, J=5 Hz, 2H), 2.76 (s, 3H), 2.74 (s, 3H); MS (M+H)$^+$=432.9; R$_t$=1.28 min; HRMS (M+H)$^+$=433.17.

Example 80

Synthesis of 2-[1-(2-(tert-butoxycarbonylamino)ethyl)-1H-pyrazol-3-yl]-4-methylthiazole-5-carboxylic acid (pyridin-3-ylmethyl)amide

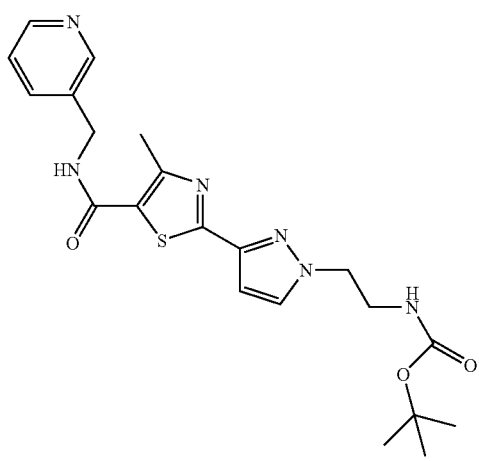

To a solution of 4-methyl-2-(2H-pyrazol-3-yl)-thiazole-5-carboxylic acid (pyridin-3-ylmethyl)-amide (0.5 g, 1.67 mmol) in acetonitrile (10 mL) was added 2-(boc-amino)ethyl bromide (0.37 g, 1.67 mmol) and Cs$_2$CO$_3$ (1.08 g, 3.34 mmol). The reaction mixture was heated under nitrogen at 85° C. for 16 hr. The reaction mixture was diluted with ethyl acetate (100 mL), water (200 mL) and brine (200 mL). The organic phase was dried (Na$_2$SO$_4$) and evaporated. The residue was purified by preparative thin layer chromatography over silica gel (methylene chloride:methanol, 95:5) to provide 2-{1-[2-(2-boc-amino-ethyl)-1H-pyrazol-3-yl]-4-methyl-thiazole-5-carboxylic acid (pyridin-3-ylmethyl) as a tan solid (0.35 g, 47%). $^1$H NMR (400 MHz, CDCl$_3$) δ 8.62 (bs, 1H), 8.56 (d, J=4 Hz, 1H), 7.72 (d, J=8 Hz, 1H), 7.43 (d, J=2 Hz, 1H), 7.26-7.33 (m, 1H), 6.81 (d, J=2 Hz, 1H), 6.09-6.13 (bm, 1H), 4.75 (bs, 1H), 4.64 (d, J=4 Hz, 2H), 4.28 (bt, J=5

Hz, 2H), 3.58-3.64 (m, 2H), 2.75 (s, 3H), 1.43 (s, 9H); MS (M+H)$^+$=443.2; R$_t$=1.17 min; HRMS (M+H)$^+$=443.19.

Example 81

Synthesis of 2-{1-[2-(4-fluoro-benzoylamino)-ethyl]-1H-pyrazol-3-yl}-4-methyl-thiazole-5-carboxylic acid (pyridin-3-ylmethyl)amide

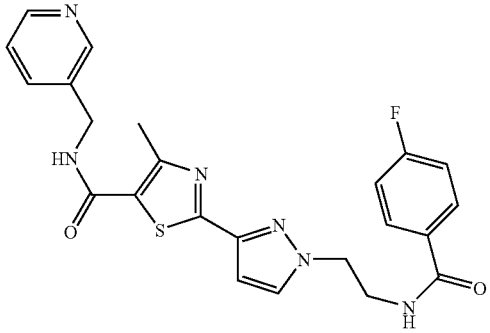

Part A. Synthesis of 2-[1-(2-amino-ethyl)-1H-pyrazol-3-yl]-4-methyl-thiazole-5-carboxylic acid (pyridin-3-ylmethyl)-amide)

To a solution of 2-{1-[2-(2-boc-amino-ethyl)-1H-pyrazol-3-yl]-4 methyl-thiazole-5-carboxylic acid (pyridin-3-ylmethyl)-amide (0.48 g, 1.08 mmol) in methylene chloride (5 mL) was added trifluoroacetic acid (1 mL). The reaction mixture was stirred under nitrogen at room temperature for 2 hr. The reaction mixture was diluted with methylene chloride (100 mL), water (200 mL) and brine (200 mL). The organic phase was dried. (Na$_2$SO$_4$) and evaporated. This material, 2-[1-(2-amino-ethyl)-1H-pyrazol-3-yl]-4-methyl-thiazole-5-carboxylic acid (pyridin-3-ylmethyl)-amide), was used without further purification as a yellow solid (0.35 g, 95%).

Part B. Synthesis of 2-{1-[2-(4-fluoro-benzoylamino)-ethyl]-1H-pyrazol-3-yl}-4-methyl-thiazole-5-carboxylic acid (pyridin-3-ylmethyl)-amide To a solution of 2-[1-(2-amino-ethyl)-1H-pyrazol-3-yl]-4-methyl-thiazole-5-carboxylic acid (pyridin-3-ylmethyl)-amide (0.1 g, 0.29 mmol) in methylene chloride (5 mL) was added 4-fluoro-benzoyl chloride (0.07 mL, 0.44 mmol) and triethyl amine (0.08 mL, 0.58 mmol). The reaction mixture was stirred under nitrogen at room temperature for 16 hr. The reaction mixture was diluted with methylene chloride (50 mL), water (100 mL) and brine (100 mL). The organic phase was dried (Na$_2$SO$_4$) and evaporated. The residue was purified by preparative thin layer chromatography over silica gel (hexanes:ethyl acetate, 1:1) to provide 2-{1-[2-(4-fluoro-benzoylamino)-ethyl]-1H-pyrazol-3-yl}-4-methyl-thiazole-5-carboxylic acid (pyridin-3-ylmethyl)-amide as a white solid (0.56 g, 43%). $^1$H NMR (400 MHz, CDCl$_3$) δ 8.63 (bs, 1H), 8.57 (d, J=4 Hz, 1H), 7.70-7.81 (m, 3H), 7.46 (d, J=2 Hz, 1H), 7.29-7.33 (m, 1H), 7.09 (t, J=8 Hz, 2H), 6.84 (d, J=2 Hz, 1H), 6.84-6.88 (m, 1H), 6.10-6.15 (bm, 1H), 4.65 (d, J=4 Hz, 2H), 4.42 (bt, J=5 Hz, 2H), 3.89-3.97 (m, 2H), 2.75 (s, 3H); MS (M+H)$^+$=464.8; R$_t$=1.04 min; HRMS (M+H)$^+$=465.15.

Example 82

Synthesis of 2-{1-[2-(4-fluoro-benzenesulfonylamino)-ethyl]-1H-pyrazol-3-yl}-4-methyl-thiazole-5-carboxylic acid (pyridin-3-ylmethyl)amide

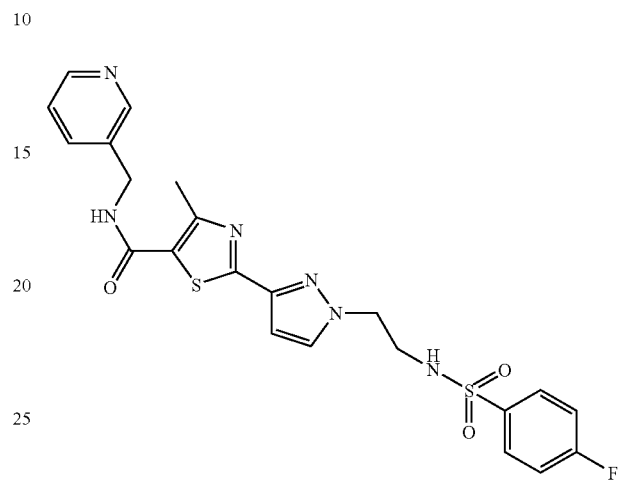

The title compound was prepared from 2-[1-(2-amino-ethyl)-1H-pyrazol-3-yl]-4-methyl-thiazole-5-carboxylic acid (pyridin-3-ylmethyl)-amide) and 4-fluoro-benzenesulfonyl chloride as describe in Example 81 and isolated as a white solid (0.052 g, 37% yield). $^1$H NMR (400 MHz, CDCl$_3$) δ 8.62 (s, 1H), 8.56 (d, J=4 Hz, 1H), 7.83-7.87 (m, 2H), 7.73 (d, J=8 Hz, 1H), 7.42 (d, J=2 Hz, 1H), 7.27-7.33 (m, 1H), 7.16 (t, J=8 Hz, 2H), 6.79 (d, J=2 Hz, 1H), 6.09-6.14 (bm, 1H), 5.36 (bs, 1H), 4.64 (d, J=8 Hz, 2H), 4.25-4.29 (m, 2H), 3.47 (bs, 2H), 2.74 (s, 3H); MS (M+H)$^+$=500.8; R$_t$=1.08 min; HRMS (M+H)$^+$=501.12.

Example 83

Synthesis of 4-methyl-2-[1-(2-phenoxy-ethyl)-1H-pyrazol-3-yl]-thiazole-5-carboxylic acid, 4-fluoro-benzylamide

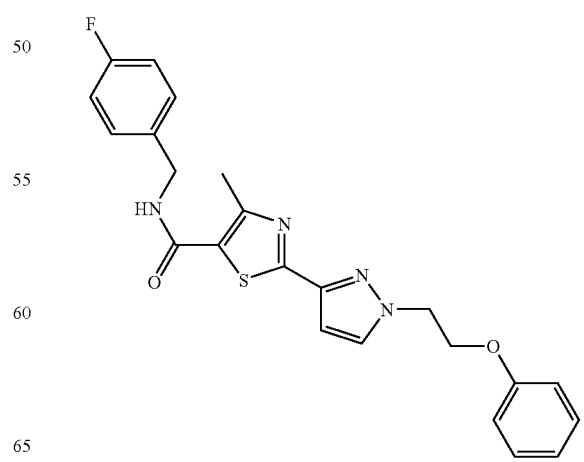

Part A. Synthesis of 2-bromo-4-methyl-thiazole-5-carboxylic acid 4-fluoro-benzylamide To a solution of 2-bromo-4-methyl-thiazole-5-carboxylic acid (10.0 g, 45.0 mmol) in methylene chloride (200 mL) was added 4-fluoro-benzylamine (6.19 g, 49.5 mmol), benzotriazol-1-yloxytris(dimethylamino)phosphonium hexafluorophosphate (21.9 g, 49.5 mmol) and N,N-diisopropylethylamine (15.7 mL, 90.1 mmol) and the mixture was stirred under nitrogen at room temperature for 16 hr. The reaction mixture was diluted with methylene chloride (300 mL), washed with water (300 mL) and brine (2×200 mL). The organic phase was dried ($Na_2SO_4$) and evaporated. The residue was purified by flash chromatography over silica gel (methylene chloride:methanol, 95:5) to provide 2-bromo-4-methyl-thiazole-5-carboxylic acid 4-fluoro-benzylamide as a beige solid (13.5 g, 90% yield). MS $(M+H)^+$=330; $R_t$=136 min.

Part B. Synthesis of 4-methyl-2-(2H-pyrazol-3-yl)-thiazole-5-carboxylic acid 4-fluoro-benzylamide To a solution of 2-bromo-4-methyl-thiazole-5-carboxylic acid 4-fluoro-benzylamide (5.0 g, 15.0 mmol) in toluene (30 mL), water (10 mL) and ethanol (10 mL) was added 1H-pyrazole-5-boronic acid (1.70 g, 15.0 mmol), $Pd(PPh_3)_4$ (1.75 g, 1.52 mmol), and potassium carbonate (6.3 g, 45.6 mmol). The resulting mixture was degassed three times and heated to 100° C. for 16 hr. The reaction mixture was cooled to room temperature, diluted with ethyl acetate (200 mL) and washed with brine (2×100 mL). The organic phase was dried ($Na_2SO_4$) and evaporated. The residue was purified by flash chromatography over silica gel (ethyl acetate:hexane, 50:50) to provide 4-methyl-2-(2H-pyrazol-3-yl)-thiazole-5-carboxylic acid 4-fluoro-benzylamide as yellow solid (3.25 g 68%) MS $(M+H)^+$=317; $R_t$=1.13 min; HRMS $(M+H)^+$=317.

Part C. Synthesis of 4-methyl-2-[1-(2-phenoxy-ethyl)-1H-pyrazol-3-yl]-thiazole-5-carboxylic acid 4-fluoro-benzylamide A solution of 4-methyl-2-(2H-pyrazol-3-yl)-thiazole-5-carboxylic acid 4 fluoro-benzylamide (0.1 g, 0.33 mmol) in dimethyl sulfoxide (5 mL) was treated with (2-bromo-ethoxy)benzene (0.11 g, 0.50 mmol) and potassium carbonate (0.14 g, 1.0 mmol), and the reaction mixture was heated to 90° C. for 16 hr. The reaction mixture was cooled to room temperature, diluted with ethyl acetate (50 mL), and washed with brine (2×50 mL). The organic phase was dried ($Na_2SO_4$) and evaporated. The residue was purified by preparative thin layer chromatography over silica gel (methylene chloride:methanol, 95:5) to provide 4-methyl-2-[1-(2-phenoxy-ethyl)-1H-pyrazol-3-yl]-thiazole-5-carboxylic acid 4-fluoro-benzylamide as a tan solid (0.061 g, 43% yield). $^1$H NMR (400 MHz, $CDCl_3$) δ 7.46 (s, 1H), 7.07-7.19 (m, 5H), 6.78-6.93 (m, 3H), 6.70-6.73 (m, 2H), 5.82-5.88 (bm, 1H), 4.38-4.44 (m, 4H), 4.20 (t, J=5 Hz, 2H), 2.60 (s, 3H); MS $(M+H)^+$=437.1; $R_t$=1.51 min; HRMS $(M+H)^+$=437.14.

Example 84

Synthesis of 4-methyl-2-[1-(2-methyl-2-phenyl-propyl)-1H-pyrazol-3-yl]-thiazole-5-carboxylic acid 4-fluoro-benzylamide

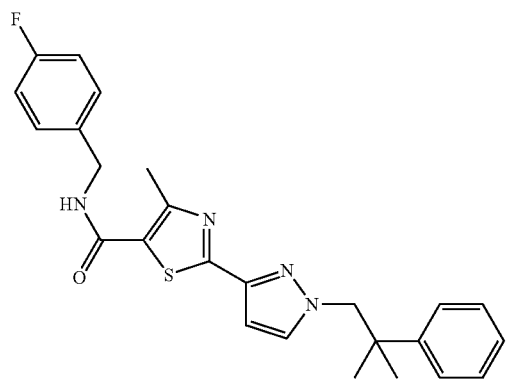

The title compound was prepared from 4-methyl-2-(2H-pyrazol-3-yl)thiazole-5-carboxylic acid 4-fluoro-benzylamide and (2-chloro-1,1-dimethyl-ethyl)-benzene as describe in Example 83 and isolated as a white solid (0.046 g, 33% yield). $^1$H NMR (400 MHz, $CDCl_3$) δ 7.22-7.35 (m, 7H), 7.02-7.08 (m, 1H), 6.69 (d, J=2 Hz, 1H), 6.62 (d, J=2 Hz, 1H), 5.96-6.03 (bm, 1H), 4.57 (d, J=4 Hz, 2H), 4.28 (s, 2H), 2.73 (s, 3H), 1.40 (s, 6H); MS $(M+H)^+$=449.2; $R_t$=1.64 min; HRMS $(M+H)^+$=449.18.

Example 85

Synthesis of 2-[1-(2-cyclopropyl-ethyl)-1H-pyrazol-3-yl]-4-methyl-thiazole-5-carboxylic acid 4-fluoro-benzylamide

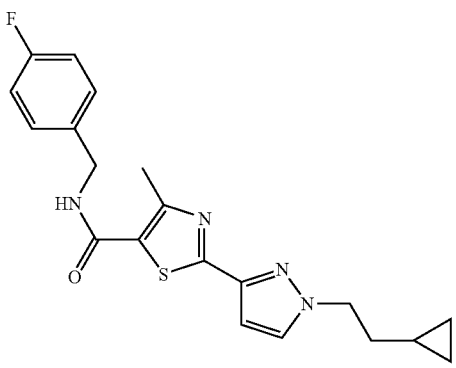

The title compound was prepared from 4-methyl-2-(2H-pyrazol-3-yl)thiazole-5-carboxylic acid 4-fluoro-benzylamide and (2-bromo-ethyl)cyclopropane as describe in Example 83 and isolated as a white solid (0.045 g, 38% yield). $^1$H NMR (400 MHz, $CDCl_3$) δ 7.44 (d, J=2 Hz, 1H), 7.29-7.35 (m, 2H), 7.05 (t, J=8 Hz, 2H), 6.80 (d, J=2 Hz, 1H), 5.96-6.01 (bm, 1H), 4.57 (d, J=4 Hz, 2H), 4.23 (t, J=7 Hz, 2H), 2.75 (s, 3H), 1.78 (q, J=7 Hz, 2H), 0.58-0.68 (m, 1H), 0.40-0.48 (m, 2H), 0.0-0.04 (m, 2H); MS (M+H)+=385.2; R_t=1.48 min; HRMS (M+H)+=385.15.

Example 86

Synthesis of 2-{1-[2-(1H-indol-3-yl)-ethyl]-1H-pyrazol-3-yl}-4-methyl-thiazole-5-carboxylic acid 4-fluoro-benzylamide

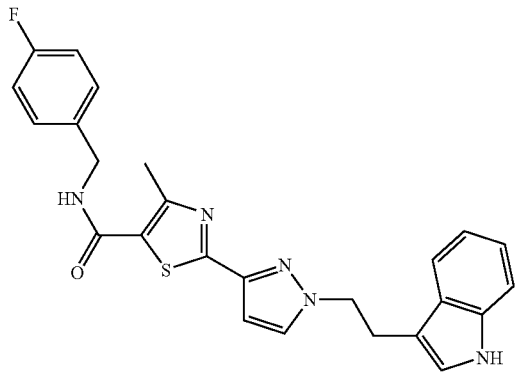

The title compound was prepared from 4-methyl-2-(2H-pyrazol-3-yl)thiazole-5-carboxylic acid 4-fluoro-benzylamide and 3-(2-bromo-ethyl)-1H-indole as describe in Example 83 and isolated as a yellow solid (0.056 g, 40% yield). $^1$H NMR (400 MHz, CDCl$_3$) δ 8.01 (bs, 1H), 7.56 (d, J=8 Hz, 1H), 7.31-7.38 (m, 2H), 7.20-7.25 (m, 1H), 7.10-7.16 (m, 2H), 6.81 (d, J=2 Hz, 1H), 6.70 (d, J=2 Hz, 1H), 5.99-6.04 (m, 1H), 4.59 (d, J=4 Hz, 2H), 4.45 (t, J=7 Hz, 2H), 3.35 (t, J=7 Hz, 2H), 2.76 (s, 3H); MS (M+H)+=460.2; R_t=1.47 min; HRMS (M+H)+=460.16.

Example 87

Synthesis of 2-{1-[2-(4-Methoxy-phenyl)-ethyl]-1H-pyrazol-3-yl}-4-methyl-thiazole-5-carboxylic acid 4-fluoro-benzylamide

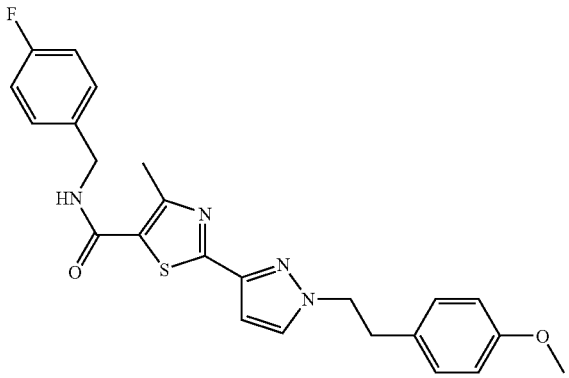

The title compound was prepared from 4-methyl-2-(2H-pyrazol-3-yl)thiazole-5-carboxylic acid 4-fluoro-benzylamide and 1-(2-bromo-ethyl)-4-methoxy-benzene as describe in Example 83 and isolated as a white solid (0.045 g, 38% yield). $^1$H NMR (400 MHz, CDCl$_3$) δ 7.30-7.35 (m, 2H), 7.14 (d, J=2 Hz, 1H), 7.04 (t, J=8 Hz, 2H), 6.97 (d, J=8 Hz, 2H), 6.80 (d, J=8 Hz, 2H), 6.71 (d, J=2 Hz, 1H), 6.03-6.09 (m, 1H), 4.57 (d, J=4 Hz, 2H), 4.32 (t, J=7 Hz, 2H), 3.77 (s, 3H); 3.12 (t, J=7 Hz, 2H), 2.75 (s, 3H); MS (M+H)+=451.2; R_t=1.49 min; HRMS (M+H)+=451.16.

Example 88

Synthesis of 2-{1-[2-(4-fluoro-phenyl)-ethyl]-1H-pyrazol-3-yl}-4-methyl-thiazole-5-carboxylic acid (2-pyridin-3-yl-ethyl)amide

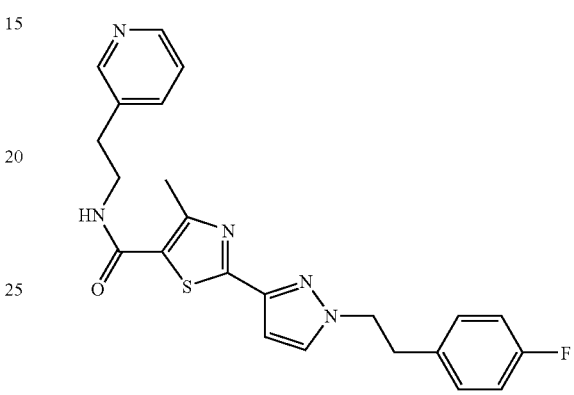

Part A. Synthesis of 4-methyl-2-(2H-pyrazol-3-yl)-thiazole-5-carboxylic acid ethyl ester To a solution of 2-bromo-4-methyl-thiazole-5-carboxylic acid ethyl ester (2.0 g, 7.99 mmol) in toluene (60 mL), water (20 mL) and ethanol (20 mL) was added 1H-pyrazole-5-boronic acid (1.79 g, 15.99 mmol), Pd(PPh$_3$)$_4$ (0.92 g, 0.80 mmol), and potassium carbonate (3.30 g, 23.98 mmol). The resulting mixture was degassed three times and heated to 100° C. for 16 hr. The reaction mixture was cooled to room temperature, diluted with ethyl acetate (200 mL) and washed with brine (2×100 mL). The organic phase was dried (Na$_2$SO$_4$) and evaporated. The residue was purified by flash column chromatography (hexanes-ethyl acetate, 1:1) to provide 4-methyl-2-(2H-pyrazol-3-yl)-thiazole-5-carboxylic acid ethyl ester as a yellow solid (1.5 g, 83% yield). MS (M+H)+=238; R_t=1.2 min.

Part B. Synthesis of 2-{1-[2-(4-fluoro-phenyl)-ethyl]-1H-pyrazol-3-yl}-4-methyl-thiazole-5-carboxylic acid ethyl ester A solution of 4-methyl-2-(2H-pyrazol-3-yl)-thiazole-5-carboxylic acid ethyl ester (2.5 g, 10.54 mmol) in dimethyl sulfoxide (50 mL) was treated with 1-(2-bromo-ethyl)-4-fluoro-benzene (2.10 g, 10.54 mmol) and potassium carbonate (4.30 g, 31.64 mmol), and the reaction mixture was heated to 90° C. for 16 hr. The reaction mixture was cooled to room temperature, diluted with ethyl acetate (100 mL), and washed with brine (2×100 mL). The organic phase was dried (Na$_2$SO$_4$) and evaporated. The residue was purified by flash column chromatography (hexanes:ethyl acetate, 1:1) to provide 2-{1-[2-(4-fluoro-phenyl)-ethyl]-1H-pyrazol-3-yl}-4-methyl-thiazole-5-carboxylic acid ethyl ester as a white solid (1.57 g, 45% yield). MS (M+H)+=360; R_t=1.65 min.

Part C. Synthesis of 2-{1-[2-(4-fluoro-phenyl)-ethyl]-1H-pyrazol-3-yl}-4-methyl-thiazole-5-carboxylic acid A mixture of 2-{1-[2-(4-fluoro-phenyl)-ethyl]-1H-pyrazol-3-yl}-4-methyl-thiazole-5-carboxylic acid ethyl ester (0.5 g, 1.39 mmol) and NaOH (0.22 g, 5.57 mmol) in tetrahydrofuran (10 mL) and water (5 mL) was heated to reflux for 16 hr. The reaction mixture was cooled to room temperature, and neutralized with 5% HCl to pH=6. The precipitate was filtered and dried to provide 2-{1-[2-(4-fluoro-phenyl)-ethyl]-1H-pyrazol-3-yl}-4-methyl-thiazole-5-carboxylic acid as a yellow solid (0.40 g, 87%) MS (M+H)$^+$=332; R$_t$=1.04 min.

Part D. Synthesis of 2-{1-[2-(4-fluoro-phenyl)-ethyl]-1H-pyrazol-3-yl}-4-methyl-thiazole-5-carboxylic acid (2-pyridin-3-yl-ethyl)-amide To a solution of 2-{1-[2-(4-fluoro-phenyl)-1H-pyrazol-3-yl}-4-methyl-thiazole-5-carboxylic acid (0.1 g, 0.30 mmol) in methylene chloride (5 mL) was added 2-pyridin-3-yl-ethylamine (0.04 g, 0.33 mmol), benzotriazol-1-yloxytris(dimethylamino)-hexafluorophosphate (0.146 g, 0.33 mmol) and N,N-diisopropylethylamine (0.1 mL, 0.60 mmol) and the mixture was stirred under nitrogen at room temperature for 16 hr. The reaction mixture was diluted with methylene chloride (50 mL), washed with water (50 mL) and brine (2×50 mL). The organic phase was dried (Na$_2$SO$_4$) and evaporated. The residue was purified by preparative thin layer chromatography over silica gel eluting with 50% ethyl acetate, 50% hexane to provide 2-{1-[2-(4-fluoro-phenyl)-ethyl]-1H-pyrazol-3-yl}-4-methyl-thiazole-5-carboxylic acid (2-pyridin-3-yl-ethyl)-amide as a white solid (0.095 g, 73%). $^1$H NMR (400 MHz, CDCl$_3$) δ 8.50 (d, J=2 Hz, 2H), 7.58 (d, J=4 Hz, 1H), 7.25-7.28 (m, 1H), 7.14 (d, J=2 Hz, 1H), 6.90-7.03 (m, 4H), 6.70 (d, J=2 Hz, 1H), 5.96-6.03 (m, 1H), 4.34 (t, J=7 Hz, 2H), 3.65-3.73 (m, 2H), 3.17 (t, J=7 Hz, 2H), 2.95 (t, J=7 Hz, 2H), 2.68 (s, 3H). MS (M+H)$^+$=436.2; R$_t$=1.28 min; HRMS (M+H)$^+$=436.16.

Example 89

Synthesis of 2-{1-[2-(4-fluoro-phenyl)-ethyl]-1H-pyrazol-3-yl}-4-methyl-thiazole-5-carboxylic acid pyridin-3-ylamide

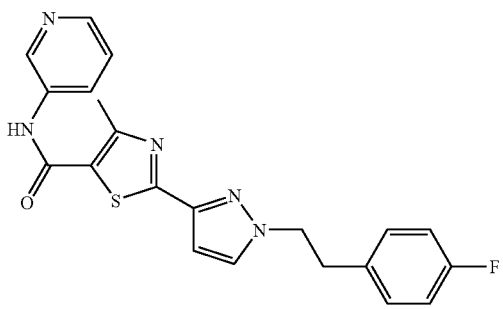

The title compound was prepared from 2-{1-[2-(4-fluoro-phenyl)-ethyl]-1H-pyrazol-3-yl}-4-methyl-thiazole-5-carboxylic acid and pyridine-3-ylamine as describe in Example 88 and isolated as a yellow solid (0.085 g, 71% yield). $^1$H NMR (400 MHz, CDCl$_3$) δ 8.63 (d, J=2.27 Hz, 1H), 8.40 (d, J=4 Hz, 1H), 8.23 (d, J=4 Hz, 1H), 7.61 (s, 1H), 7.32-7.36 (m, 1H), 7.18 (d, J=2 Hz, 1H), 6.91-7.05 (m, 4H), 6.76 (d, J=2 Hz, 1H), 4.37 (t, J=7 Hz, 2H), 3.19 (t, J=7 Hz, 2H), 2.81 (s, 3H); MS (M+H)$^+$=408.1; R$_t$=1.32 min; HRMS (M+H)$^+$=408.13.

Example 90

Synthesis of 2-{1-[2-(4-fluoro-phenoxy)-ethyl]-1H-pyrazol-3-yl}-4-methyl-thiazole-5-carboxylic acid benzylamide

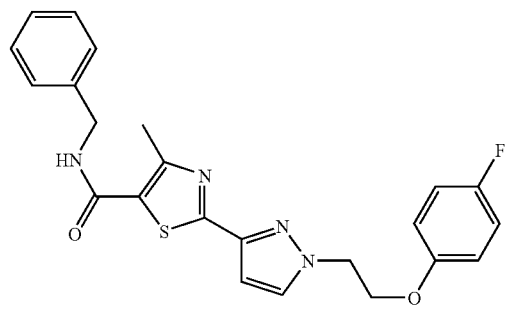

Part A. Synthesis of 2-bromo-4-methyl-thiazole-5-carboxylic acid benzylamide A solution of 2-bromo-4-methyl-thiazole-5-carboxylic acid (3.00 g, 13.51 mmol) in methylene chloride (20 mL) was added benzyl amine (1.60 mL, 14.86 mmol), benzotriazol-1-yloxytris(dimethylamino)phosphonium hexafluorophosphate (6.57 g, 14.86 mmol) and N,N-diisopropylethylamine (4.71 mL, 27.02 mmol) and the mixture was stirred under nitrogen at room temperature for 16 hr. The reaction mixture was diluted with methylene chloride (100 mL), and washed with water (100 mL) and brine (2×100 mL). The organic phase was dried (Na$_2$SO$_4$) and evaporated. The residue was purified by flash-chromatography (eluent hexanes-ethyl acetate, 1:1) to provide 2-bromo-4-methyl-thiazole-5-carboxylic acid benzyl amide as a yellow solid (3.50 g, 83% yield). MS (M+H)$^+$=312; R$_t$=1.31 min.

Part B. Synthesis of 4-methyl-2-(2H-pyrazol-3-yl)-thiazole-5-carboxylic acid benzylamide A solution of 2-bromo-4-methyl-thiazole-5-carboxylic acid, benzyl amide (2.0 g, 6.43 mmol) in toluene (30 mL), water (10 mL) and ethanol (10 mL) was added 1H-pyrazole-5-boronic acid (1.44 g, 12.86 mmol), Pd(PPh$_3$)$_4$ (0.74 g, 0.643 mmol), and potassium carbonate (2.67 g, 19.29 mmol). The resulting mixture was degassed three times and heated to 100° C. for 16 hr. The reaction mixture was cooled to room temperature, diluted with ethyl acetate (100 mL) and washed with brine (2×100 mL). The organic phase was dried (Na$_2$SO$_4$) and evaporated. The residue was purified by preparative thin layer chromatography over silica gel eluting with 1:1 ethyl acetate:hexane to provide 4-methyl-2-(2H-pyrazol-3-yl)-thiazole-5-carboxylic acid benzylamide (1.25 g, 66% yield) as a white solid. MS (M+H)$^+$=299; R$_t$=1.06 min; HRMS (M+H)$^+$=299.

Part C; Synthesis of 2-{1-[2-(4-fluoro-phenoxy)-ethyl]-1H-pyrazol-3-yl}-4-methyl-thiazole-5-carboxylic acid benzylamide A solution of 4-methyl-2-(2H-pyrazol-3-yl)-thiazole-5-carboxylic acid benzylamide (0.2 g, 0.61 mmol) in dimethyl sulfoxide (5 mL) was treated with 4-fluorophenoxyethyl bromide (0.14 g, 0.67 mmol) and potassium carbonate (0.30 g, 2.0 mmol), and the reaction mixture was heated to 90° C. for 16 hr. The reaction mixture was cooled to room temperature, diluted with ethyl acetate (50 mL), and washed with brine (2×50 mL). The organic phase was dried (Na$_2$SO$_4$) and evaporated. The residue was purified by preparative thin layer chromatography over silica gel (methylene chloride:methanol, 95:5) to provide 2-{1-[2-(4-fluoro-phenoxy)-ethyl]-1H-pyrazol-3-yl}-4-methyl-thiazole-5-carboxylic acid benzylamide (0.071 g, 51% yield) as a white solid.

Example 91

Synthesis of 4-methyl-2-[1-((R)-2-phenyl-propyl) 1H-pyrazol-3-yl]-thiazole-5-carboxylic acid benzylamide

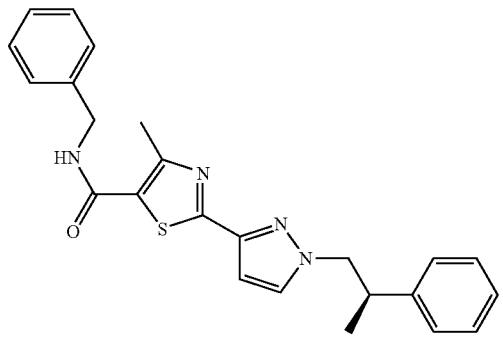

The title compound was prepared from 4-methyl-2-(2H-pyrazol-3-yl)-thiazole-5-carboxylic acid benzylamide and 2-(bromo-1-methyl-ethyl)-benzene as described in Example 90 and isolated by chiral separation (90/10, heptane/isopropyl alcohol). $^1$H NMR (400 MHz, CDCl$_3$) δ 7.35-7.41 (m, 5H), 7.20-7.35 (m, 3H), 7.14 (d, J=4 Hz, 2H), 7.08 (d, J=2 Hz, 1H), 6.75-6.82 (bs, 1H), 6.66 (d, J=2 Hz, 1H), 4.60 (d, J=8 Hz, 2H), 4.20-4.32 (m, 2H), 3.38-3.46 (m, 1H), 2.73 (s, 3H), 1.30 (d, J=4 Hz, 3H); MS (M+H)$^+$=417.2; R$_t$=1.32 min; HRMS (M+H)$^+$=417.17.

Example 92

Synthesis of 4-methyl-2-[1-((S)-2-phenyl-propyl) 1H-pyrazol-3-yl]-thiazole-5-carboxylic acid benzylamide

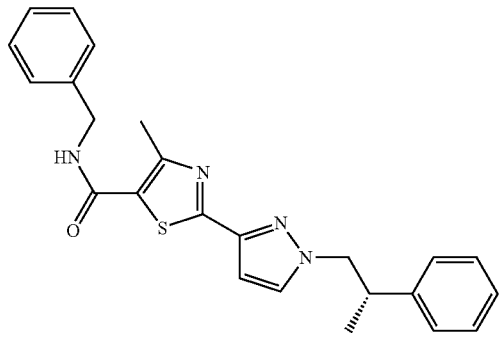

The title compound was prepared from 4-methyl-2-(2H-pyrazol-3-yl)-thiazole-5-carboxylic acid benzylamide and 2-(bromo-1-methyl-ethyl)-benzene as described in Example 90 and isolated by chiral separation (90:10, heptane:isopropyl alcohol). $^1$H NMR (400 MHz, CDCl$_3$) δ 7.20-7.39 (m, 8H), 7.13 (d, J=4 Hz, 2H), 7.04 (d, J=2 Hz, 1H), 6.68 (d, J=2 Hz, 1H), 5.98-6.04 (bm, 1H), 4.62 (d, J=8 Hz, 2H), 4.17-4.32 (m, 2H), 3.33-3.44 (m, 1H), 2.75 (s, 3H), 1.29 (d, J=4 Hz, 3H); MS (M+H)$^+$=417.2; R$_t$=1.32 min; HRMS (M+H)$^+$=417.17.

Example 93

Synthesis of 2-{1-[2-(4-fluoro-phenyl)-ethyl]-5-methyl-1H-pyrazol-3-yl}-4-methyl-thiazole-5-carboxylic acid (pyridin-3-ylmethyl)amide

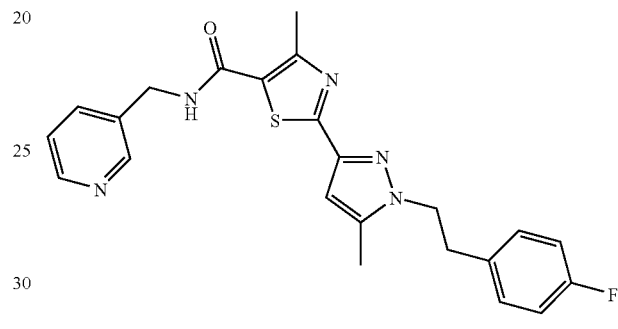

Part A. Synthesis of 3,4-diiodo-5-methyl-1H-pyrazole

A solution of 3-methyl-1H-pyrazole (10.0 g, 121.8 mmol) in water (500 mL), was treated with hexadecyltrimethylammonium bromide (1.10 g, 3.04 mmol), NaOH (9.74 g, 243.6 mmol), and iodine (153 g, 609 mmol). The reaction mixture was heated to reflux at 100° C. for 16 hr. The reaction mixture was cooled to room temperature and filtered through celite. The residue was diluted with ethyl acetate (500 mL), and washed with sodium thiosulfate (200 mL), water (300 mL), and brine (300 mL). The organic phase was dried (Na$_2$SO$_4$) and evaporated. The residue was triturated with n-pentane to provide 3,4-diiodo-5-methyl-1H-pyrazole as a brown solid (38.5 g, 96%). MS (M+H)$^+$=334; R$_t$=1.21.

Part B. Synthesis of 3-iodo-5-methyl-1H-pyrazole

A solution of 3,4-diiodo-5-methyl-1H-pyrazole (6.0 g, 18.01 mmol) was added triethyl amine trihydrofluoride (10 mL, 54.05 mmol). The reaction mixture was heated to 110° C. for 16 hr. The reaction mixture was cooled to room temperature, diluted with ethyl acetate (300 mL) and washed with NaHCO$_3$ (2×200 mL), and brine (200 mL). The organic phase was dried (Na$_2$SO$_4$) and evaporated. This material, 3-iodo-5-methyl-1H-pyrazole, was used without further purification (3.50 g, 95% yield) as a yellow solid.

Part C. Synthesis of 1-[2-(4-fluoro-phenyl)-ethyl]-3-iodo-5-methyl-1H-pyrazole

A solution of 3-iodo-5-methyl-1H-pyrazole (1.45 g, 6.97 mmol) in dimethyl sulfoxide (10 mL) was treated with 1-(2-bromo-ethyl)-4-fluoro-benzene (1.41 g, 6.97 mmol) and potassium carbonate (2.89 g, 20.91 mmol), and the reaction mixture was heated to 95° C. for 16 hr. The reaction mixture was cooled to room temperature, diluted with ethyl acetate (100 mL), and washed with brine (2×100 mL). The organic phase was dried (Na$_2$SO$_4$) and evaporated. The residue was purified by preparative thin layer chromatography over silica gel (hexanes:ethyl acetate, 1:1) to provide 1-[2-(4-fluoro-phenyl)-ethyl]-3-iodo-5-methyl-1H-pyrazole as a yellow oil. MS (M+H)$^+$=331.

Part D. Synthesis of 2-{1-[2-(4-fluoro-phenyl)-ethyl]-5-methyl-1H-pyrazol-3-yl}-4-methyl-thiazole-5-carboxylic acid ethyl ester. To a stirred suspension of zinc dust (1.30 g, 1.99 mmol) in tetrahydrofuran (5 mL) was added 1,2-dibromoethane (0.05 mL, 0.54 mmol), trimethylsilyl chloride (0.03 mL, 0.24 mmol) and a solution of 2-bromo-4-methyl-thiazole-5-carboxylic acid ethyl ester (0.50 g, 1.99 mmol) in tetrahydrofuran (5 mL). The reaction mixture was heated to 67° C. for 2 hr. The reaction mixture was cooled to room temperature and a solution of 1-[2-(4-fluoro-phenyl)-ethyl]-3-iodo-5-methyl-1H-pyrazole (1.0 g, 2.99 mmol) in tetrahydrofuran (2 mL) and Pd (PPh$_3$)$_4$ (0.05 g, 0.04 mmol) was added. The reaction mixture was heated to reflux for 16 hr. The reaction mixture was cooled to room temperature, diluted with ethyl acetate (100 mL), and washed with brine (2×100 mL). The organic phase was dried (Na$_2$SO$_4$) and evaporated. The residue was purified by preparative thin layer chromatography over silica gel (hexanes:ethyl acetate, 1:1) to provide 2-{1-[2-(4-fluoro-phenyl)-ethyl]-5-methyl-1H-pyrazol-3-yl}-4-methyl-thiazole-5-Carboxylic acid ethyl ester as a yellow solid (0.32 g, 74% yield). MS (M+H)$^+$=251.

Part E. Synthesis of 2-{1-[2-(4-fluoro-phenyl)-ethyl]-5-methyl-1H-pyrazol-3-yl}-4-methyl-thiazole-5-carboxylic acid A mixture of 2-{1-[2-(4-fluoro-phenyl)-ethyl]-5-methyl-1H-pyrazol-3-yl}-4-methyl-thiazole-5-carboxylic acid ethyl ester (0.32 g, 0.86 mmol), NaOH (0.17 g, 4.29 mmol) in tetrahydrofuran (5 mL) and water (5 mL) was heated to reflux for 16 hr. The solvent was removed in vacuo and the residue was neutralized with 5% HCl to pH 5-6. The resulting solid was filtered and dried to provide 2-{1-[2-(4-fluoro-phenyl)-ethyl]-5-methyl-1H-pyrazol-3-yl}-4-methyl-thiazole-5-carboxylic acid as a white solid (0.21 g, 70% yield). This material was used without further purification.

Part F. Synthesis of 2-{1-[2-(4-fluoro-phenyl)-ethyl]-5-methyl-1H-pyrazol-3-yl}-4-methyl-thiazole-5-carboxylic acid (pyridin-3-ylmethyl-amide)

To a solution of 2-{1-[2-(4-fluoro-phenyl)-ethyl]-5-methyl-1H-pyrazol-3-yl}-4-methyl-thiazole-5-carboxylic acid (0.15 g, 0.43 mmol) in methylene chloride (10 mL) was added 2-pyridin-3-yl-ethylamine (0.05 g, 0.48 mmol), benzotriazol-1-yloxytris-(dimethylamino)phosphonium hexafluorophosphate (0.21 g, 0.48 mmol) and N,N-diisopropylethylamine (0.15 mL, 0.87 mmol). The reaction mixture was stirred under nitrogen at room temperature for 16 hr. The reaction mixture was diluted with methylene chloride (50 mL), washed with water (50 mL) and brine (2×50 mL). The organic phase was dried (Na$_2$SO$_4$) and evaporated. The residue was purified by preparative thin layer chromatography over silica gel (methylene chloride:methanol, 98:2) to provide 2-{1-[2-(4-fluoro-phenyl)-ethyl]-5-methyl-1H-pyrazol-3-yl}-4-methyl-thiazole-5-carboxylic acid (pyridin-3-ylmethyl-amide as a white solid (0.052 g, 29% yield). $^1$H NMR (400 MHz, CDCl$_3$) δ 8.62 (s, 1H), 8.57 (d, J=4 Hz, 1H), 7.73 (d, J=4 Hz, 1H), 7.27-7.32 (m, 1H), 6.90-6.99 (m, 4H), 6.49 (s, 1H), 6.05-6.11 (bm, 1H), 4.64 (d, J=4 Hz, 2H), 4.23 (t, J=7 Hz, 2H), 3.13 (t, J=7 Hz, 2H), 2.76 (s, 3H), 1.56 (s, 3H); MS (M+H)$^+$=435.9; R$_t$=1.31 min; HRMS (M+H)$^+$=436.16.

Example 94

Synthesis of 2-{1-[2-(4-fluoro-phenyl)-ethyl]-5-trifluoromethyl-1H-pyrazol-3-yl}-4-methyl-thiazole-5-carboxylic acid (pyridin-3-ylmethyl)amide

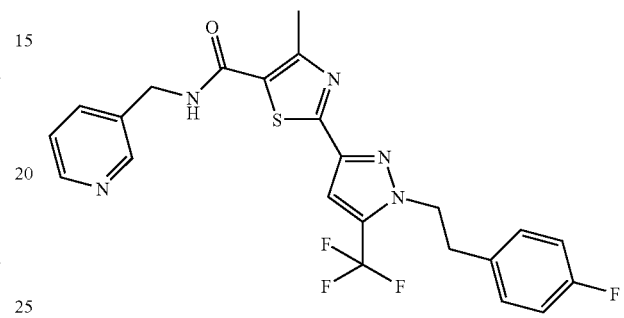

The title compound was prepared from 2-{1-[2-(4-fluoro-phenyl)-ethyl]-5-trifluoromethyl-1H-pyrazol-3-yl}-4-methyl-thiazole-5-carboxylic acid and 2-pyridin-3-yl-ethylamine as described in Example 93 and isolated as a white solid. $^1$H NMR (400 MHz, DMSO-d$_6$) δ 8.99 (t, J=3 Hz, 1H), 8.56 (d, J=2 Hz, 1H), 8.48 (d, J=3 Hz, 1H), 7.74 (d, J=8 Hz, 1H), 7.36-7.41 (m, 2H), 7.12-7.20 (m, 2H), 7.06 (t, J=8 Hz, 2H), 4.89 (t, J=8 Hz, 2H), 4.48 (d, J=4 Hz, 2H), 3.10 (t, J=8 Hz, 2H), 2.67 (s, 3H); MS (M+H)$^+$=489.9; R$_t$=1.57 min; HRMS (M+H)$^+$=490.13.

Example 95

Synthesis of 4-methyl-2-[5-methyl-1-(4-trifluoromethyl-benzyl)-1H-pyrazol-3-yl]-thiazole-5-carboxylic acid (pyridin-3-ylmethyl)amide

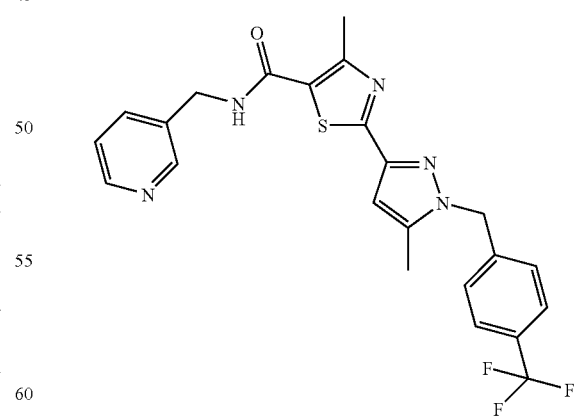

The title compound was prepared from 4-methyl-2-[5-methyl-1-(4-trifluoromethyl-benzyl)-1H-pyrazol-3-yl]-thiazole-5-carboxylic acid and 2-pyridin-3-yl-ethylamine as described in Example 93 and isolated as a white solid. $^1$H NMR (400 MHz, CDCl$_3$) δ 8.61 (s, 1H), 8.57 (d, J=4 Hz, 1H), 7.71 (d, J=8 Hz, 1H), 7.58 (d, J=8 Hz, 2H), 7.26-7.32 (m, 1H), 7.21 (d, J=4 Hz, 2H), 6.66 (s, 1H) 6.08-6.14 (m, 1H), 5.38 (s, 2N), 4.63 (d, J=4 Hz, 2H), 2.76 (s, 3H), 2.23 (s, 3H); MS (M+H)$^+$=472.1; R$_t$=1.41 min; HRMS (M+H)$^+$=472.14.

Example 96

Synthesis of 2-{1-[2-(4-fluoro-phenyl)-ethyl]-5-methyl-1H-pyrazol-3-yl}-4-methyl-thiazole-5-carboxylic acid 4-fluoro-benzylamide

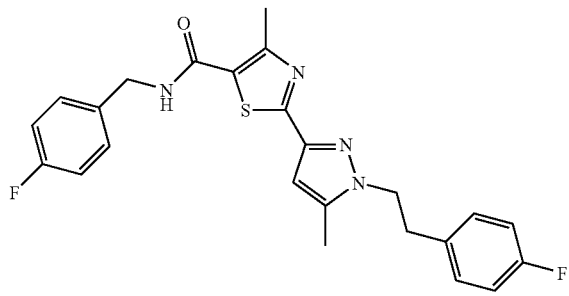

The title compound was prepared from 4-methyl-2-[5-methyl-2H-pyrazol-3-yl]-thiazole-5-carboxylic acid 4-fluorobenzylamide and 1-[2-(4-fluoro-phenyl)-ethyl]-3-iodo-5-methyl-1H-pyrazole as described in Example 93 and isolated as a white solid (0.035 g, 14% yield). $^1$H NMR (400 MHz, CDCl$_3$) δ 7.23-7.27 (m, 2H), 6.98 (t, J=8 Hz, 2H), 6.82-6.90 (m, 4H), 6.41 (s, 1H), 5.92-6.00 (bm, 1H), 4.50 (d, J=4 Hz, 2H), 4.15 (t, J=6 Hz, 2H), 3.05 (t, J=6, 2H), 2.68 (s, 3H), 1.84 (s, 3H); MS (M+H)$^+$=452.9; R$_t$=1.56 min; HRMS (M+H)$^+$= 453.16.

General LCMS Method

| Solvent B: | 1% Acetonitrile in 5 mM Ammonium Formate |
|---|---|
| Solvent D: | Acetonitrile |
| Flow (mL/min): | 4.0 |
| Stop time (mins): | 2.2 |
| Min Pressure (bar): | 0.0 |
| Max Pressure (bar) | 400 |
| Oven Temperature Left (° C.) | 50.0 |
| Oven Temperature Right (° C.) | 50.0 |

HP1100 LC Pump Gradient Timetable

| Time (min) | A % | B % | C % | D % |
|---|---|---|---|---|
| 0.00 | 0.0 | 90.0 | 0.0 | 10.0 |
| 1.70 | 0.0 | 10.0 | 0.0 | 90.0 |
| 1.85 | 0.0 | 10.0 | 0.0 | 90.0 |
| 1.86 | 0.0 | 0.0 | 0.0 | 0.0 |
| 2.10 | 0.0 | 0.0 | 0.0 | 0.0 |
| 2.15 | 0.0 | 90.0 | 0.0 | 10.0 |

Example 97

Measuring Stearoyl-CoA Desaturase Inhibition Activity of a Test Compound Using Mouse Liver Microsomes The identification of compounds of the invention as SCD inhibitors was readily accomplished using the SCD microsomal assay procedure described in Shanklin J. and Summerville C., *Proc. Natl. Acad. Sci. USA* (1991), Vol. 88, pp. 2510-2514, which is incorporated herein by reference in its entirety.

Preparation of Mouse Liver Microsomes:

Male ICR outbread mice, on a high-carbohydrate, low fat diet, under light halothane (15% in mineral oil) anesthesia are sacrificed by exsanguination during periods of high enzyme activity. Livers are immediately rinsed with cold 0.9% NaCl solution, weighed and minced with scissors. All procedures are performed at 4° C. unless specified otherwise. Livers are homogenized in a solution (1/3 w/v) containing 0.25 M sucrose, 62 mM potassium phosphate buffer (pH 7.0), 0.15 M KCl, 15 mM N-acetylcysteine, 5 mM MgCl$_2$, and 0.1 mM EDTA using 4 strokes of a Potter-Elvehjem tissue homogenizer. The homogenate is centrifuged at 10,400×g for 20 min to eliminate mitochondria and cellular debris. The supernatant is filtered through a 3-layer cheesecloth and centrifuged at 105,000×g for 60 min. The microsomal pellet is gently resuspended in the same homogenization solution with a small glass/teflon homogenizer and stored at −70° C. The absence of mitochondrial contamination is enzymatically assessed. The protein concentration is measured using bovine serum albumin as the standard.

Incubation of Mouse Liver Microsomes with Test Compounds:

Desaturase activity is measured as the release of $^3$H$_2$O from [9,10-$^3$H]stearoyl-CoA. Reactions per assay point conditions are as follows: 2 µL 1.5 mM stearoyl-CoA, 0.25 µL 1 mCi/mL $^3$H stearoyl CoA, 10 µL 20 mM NADH, 36.75 µL 0.1 M PK buffer (K$_2$HPO$_4$/NaH$_2$PO$_4$, pH 7.2). The test compound or control solution is added in a 1 µL volume. Reactions are started by adding 50 µL of microsomes (1.25 mg/mL). The plates are mixed and after 15 min incubation on a heating block (25° C.), the reactions are stopped by the addition of 10 µL 60% PCA. An aliquot of 100 µL is then transferred to a filter plate pretreated with charcoal and the plate centrifuged at 4000 rpm for 1 minute. The flow through containing the $^3$H$_2$O released by the SCD1 desaturation reaction is added to scintillation fluid and the radioactivity measured in a Packard TopCount. The data is analyzed to identify the IC$_{50}$ for test compounds and reference compounds. Representative compounds of the invention showed activity as inhibitors of SCD when tested in this assay. The activity was defined in terms of % SCD enzyme activity remaining at the desired concentration of the test compound or as the IC$_{50}$ concentration. The IC$_{50}$ (affinity) of the example compounds toward the stearoyl-CoA desaturase is comprised between around 20 µM and 0.0001 µM or between around 5 µM and 0.0001 µM or between around 1 µM and 0.0001 µM.

Example Activity Data

| Example | Compound name | Microsomal IC$_{50}$ (µM) |
|---|---|---|
| 37 | 4-Methyl-2-[1-(3-phenylpropyl)-1H-pyrazol-3-yl]-thiazole-5-carboxylic acid benzylamide | 0.071 |
| 87 | 2-{1-[2-(4-Methoxyphenyl)ethyl]-1H-pyrazol-3-yl}-4-methyl-thiazole-5-carboxylic acid 4-fluorobenzylamide | 0.096 |
| 85 | 2-[1-(2-Cyclopropyl-ethyl)-1H-pyrazol-3-yl]-4-methyl-thiazole-5-carboxylic acid 4-fluorobenzylamide | 0.147 |

-continued

| Example | Compound name | Microsomal IC$_{50}$ (µM) |
|---|---|---|
| 52 | 2-[1-(4-Cyano-benzyl)-1H-pyrazol-3-yl]-4-methylthiazole-5-carboxylic acid (pyridin-3-ylmethyl)amide | 0.074 |
| 79 | 4-Methyl-2-{1-[2-(methylphenylamino)-ethyl]-1H-pyrazol-3-yl}-thiazole-5-carboxylic acid (pyridin-3-ylmethyl)amide | 0.049 |
| 4 | 4-Methyl-2-(6-phenethylpyrazin-2-yl)-thiazole-5-carboxylic acid benzylamide | 0.042 |
| 29 | 2-{6-[(4-Fluorobenzyl)methylamino]-pyrazin-2-yl}-4-methyl-thiazole-5-carboxylic acid benzylamide | 0.124 |
| 16 | 4-Methyl-2-{6-[methyl-(3-phenylpropyl)-amino]pyrazin-2-yl}-thiazole-5-carboxylic acid 4-fluorobenzylamide | 0.164 |
| 22 | 2-{6-[(4-Methoxybenzyl)methylamino]-pyrazin-2-yl}-4-methylthiazole-5-carboxylic acid 4-fluorobenzylamide | 0.098 |
| 66 | 2-[1-(4-Methanesulfonylbenzyl)-1H-pyrazol-3-yl]-4-methylthiazole-5-carboxylic acid (pyridin-3-ylmethyl)amide | 0.172 |

Those skilled in the art are aware of a variety of modifications to this assay that can be useful for measuring inhibition of stearoyl-CoA desaturase activity in microsomes or in cells by test compounds.

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A compound selected from:
4-Methyl-2-(2H-pyrazol-3-yl)thiazole-5-carboxylic acid benzylamide;
4-Methyl-2-[1-(2-pyridin-2-yl-ethyl)-1H-pyrazol-3-yl]-thiazole-5-carboxylic acid benzylamide;
4-Methyl-2-(1-phenethyl-1H-pyrazol-3-yl)-thiazole-5-carboxylic acid benzylamide;
2-{1-[2-(4-Fluoro-phenyl)-ethyl]-1H-pyrazol-3-yl}-4-methyl-thiazole-5-carboxylic acid benzylamide;
2-[1-((R)-2-Hydroxy-2-phenyl-ethyl)-1H-pyrazol-3-yl]-4-methyl-thiazole-5-carboxylic acid benzylamide;
2-{1-[(R)-2-(4-Fluoro-phenyl)-2-hydroxy-ethyl]-1H-pyrazol-3-yl}-4-methyl-thiazole-5-carboxylic acid benzylamide;
2-{1-[2-(4-Fluoro-phenyl)-ethyl]-1H-pyrazol-3-yl}-4-methyl-thiazole-5-carboxylic acid 4-fluoro-benzylamide;
2-{1-[2-(4-Fluoro-phenoxy)-ethyl]-1H-pyrazol-3-yl}-4-methyl-thiazole-5-carboxylic acid benzylamide;
2-{1-[2-(3-Fluoro-phenyl)-ethyl]-1H-pyrazol-3-yl}-4-methyl-thiazole-5-carboxylic acid benzylamide;
4-Methyl-2-[1-(3-phenyl-propyl)-1H-pyrazol-3-yl]-thiazole-5-carboxylic acid benzylamide;
2-[1-((S)-2-Hydroxy-2-phenyl-ethyl)-1H-pyrazol-3-yl]-4-methyl-thiazole-5-carboxylic acid benzylamide;
2-{1-[2-(4-Methoxy-phenyl)-ethyl]-1H-pyrazol-3-yl}-4-methyl-thiazole-5-carboxylic acid benzylamide;
2-{1-[2-(4-Hydroxy-phenyl)-ethyl]-1H-pyrazol-3-yl}-4-methyl-thiazole-5-carboxylic acid benzylamide;
4-Methyl-2-[1-(2-phenoxy-ethyl)-1H-pyrazol-3-yl]-thiazole-5-carboxylic acid benzylamide;
2-{1-[2-(4-Fluoro-phenyl)-ethyl]-1H-pyrazol-3-yl}-4-methyl-thiazole-5-carboxylic acid (pyridin-3-ylmethyl)amide;
4-Methyl-2-[1-(3-methyl-butyl)-1H-pyrazol-3-yl]-thiazole-5-carboxylic acid benzylamide;
4-Methyl-2-[1-((R)-2-phenyl-propyl)-1H-pyrazol-3-yl]-thiazole-5-carboxylic acid benzylamide;
4-Methyl-2-[1-(2-phenoxy-ethyl)-1H-pyrazol-3-yl]-thiazole-5-carboxylic acid 4-fluoro-benzylamide;
4-Methyl-2-[1-(2-phenoxy-ethyl)-1H-pyrazol-3-yl]-thiazole-5-carboxylic acid (pyridin-3-ylmethyl)amide;
4-Methyl-2-[1-((S)-2-phenyl-propyl)-1H-pyrazol-3-yl]-thiazole-5-carboxylic acid benzylamide;
2-{1-[2-(1H-Indol-3-yl)-ethyl]-1H-pyrazol-3-yl}-4-methyl-thiazole-5-carboxylic acid 4-fluoro-benzylamide;
2-{1-[2-(4-Methoxy-phenyl)-ethyl]-1H-pyrazol-3-yl}-4-methyl-thiazole-5-carboxylic acid 4-fluoro-benzylamide;
2-[1-(2-Cyclopropyl-ethyl)-1H-pyrazol-3-yl]-4-methyl-thiazole-5-carboxylic acid 4-fluoro-benzylamide;
4-Methyl-2-[1-(2-methyl-2-phenyl-propyl)-1H-pyrazol-3-yl]-thiazole-5-carboxylic acid 4-fluoro-benzylamide;
2-{1-[2-(4-Fluoro-phenoxy)-ethyl]-1H-pyrazol-3-yl}-4-methyl-thiazole-5-carboxylic acid (pyridine-3-ylmethyl)amide;
2-{1-[2-(4-Methoxy-phenyl)-ethyl]-1H-pyrazol-3-yl}-4-methyl-thiazole-5-carboxylic acid (pyridin-3-ylmethyl)amide;
2-{1-[2-(4-Fluoro-phenyl)-ethyl]-1H-pyrazol-3-yl}-4-methyl-thiazole-5-carboxylic acid (2-pyridin-3-yl-ethyl)amide;
2-{1-[2-(4-Fluoro-phenyl)-ethyl]-1H-pyrazol-3-yl}-4-methyl-thiazole-5-carboxylic acid pyridin-3-ylamide;
4-Methyl-2-[1-(2-phenyl-propyl)-1H-pyrazol-3-yl]-thiazole-5-carboxylic acid (pyridin-3-ylmethyl)amide;
2-[1-(4-Fluoro-benzyl)-1H-pyrazol-3-yl]-4-methyl-thiazole-5-carboxylic acid (pyridin-3-ylmethyl)amide;
4-Methyl-2-[1-((R)-2-phenyl-propyl)-1H-pyrazol-3-yl]-thiazole-5-carboxylic acid (pyridin-3-ylmethyl)amide;
4-Methyl-2-[1-((S)-2-phenyl-propyl)-1H-pyrazol-3-yl]-thiazole-5-carboxylic acid (pyridin-3-ylmethyl)amide;
4-Methyl-2-[1-(3-trifluoromethyl-benzyl)-1H-pyrazol-3-yl]-thiazole-5-carboxylic acid (pyridin-3-ylmethyl)amide;
4-Methyl-2-[1-(2-methyl-2-phenyl-propyl)-1H-pyrazol-3-yl]-thiazole-5-carboxylic acid (pyridin-3-ylmethyl)amide;
4-Methyl-2-[1-(4-trifluoromethoxy-benzyl)-1H-pyrazol-3-yl]-thiazole-5-carboxylic acid (pyridin-3-ylmethyl)amide;
4-Methyl-2-[1-(4-trifluoromethyl-benzyl)-1H-pyrazol-3-yl]-thiazole-5-carboxylic acid (pyridin-3-ylmethyl)amide;
4-Methyl-2-{1-[2-(4-trifluoromethoxy-phenyl)ethyl]-1H-pyrazol-3-yl}-thiazole-5-carboxylic acid (pyridin-3-ylmethyl)amide;
2-[1-(2-Hydroxy-ethyl)-1H-pyrazol-3-yl]-4-methyl-thiazole-5-carboxylic acid (pyridin-3-ylmethyl)amide;
4-Methyl-2-[1-(2-phenylamino-ethyl)-1H-pyrazol-3-yl]-thiazole-5-carboxylic acid (pyridin-3-ylmethyl)amide;
2-{1-[2-(4-Fluoro-phenyl)amino-ethyl]-1H-pyrazol-3-yl}-4-methyl-thiazole-5-carboxylic acid (pyridin-3-ylmethyl)amide;

4-Methyl-2-{1-[2-(methyl-phenylamino)-ethyl]-1H-pyrazol-3-yl}-thiazole-5-carboxylic acid (pyridin-3-ylmethyl)amide;

2-{1-[2-(4-Fluoro-phenyl)-ethyl]-5-methyl-1H-pyrazol-3-yl}-4-methyl-thiazole-5-carboxylic acid 4-fluorobenzylamide;

2-[1-(3,5-Difluoro-benzyl)-1H-pyrazol-3-yl]-4-methyl-thiazole-5-carboxylic acid (pyridin-3-ylmethyl)amide;

2-[1-(4-tert-Butyl-benzyl)-1H-pyrazol-3-yl]-4-methyl-thiazole-5-carboxylic acid (pyridin-3-ylmethyl)amide;

2-[1-(4-Chloro-benzyl)-1H-pyrazol-3-yl]-4-methyl-thiazole-5-carboxylic acid (pyridin-3-ylmethyl)amide;

2-[1-(4-Chloro-2-fluoro-benzyl)-1H-pyrazol-3-yl]-4-methyl-thiazole-5-carboxylic acid (pyridin-3-ylmethyl)amide;

2-[1-(4-Ethyl-benzyl)-1H-pyrazol-3-yl]-4-methyl-thiazole-5-carboxylic acid (pyridin-3-ylmethyl)amide;

2-[1-(4-Cyano-benzyl)-1H-pyrazol-3-yl]-4-methyl-thiazole-5-carboxylic acid (pyridin-3-ylmethyl)amide;

2-[1-(3-Fluoro-benzyl)-1H-pyrazol-3-yl]-4-methyl-thiazole-5-carboxylic acid (pyridin-3-ylmethyl)amide;

2-[1-(4-Methanesulfonyl-benzyl)-1H-pyrazol-3-yl]-4-methyl-thiazole-5-carboxylic acid (pyridin-3-ylmethyl)amide;

4-Methyl-2-[1-(4-pyrazol-1-yl-benzyl)-1H-pyrazol-3-yl]-thiazole-5-carboxylic acid (pyridin-3-ylmethyl)amide;

2-[1-(3-Cyano-benzyl)-1H-pyrazol-3-yl]-4-methyl-thiazole-5-carboxylic acid (pyridin-3-ylmethyl)amide;

4-Methyl-2-[1-(4-[1,2,4]triazol-1-yl-benzyl)-1H-pyrazol-3-yl]-thiazole-5-carboxylic acid (pyridin-3-ylmethyl)amide;

4-Methyl-2-[1-(4-pyrrol-1-yl-benzyl)-1H-pyrazol-3-yl]-thiazole-5-carboxylic acid (pyridin-3-ylmethyl)amide;

2-[1-(3-Chloro-benzyl)-1H-pyrazol-3-yl]-4-methyl-thiazole-5-carboxylic acid (pyridin-3-ylmethyl)amide;

2-[1-(2-(tert-Butoxycarbonylamino)ethyl)-1H-pyrazol-3-yl]-4-methylthiazole-5-carboxylic acid (pyridin-3-ylmethyl)amide;

2-{1-[2-(4-Fluoro-phenyl)-ethyl]-5-methyl-1H-pyrazol-3-yl}-4-methyl-thiazole-5-carboxylic acid (pyridin-3-ylmethyl)amide;

2-{1-[2-(4-Fluoro-benzoylamino)-ethyl]-1H-pyrazol-3-yl}-4-methyl-thiazole-5-carboxylic acid (pyridin-3-ylmethyl)amide;

2-{1-[2-(4-Fluoro-benzenesulfonylamino)-ethyl]-1H-pyrazol-3-yl}-4-methyl-thiazole-5-carboxylic acid (pyridin-3-ylmethyl)amide;

2-{1-[2-(4-Fluoro-phenyl)-ethyl]-5-trifluoromethyl-1H-pyrazol-3-yl}-4-methyl-thiazole-5-carboxylic acid (pyridin-3-ylmethyl)amide;

4-Methyl-2-[1-(2-phenyl-propyl)-1H-pyrazol-3-yl]-thiazole-5-carboxylic acid benzylamide;

2-{1-[2-(4-Methoxy-phenyl)-ethyl]-1H-pyrazol-3-yl}-4-methyl-thiazole-5-carboxylic acid benzylamide;

4-Methyl-2-[5-methyl-1-(4-trifluoromethyl-benzyl)-1H-pyrazol-3-yl]-thiazole-5-carboxylic acid (pyridin-3-ylmethyl)amide;

2-[1-(2-Cyclohexyl-ethyl)-1H-pyrazol-3-yl]-4-methyl-thiazole-5-carboxylic acid benzylamide, or a pharmaceutically acceptable salt thereof.

2. A pharmaceutical composition, comprising: the compound according to claim 1, or a pharmaceutically acceptable salt thereof, and a pharmaceutically acceptable excipient or carrier.

* * * * *